United States Patent [19]

Bantle et al.

[11] Patent Number: 5,859,014

[45] Date of Patent: Jan. 12, 1999

[54] PYRIMIDINEDIONE, PYRIMIDINETRIONE, TRIAZINEDIONE AND TETRAHYDROQUINAZOLINEDIONE DERIVATIVES AS $\alpha_1$-ADRENERGIC RECEPTOR ANTAGONISTS

[75] Inventors: Gary W. Bantle, Calgary, Canada; Todd R. Elworthy, Palo Alto, Calif.; Angel Guzmán, Colonia Jardines en la Montana, Mexico; Saul Jaime-Figueroa; Francisco J. López-Tapia, both of Fremont, Calif.; David J. Morgans, Jr., Los Altos, Calif.; Arturo Pérez-Medrano, Mexico City, Mexico; Jürg R. Pfister, Los Altos, Calif.; Eric B. Sjogren, Mountain View, Calif.; Francisco X. Talamás, San Carlos, Calif.

[73] Assignee: Syntex (U.S.A.) Inc., Palo Alto, Calif.

[21] Appl. No.: 658,774

[22] Filed: Jun. 5, 1996

Related U.S. Application Data

[60] Provisional application No. 60/042,912, Jun. 9, 1995.

[51] Int. Cl.⁶ .................... C07D 239/04; C07D 239/10; A61K 31/505
[52] U.S. Cl. .................. 514/255; 544/295; 544/301; 544/311
[58] Field of Search .................... 544/295, 301, 544/311; 514/255

[56] References Cited

U.S. PATENT DOCUMENTS

| | | | |
|---|---|---|---|
| 4,216,216 | 8/1980 | Weber et al. | 424/251 |
| 4,931,444 | 6/1990 | Van Wauwe et al. | 514/252 |
| 5,075,308 | 12/1991 | Ishikawa et al. | 514/252 |

FOREIGN PATENT DOCUMENTS

| | | |
|---|---|---|
| 0 000 220 | 1/1979 | European Pat. Off. . |
| WO 93/17007 | 9/1993 | WIPO . |
| WO 96/16949 | 6/1996 | WIPO . |

OTHER PUBLICATIONS

*Derwent WPI*, Abstract No. 91–099173 (abstract of Japanese Patent Kokai No. 44,379/1991—Yamasa Shoyu K.K.) Derwent Publications Ltd., London, England, 1991; and *Chemical Abstracts*, Abstract No. 115:159177c, Chemical Abstracts Service, Columbus, Ohio, 1991.
*Patent Abstracts of Japan*, Abstract No. 14:458 (C–0766) (abstract of Japanese Patent Kokai No. 184,667/1990—Meiji Seika Kaisha Ltd.), Tokyo, Japan, 1990; and *Chemical Abstracts*, Abstract No. 114:12226p, Chemical Abstracts Service, Columbus, Ohio, 1990.
G. Romeo et al., "Heterocyclic systems containing the pyrimido–2,4–dione ring as selective ligands for the $\alpha_1$–adrenoceptors", *Il Farmaco*, 50(6), 471–477 (1995).
J.L. Mokrosz et al., "A search for new trazodone–like antidepressants: synthesis and preliminary binding studies", *Arch. Phar. (Weinheim)*, 328, 623–625 (1995).

*Chemical Abstracts*, Abstract No. 122:282093u (abstract of R. Villalobos–Molina et al., "The 5–HT₂ receptor antagonist, pelanserin, inhibits $\alpha_1$–adrenoceptor–mediated vasoconstriction in vitro", *Eur. J. Pharmacol.*, 277(2/3), 181–185 (1995)), Chemical Abstracts Service, Columbus, Ohio, 1995.
*Chemical Abstracts*, Abstract No. 106:188841j (abstract of J. Longmore et al., "Antagonism of phenylephrine–evoked sweating by trazodone and amitryptyline in humans in vivo", *Br. J. Clin. Pharmacol.*, 23(2), 245–246 (1987)), Chemical Abstracts Service, Columbus, Ohio, 1987.

*Primary Examiner*—Mukund J. Shah
*Assistant Examiner*—Deepak R. Rao
*Attorney, Agent, or Firm*—Heller Ehrman White & McAuliffe

[57] ABSTRACT

Compounds of Formula I:

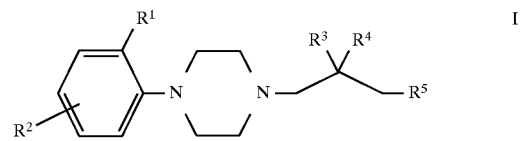

where $R^5$ is a group selected from Formulae (a), (b), (c) and (d):

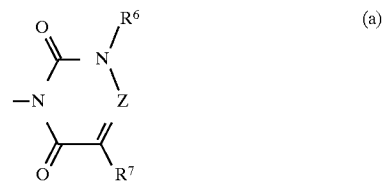

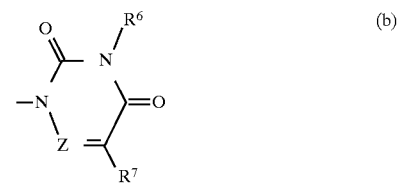

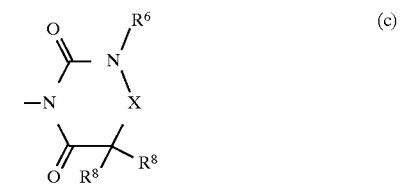

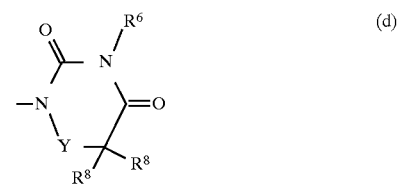

and the pharmaceutically acceptable salts and N-oxides thereof, are $\alpha_1$-adrenergic receptor antagonists useful for the treatment of diseases involving directly or indirectly an obstruction of the lower urinary tract, such as benign prostatic hyperplasia.

21 Claims, No Drawings

PYRIMIDINEDIONE, PYRIMIDINETRIONE, TRIAZINEDIONE AND TETRAHYDROQUINAZOLINEDIONE DERIVATIVES AS $\alpha_1$-ADRENERGIC RECEPTOR ANTAGONISTS

CROSS-REFERENCE TO RELATED APPLICATION

This application claims the benefit under 35 U.S.C. 119(e) of U.S. Provisional Application No 60/042,912, filed Jun. 9, 1995.

FIELD OF THE INVENTION

This invention relates to novel [3-(4-phenylpiperazin-1-yl)propyl]-, [3-(4-phenylpiperazin-1-yl)-2,2-dimethylpropyl]- and [1-(4-phenylpiperazin-1-yl methyl) cycloprop-1-ylmethyl]-pyrimidinedione, pyrimidinetrione, dihydropyrimidinedione, triazinedione and tetrahydroquinazolinedione derivatives as $\alpha_1$-adrenergic receptor antagonists, pharmaceutical formulations containing them, their uses as therapeutic agents, and syntheses therefor.

BACKGROUND OF THE INVENTION $\alpha_1$-Adrenergic receptors ($\alpha_1$-adrenoceptocs) mediate the contractile state of smooth muscle tissue. For example, hypersympathetic activity produces contraction of vascular smooth muscle which -Leads to elevated blood pressures. Thus, $\alpha_1$-adrenoceptor antagonists find use as antihypertensive agents. $\alpha_1$-Adrenoceptor stimulation also produces contraction of urethral and bladder neck smooth muscle, leading to increased resistance in urinary outflow. Thus, $\alpha_1$-adrenoceptor antagonists are useful in treating conditions which relate directly or indirectly to obstructive uropathies, particularly obstruction due to benign prostatic hyperplasia (BPH) (Lepor, H. *The Prostate Supplement* 1990, 3, 75–84). However, the amount of $\alpha_1$-adrenoceptor antagonist required to produce a therapeutic effect with regard to urinary outflow, can produce an excessive decrease of blood pressure and/or an inhibition of the mechanism by which normal blood pressure is maintained during changes in posture (i.e., postural hypotension). Thus, antagonists which can selectively reduce $\alpha_1$-adrenoceptor hyperactivity in prostatic and/or lower urinary tract smooth muscle, without affecting blood pressure or causing postural hypotension, are desirable.

The disclosures of these and other documents referred to throughout this application (e.g., in the Pharmacology section of the Detailed Description of the Invention) are incorporated herein by reference.

SUMMARY OF THE INVENTION

A first aspect of this invention is compounds of Formula I:

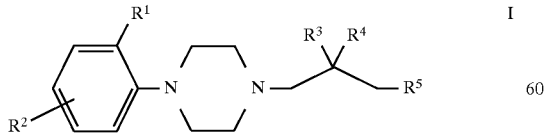

in which:

$R^1$ is acetylamino, amino, cyano, trifluoroacetylamino, halo, hydro, hydroxy, nitro, methylsulfonylamino, 2-propynyloxy, a group selected from $(C_{1-6})$alkyl, $(C_{3-6})$cycloalkyl, $(C_{3-6})$cycloalkyl$(C_{1-4})$alkyl, $(C_{1-6})$alkyloxy, $(C_{3-6})$cycloalkyloxy, $(C_{3-6})$cycloalkyl$(C_{1-4})$alkyloxy and $(C_{1-4})$alkylthio (which group is optionally further substituted with one to three halo atoms) or a group selected from aryl, aryl$(C_{1-4})$alkyl, heteroaryl, heteroaryl$(C_{1-4})$alkyl, aryloxy, aryl$(C_{1-4})$alkyloxy, heteroaryloxy and heteroaryl$(C_{1-4})$alkyloxy (which aryl and heteroaryl are optionally further substituted with one to two radicals independently selected from halo and cyano);

$R_2$ is cyano, halo, hydro, hydroxy or a group selected from $(C_{1-6})$alkyl and $(C_{1-6})$alkyloxy (which group is optionally further substituted with one to three halogen atoms);

$R^3$ and $R^4$ are both hydro or methyl or together are ethylene; and $R^5$ is a group selected from Formulae (a), (b), (c) and (d):

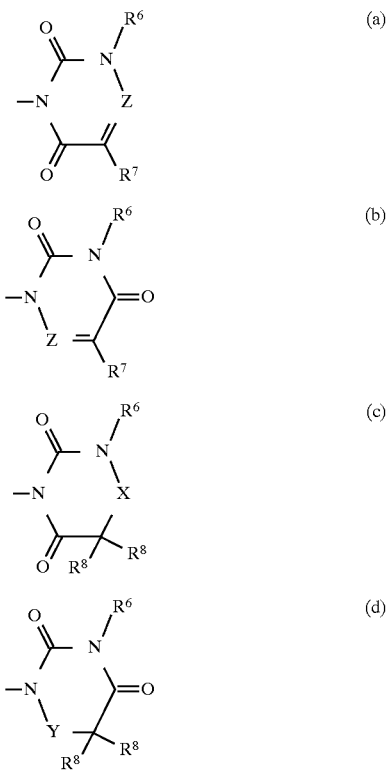

in which:

X is C(O), $CH_2$ or CH(OH);
Y is $CH_2$ or CH(OH);
Z is N or C($R^9$), wherein $R^9$ is hydro, $(C_{1-6})$alkyl or hydroxy;
$R^6$ is hydro, a group selected from $(C_{1-6})$alkyl, $(C_{3-6})$cycloalkyl, $(C_{3-6})$cycloalkyl$(C_{1-4})$alkyl (which group is optionally further substituted with one to three halo atoms) or a group selected from aryl, heteroaryl, aryl$(C_{1-4})$alkyl and heteroaryl$(C_{1-4})$alkyl (which aryl and heteroaryl are optionally further substituted with one to three radicals selected from halo, cyano, $(C_{1-6})$alkyloxy, $(C_{1-6})$alkyl and aryl);
$R^7$ is $(C_{1-6})$alkanoyl, carbamoyl, cyano, di$(C_{1-6})$allkylamino, halo, hydro, hydroxy, hydroxyiminomethyl, $(C_{1-6})$alkylsulfonyl, $(C_{1-4})$alkylthio, a group selected from $(C_{1-6})$ alkyl, $(C_{3-6})$ cycloalkyl, $(C_{1-6})$alkyloxy and $(C_{1-6})$alkyloxy$(C_{1-4})$alkyl (which group is optionally further substituted with one to three radicals selected from halo, hydroxy or ($C_{1-6}$)alkyloxy) or a group selected from aryl, heteroaryl, aryl($C_{1-4}$)alkyl and heteroaryl($C_{1-4}$)alkyl (which aryl and heteroaryl are optionally further substituted with one to three radicals selected from halo, cyano, ($C_{1-6}$)alkyloxy, ($C_{1-6}$)alkyl and aryl) or $R^7$ and $R^9$ together are tetramethylene; and each $R^8$ is independently hydro, hydroxy, methyl or ethyl; and the pharmaceutically acceptable salts and N-oxides thereof.

A second aspect of this invention is pharmaceutical compositions containing a compound of Formula I, or a pharmaceutically acceptable salt or N-oxide thereof, in admixture with one or more suitable excipients.

A third aspect of this invention is a method for treating a disease involving directly or indirectly an obstruction of the lower urinary tract in an animal in need of such treatment, particularly for treating obstruction due to benign prostate hyperplasia, which method comprises administering to such animal a therapeutically effective amount of a compound of Formula I or a pharmaceutically acceptable salt or N-oxide thereof.

A fourth aspect of this invention is the processes for preparing compounds of Formula I and is set forth in "Detailed Description of the Invention".

DETAILED DESCRIPTION OF THE INVENTION

Definitions

Unless otherwise stated, the following terms used in the specification and claims have the meanings given below:

"Alkyl", as in ($C_{1-4}$)alkylthio, ($C_{1-6}$)alkyl or ($C_{1-6}$)alkyloxy, means a straight or branched saturated hydrocarbon radical having from one to the number of carbon atoms designated optionally substituted with one to three halo atoms (e.g., optionally substituted ($C_{1-4}$)alkylthio includes methylthio, ethylthio, 2,2,2-trifluoroethylthio, etc.; optionally substituted ($C_{1-6}$)alkyl includes methyl, trifluoromethyl, ethyl, propyl, isopropyl, butyl, isobutyl, sec-butyl, tert-butyl, etc.; and optionally substituted ($C_{1-6}$)alkyloxy includes methoxy, difluoromethoxy, trifluoromethoxy, ethoxy, 2,2,2-trifluoroethoxy, propoxy, isopropoxy, butoxy, isobutoxy, sec-butoxy, tert:-butoxy, etc.).

"Alkanoyl" means the radical —C(O)R having from one to the number of carbon atoms designated (e.g., formyl, acetyl, propionyl, butyryl, etc.).

"Cycloalkyl", as in ($C_{3-6}$)cycloalkyl, ($C_{3-6}$)cycloalkyl($C_{1-4}$)alkyl, ($C_{3-6}$)cycloalkyloxy or ($C_{3-6}$)cycloalkyl($C_{1-4}$)alkyloxy, means a saturated monocyclic hydrocarbon radical having from three to the number of carbon atoms designated (e.g., ($C_{3-6}$)cycloalkyl includes the radicals cyclopropyl, cyclobutyl, cyclopentyl and cyclohexyl; and ($C_{3-6}$)cycloalkyloxy includes the radicals cyclopropyloxy, cyclobutyloxy, cyclopentyloxy and cyclohexyloxy).

"Aryl", as in aryl, aryl($C_{1-4}$)alkyl, aryloxy and aryl($C_{1-4}$)alkyloxy, means an organic radical derived from an aromatic hydrocarbon containing 6 to 14 carbon atoms and includes monocyclic or condensed carbocyclic aromatic rings (e.g., phenyl, naphthyl, anthracenyl, phenanthrenyl, etc.) optionally substituted with one to two radicals independently selected from halo and cyano.

"Heteroaryl", as in heteroaryl, heteroaryl($C_{1-4}$)alkyl, heteroaryloxy and heteroaryl($C_{1-4}$)alkyloxy, means an organic radical derived from an aromatic hydrocarbon containing 5 to 14 atoms, 1 to 5 of which ring atoms are hetero atoms chosen from N, O, or S, and includes monocyclic, condensed heterocyclic and condensed carbocyclic and heterocyclic aromatic rings (e.g., thienyl, furyl, pyrrolyl, pyrimidinyl, isoxazolyl, oxazolyl, indolyl, benzo[b]thienyl, isobenzofuranyl, purinyl, isoquinolyl, pteridinyl, pyrimidinyl, imidazolyl, pyridyl, pyrazolyl, pyrazinyl, etc.) optionally substituted with one to two radicals independently selected from halo and cyano.

"Carbamoyl" means aminocarbonyl.

"Halo" means fluoro, chloro, bromo, or iodo.

"Tetramethylene" means the radical —$(CH_2)_4$—.

"Leaving group" has the meaning conventionally associated with it in synthetic organic chemistry, i.e., an atom or group displaceable under alkylating conditions, and includes halogen and alkane- or arenesulfonyloxy, such as methanesulfonyloxy, ethanesulfonyloxy, benzenesulfonyloxy and tosyloxy, and thienyloxy, dihalophosphinoyloxy, tetrahalophosphaoxy, and the like.

"Organometallic base" means a base capable of reacting with an organic compound to give a "metallated" compound of the formula R-$Met^1$ in which $Met^1$ is any monovalent electropositive metal element, typically an alkylmetallic base and preferably an alkyl alkali metal base (e.g., n-butyllithium, n-butylsodium, n-butylpotassium and the like).

"Animal" includes humans, non-human mammals, e.g., dogs, cats, rabbits, cattle, horses, sheep, goats, swine, and deer, and non-mammals, e.g., birds and the like.

"Disease" specifically includes any unhealthy condition of an animal or part thereof and includes an unhealthy condition which may be caused by, or incident to, medical or veterinary therapy applied to that animal, i.e., the "side effects" of such therapy.

"Optional" or "optionally" means that the subsequently described event or circumstance may or may not occur, and that the description includes instances where the event or circumstance occurs and instances in which it does not. For example, the phrase "which group is optionally substituted with one to three halo atoms" means that the group referred to may or may not be substituted in order to fall within the scope of the invention. "Protective group" has the meaning conventionally associated with it in synthetic organic chemistry, i.e., a group which selectively blocks one reactive site in a multifunctional compound such that a chemical reaction can be carried out selectively at another unprotected reactive site and which can be readily removed after the selective reaction is completed.

"Protective agent" means an agent which will react with a multifunctional compound and create a protective group at reactive nitrogen atoms.

"Protected" in reference to a compound or a group means a derivative of compound or group in which a reactive site or sites are blocked with protective groups.

"Deprotecting" refers to removing any protective groups present after the selective reaction has been carried out.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrobromic acid, hydrochloric acid, nitric acid, phosphoric acid, sulfuric acid and the like; or with organic acids such as acetic acid, benzenesulfonic acid, benzoic acid, camphorsulfonic acid, p-chlorobenzenesulfonic acid, cinnamic acid, citric acid, cyclopentanepropionic acid, 1,2-ethanedisulfonic acid, ethanesulfonic acid, fumaric acid, glucoheptonic acid, gluconic acid, glutamic acid, glycolic acid, hexanoic acid, heptanoic acid, o-hydroxybenzoyl) benzoic acid, 2-hydroxyethanesulfonic acid, hydroxynaphthoic acid, lactic acid, lauryl sulfuric acid, maleic acid, malic acid, malonic acid, mandelic acid, methanesulfonic acid, 4-methylbicyclo[2.2.2]oct-2-ene-1-carboxylic acid, 4,4'-methylenebis(3-hydroxy-2-ene-1-carboxylic acid), muconic acid, 2-naphthalenesulfonic acid, oxalic acid, 3-phenylpropionic acid, propionic acid, pyruvic acid, salicylic acid, stearic acid, succinic acid, tartaric acid, tertiary butylacetic acid, p-toluenesulfonic acid, trimethylacetic acid and the like.

Pharmaceutically acceptable salts also include base addition salts which may be formed when acidic protons present are capable of reacting with inorganic or organic bases. Acceptable inorganic bases include aluminum hydroxide, calcium hydroxide, potassium hydroxide, sodium carbonate and sodium hydroxide. Acceptable organic bases include diethanolamine, ethanolamine, N-methylglucamine, triethanolamine, tromethamine and the like.

"N-Oxide", when referring to a compound of Formula I, means such compound in which nitrogens are in an oxidized state, i.e., O←N. The N-oxides of compounds of Formula I can be prepared by methods known to those of ordinary skill in the art.

"Therapeutically effective amount" means that amount which, when administered to an animal for treating a disease, is sufficient to effect such treatment for the disease.

The term "q.s." means adding a quantity sufficient to achieve a stated function, e.g., to bring a solution to the desired volume (i.e., 100%).

"Treating" or "treatment" of a disease includes:
(1) preventing the disease from occurring in an animal which may be predisposed to the disease but does not yet experience or display symptoms of the disease,
(2) inhibiting the disease, i.e., arresting its development, or
(3) relieving the disease, i.e., causing regression of the disease.

Isomerism is the phenomenon wherein compounds have identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes optical isomers. A carbon atom bonded to four nonidentical substituents is termed a "chiral center".

A compound with one chiral center has two enantiomeric forms of opposite chirality and may exist as either an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture".

When one chiral center is present a stereoisomer may be characterized by the absolute configuration of that chiral center. Absolute configuration refers to the arrangement in space of the substituents attached to the chiral center. The substituents attached to the chiral center under consideration are ranked in accordance with the *Sequence Rule* of Cahn, Ingold and Prelog and the absolute descriptor R or S is cited in parentheses followed by a hyphen and the chemical name of compound.

Compounds of Formula I can exist as individual stereoisomers or mixtures of stereoisomers. For example, compounds of Formula I in which $R^5$ is a group of Formula (c) or (d) can contain chiral centers at the 5- and/or 6-positions of the 5,6-dihydro-2,4(1H,3H)-pyrimidinedione moiety. When chiral centers are present at both the 5- and 6-positions two enantiomeric pairs are possible (i.e., the 5R,6S/5S, 6R enantiomeric pair, also referred to as the cis-isomers, and the 5R,6R/5S,6S enantiomeric pair, also referred to as the trans-isomers). For the purposes of the present application when referring to a compound of Formula I by name or by formula and the configuration is not designated, it is to be understood that the reference is to all possible configurations of the compound.

The compounds of Formula I are named in accordance with acceptable nomenclature rules generally consistent with "Chemical Abstracts". For example, the compound of Formula I in which $R^1$ is methoxy and $R^2$, $R^3$ and $R^4$ are each hydro:

is named 3-{3-[4-(2-methoxyphenyl)piperazin-1-yl] propyl}-5-methyl-2,4(1H,3H)-pyrimidinedione when $R^5$ is a group of Formula (a), wherein Z is CH and $R^7$ is methyl;

is named 3-{3-[4-(2-methoxyphenyl)piperazin-1-yl] propyl}-5,6,7,8-tetrahydro-2,4(1H,3H)-quinazolinedione when $R^5$ is a group of Formula (a), wherein Z is C($R^9$) and $R^7$ and $R^9$ together are tetramethylene;

is named 4-{3-[4-(2-methoxyphenyl)piperazin-1-yl] propyl}-6-methyl-1,2,4-triazine-3,5(2H,4H)-dione when $R^5$ is a group of Formula (a), wherein Z is N and $R^7$ is methyl; and is named 3-{3-[4-(2-methoxyphenyl)piperazin-1-yl] propyl}-5,5-dimethyl-2,4,6(1H,3H,5H)-pyrimidinetrione when $R^5$ is a group of Formula (c) and each $R^8$ is methyl.

Presently Preferred Embodiments

While the broadest definition of this invention is set forth in the Summary of the Invention, certain compounds of Formula I are preferred. For example, preferred compound of Formula I are those in which $R^1$ is $(C_{1-6})$alkyloxy (optionally further substituted with one to three fluorine atoms) or heteroaryl; $R^2$ is hydro, halo, hydroxy or $(C_{1-6})$ alkyl; and $R^5$ is a group selected from Formulae (a), (b) and (c), in which $R^6$ is hydro, $(C_{1-6})$alkyl, $(C_{3-6})$cycloalkyl($C_{1-4}$)alkyl, heteroaryl($C_{1-4}$)alkyl or a group selected from benzyl and phenyl (which group is optionally further substituted with one to three radicals selected from halo, $(C_{1-6})$alkyloxy, $(C_{1-6})$alkyl and aryl) and $R^7$ is carbamoyl, cyano, halo, hydro, hydroxyiminomethyl, hydroxymethyl or $(C_{1-6})$alkyl (which alkyl is optionally substituted with one to three fluorine atoms) or together with $R^9$ is tetramethylene.

Particularly preferred compounds of Formula I are those in which $R^1$ is methoxy, ethoxy, 2,2,2-trifluoroethoxy, oxazolyl or pyrrolyl; $R^2$ is hydro, chloro, fluoro, hydroxy or methyl; and $R^5$ is a group selected from Formulae (a), (b) or (c), in which $R^6$ is hydro, methyl, cyclohexylmethyl, pyridylmethyl, pyrazinylmethyl, furylmethyl, thienylmethyl, biphenylmethyl or a group selected from benzyl and phenyl (which group is optionally further substituted with one to three radicals selected from chloro, fluoro, methyl or methoxy) and $R^7$ is carbamoyl, cyano, halo, hydro, hydroxyiminomethyl, hydroxymethyl, methyl, ethyl, propyl, trifluoromethyl or together with $R^9$ is tetramethylene; X is $CH_2$ and each of the $R^8$ radicals are hydro or X is CH(OH) and one of the $R^8$ radicals is hydroxy.

Most preferred compounds of Formula I are those in which $R^1$ is 2,2,2-trifluoroethoxy; $R^2$ is hydro, chloro, fluoro, hydroxy or methyl; $R^3$ and $R^4$ are each hydro; $R^5$ is a group of Formula (a) in which $R^7$ is hydro or methyl and Z is $C(R^9)$, wherein $R^9$ is hydro or methyl, or a group of Formula (c) in which X is CH(OH), one of the $R^8$ radicals is hydroxy and the other is methyl; and $R^6$ is hydro, methyl, cyclohexylmethyl, pyridylmethyl, pyrazinylmethyl, furylmethyl, thienylmethyl, biphenylmethyl or a group selected from benzyl and phenyl (which group is optionally further substituted with one to three radicals selected from chloro, fluoro, methyl or methoxy).

Pharmacology and Utility

The $\alpha_1$-adrenoceptor pharmacology of the compounds of this invention was determined by art-recognized procedures. In-vitro assays for measuring the relative effect of test compounds on $\alpha_1$-adrenoceptor mediated contraction of rat isolated aortic and rabbit isolated urinary bladder smooth muscle are described in Example 38. In vitro assays for measuring the relative effect of test compounds on $\alpha_1$-adrenoceptor mediated contraction of human isolated arterial, prostatic and urinary bladder smooth muscle are described in Example 39. An in vivo assay for measuring the blood pressure lowering effects of test compounds in normotensive and spontaneously hypertensive rats is described in Example 40. An in vivo assay for measuring the effect of test compounds on the reflex maintenance of basal blood pressure in response to postural change from supine to vertical is described in Example 41. An in vivo assay for measuring the relative effect of test compounds on $\alpha_1$-adrenoceptor mediated increases in blood and intraurethral pressures is described in Example 42.

In summary, the compounds of this invention were tested by the procedures described above and found to selectively inhibit the $\alpha_1$-adrenoceptors which mediate the contractile state of prostatic and lower urinary tract smooth muscle. The compounds of this invention will decrease resistance in urinary outflow, without producing the blood pressure lowering effects and/or the postural hypotension that are associated with previously described $\alpha_1$-adrenoceptor antagonists. Accordingly, the compounds of this invention are useful in treating conditions which relate directly or indirectly to obstructive uropathies, particularly obstruction due to benign prostatic hyperplasia.

Administration and Pharmaceutical Composition

In general, compounds of Formula I will be administered in therapeutically effective amounts via any of the usual and acceptable modes known in the art, either singly or in combination with another compound of Formula I or with another therapeutic agent. A therapeutically effective amount may vary widely depending on the severity of the disease, the age and relative health of the subject, the potency of the compound used and other factors. Therapeutically effective amounts of compounds of Formula I may range from 0.1 micrograms per kilogram body weight ($\mu$g/ kg) per day to 1 milligram per kilogram body weight (mg/kg) per day, typically 1 $\mu$g/kg/day to 10 $\mu$g/kg/day. Therefore, a therapeutically effective amount for a 80 kg human may range from 8 $\mu$g/day to 25 800 mg/day, typically 80 $\mu$g/day to 0.8 mg/day.

One of ordinary skill in the art of treating such diseases will be able, without undue experimentation and in reliance upon personal knowledge and the disclosure of this application, to ascertain a therapeutically effective amount of a compound of Formula I for a given disease.

In general, compounds of Formula I will be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semisolid or, in the case of an aerosol composition, gaseous excipient that is generally available to one of skill in the art:

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

Compressed gases may be used to disperse the compound of Formula I in aerosol form. Inert gases suitable for this purpose are nitrogen, carbon dioxide, nitrous oxide, etc. Other suitable pharmaceutical carriers and their formulations are described in A. R. Alfonso *Remington's Pharmaceutical Sciences* 1985, 17th ed. Easton, Pa.: Mack Publishing Company.

The amount of a compound of Formula I in the composition may vary widely depending upon the type of formulation, size of a unit dosage, kind of excipients and other factors known to those of skill in the art of pharmaceutical sciences. In general, the final composition will comprise from 0.000001% w to 10.0% w of the compound of Formula I, preferably 0.00001% w to 1.0% w, with the remainder being the excipient: or excipients.

Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 37.

Chemistry

Compounds of Formula I:

Compounds of Formula I can be prepared by the process depicted in the following Reaction Scheme I:

Scheme I

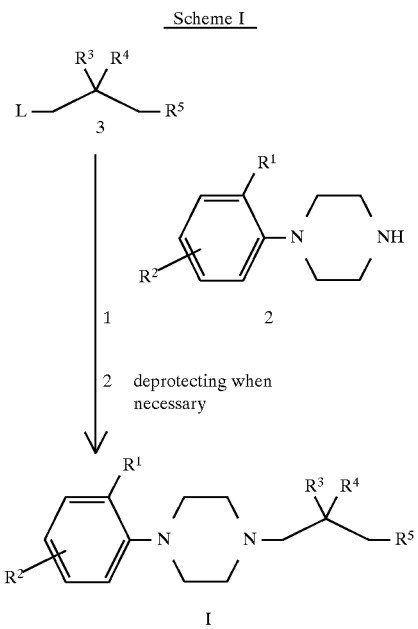

in which L is a leaving group and each $R^1$, $R^2$, $R^3$, $R^4$ and $R^5$ are as defined in the Summary of the Invention with respect Formula I.

In general, compounds of Formula I can be prepared by alkylating an optionally substituted 1-phenylpiperazine of Formula 2 with a compound of Formula 3, or a protected derivative thereof, and then deprotecting when necessary. The alkylation can be carried out neat at 100° to 250° C., typically at 150° to 200° C. and preferably at 180° to 190° C., requiring 1 to 3 hours (for further details see Example 24, infra.). Alternatively, the reaction can be carried out in a suitable inert organic solvent (e.g., acetonitrile, N,N-dimethylformamide (DMF), N-methylpyrrolidone (NMP), any appropriate mixture of suitable solvents, etc., preferably acetonitrile) with a suitable base present (e.g., sodium carbonate, potassium carbonate, cesium carbonate, 2,4,6-trimethylpyridine, etc., preferably potassium carbonate) and optionally an iodide salt present (e.g., sodium iodide, lithium iodide, tetraalkylammonium iodides such as tetramethyammonium iodide and the like, etc., preferably sodium iodide) at 40° to 90° C., typically at 70° to 85° C. and preferably at reflux, requiring 6 to 72 hours (for further details see Example 25, infra.).

Deprotection when a nitrogen protective group is present can be effected by any means which removes the protective group and gives the desired product in reasonable yield. A detailed description of the techniques applicable to protective groups and their removal can be found in T. W. Greene, *Protective Groups in Organic Synthesis*, John Wiley & Sons, Inc. 1981. For example, a convenient method of deprotection when the protective group is 2-(trimethylsilyl) ethoxymethyl is carried out with tetrabutylammonium fluoride in a suitable inert organic solvent (e.g., tetrahydrofuran (THF), hexamethylphosphoramide (HMPA), any appropriate mixture of suitable solvents, etc., preferably THF) at 10° to 65° C., typically at 20° to 25° C. and preferably at approximately 25° C., and requires 8 to 24 hours (for further details see Example 27, infra.). Deprotection when the protective group is methoxymethyl can be effected with concentrated hydrochloric acid in a suitable solvent, typically water/alcohol (9:1–1:9) mixture (e.g., water/methanol, /ethanol, /isopropanol, /any appropriate mixture of suitable alcohols, etc.) and preferably water/isopropanol (7:1), at 20° to 100° C., typically at 70° to 90° C. and preferably at approximately reflux, requiring 2 to 14 hours.

In addition, any hydroxy groups present in the compound of Formula 2 or 3 should be protected with a suitable protective group (e.g., benzyl, para-methoxybenzyl, 1-naphthylmethyl, etc., preferably benzyl). A convenient method of deprotecting a benzyl protected hydroxy group is by catalytic hydrogenation. The hydrogenation is carried out with a suitable catalyst (e.g., 10% palladium on carbon (10% Pd/C), palladium hydroxide, palladium acetate, etc. preferably 10% Pd/C) in the presence of ammonium formate and in an appropriate solvent, typically an alcohol (e.g., ethanol, methanol, isopropanol, any appropriate mixture of alcohols, etc.) and preferably methanol, at 50° to 66° C., typically at 63° to 66° C. and preferably at reflux. Alternatively, the benzyl group is removed by treating the protected compound with the catalyst under a hydrogen atmosphere at 0 to 50 psi, typically at 10 to 20 psi and preferably at approximately 15 psi, at 20° to 50° C., typically at 23° to 27° C. and preferably at 25° C.

Alternatively, compounds of Formula I in which $R^5$ can be prepared by the process depicted in the following Reaction Scheme II:

Scheme II

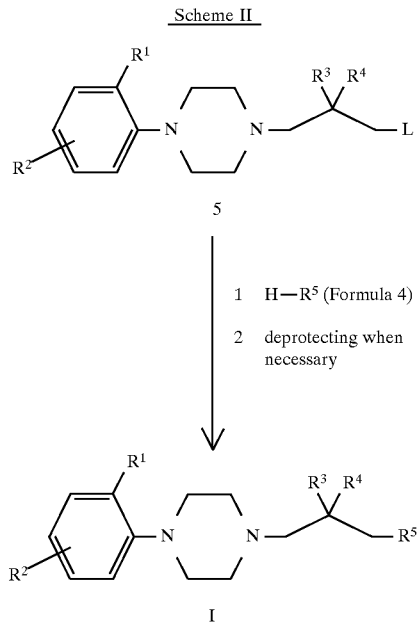

in which L is a leaving group and each $R^1$, $R^2$, $R^3$, $R^4$ and $R^5$ are as defined in the Summary of the Invention with respect Formula I.

An alternative method for preparing compounds of Formula I comprises alkylating a compound of the formula H—$R^5$ (Formula 4), or the protected derivative thereof, with a compound of Formula 5 and then deprotecting when necessary. The alkylation is carried out in the presence of a suitable base (e.g., sodium carbonate, tetrabutylammonium fluoride, benzyltrimethylammonium chloride with sodium hydroxide, tetrabutylammonium hydroxide, potassium carbonate, cesium carbonate, sodium hydride, etc., preferably potassium carbonate) and in a suitable inert organic solvent (e.g., DMF, THF, acetonitrile, mixtures of toluene and water, any appropriate mixture of suitable solvents, etc., preferably THF) at 10° to 40° C., typically at 20° to 25° C. and preferably at approximately 20° C., and requires 1 to 24 hours (for further details see Examples 30 and 31, infra.). The deprotection is carried out as set forth in Reaction Scheme I.

Alternatively, the alkylation of the compound of Formula 4 is effected by treating the compound of Formula 4 with a suitable silylating agent (e.g., 1,1,1,3,3,3-hexamethyldisilazane (HMDS), N,O-bistrimethylsilylacetamide, hexamethylsiloxane, etc., preferably HMDS) in a suitable inert organic solvent (e.g., trifluoromethanesulfonic acid, DMF, NMP, THF, DME, toluene, any appropriate mixture of suitable solvents, etc., preferably trifluoromethanesulfonic acid) at 100° to 180° C., typically at 150° to 180° C. and preferably at approximately 90° C., for 6 to 24 hours and then reacting with 1 molar equivalent of the compound of Formula 5 neat or in a suitable inert organic solvent (e.g., trifluoromethanesulfonic acid, dry benzene, toluene, 1,2-dichlorobenzene, any appropriate mixture of suitable solvents, etc., preferably trifluoromethanesulfonic acid) at 60° to 150° C., typically at 60° to 110° C. and preferably at approximately 70° C., for 0.25 to 15 hours. Proceeding as described above the following compound of Formula I was prepared: 1-(3-{4-[2-methoxyphenylpiperazin-1-yl]propyl}-5,6-dimethyl-2,4 (1H,3H)-pyrimidinedione fumarate, m.p. 216°–218° C.; Anal.: Calcd. for $C_{20}H_{28}N_4O_3 \cdot C_2H_2O_2$: C, 59.01H, 6.60; N, 11.47%; Found: C, 58.95; H, 6.61; N, 11.36%.

Compounds of Formula 2:

Compounds of Formula 2 are commercially available or can be prepared by methods known to those of ordinary skill in the art. For example, compounds of Formula 2 can be prepared by reacting a compound of Formula 6:

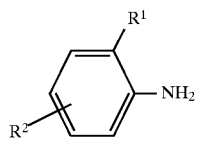

6 in which each $R^1$ and $R^2$ are as defined in the Summary of the Invention with respect to Formula I, with bis(chloroethyl)amine hydrochloride. The reaction can be carried out with a suitable base present, typically a nitrogen base (e.g., triethylamine, N,N-diisopropylethylamine, etc.) or a carbonate salt base (e.g., potassium carbonate, sodium carbonate, cesium carbonate, etc.) and preferably potassium carbonate, and optionally an iodide salt present (e.g., sodium iodide, lithium iodide, tetraalkylammonium iodides such as tetramethyammonium iodide and the like, etc., preferably sodium iodide) in a suitable inert organic solvent (e.g., n-butanol, tert-butanol, 2-methoxyethyl ether (diglyme), 2-ethoxyethanol, xylene, any appropriate mixture of suitable solvents, etc., preferably diglyme) at 110° to 170° C., typically at 140° to 165° C. and preferably at reflux, requiring 2 to 24hours (for further details see Example 13, infra.). Alternatively, the reaction can be carried out neat at 150° to 300° C., typically at 180° to 200° C. and preferably at approximately 180° C., requiring 2 to 5 hours.

Preferably, the reaction is carried out by reacting the bis(chloroethyl)amine hydrochloride with an acid addition salt of the compound of Formula 6, preferably the hydrochloride salt., in a suitable solvent (e.g., xylenes, diglyme, o-dichlorobenzene, n-hexanol, any appropriate mixture of suitable solvents, etc., preferably o-dichlorobenzene/n-hexanol (10:1)) at 140° to 180° C., typically at 160° to 180° C. and preferably at reflux, requiring 1 to 8 hours (for further details see Example 14, infra.).

Compounds of Formula 2 also can be prepared by reacting a compound of Formula 7:

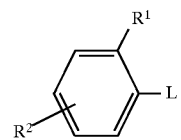

7 in which L is a leaving group, typically a halogen atom and preferably fluoro, and each $R^1$ and $R^2$ are as defined in the Summary of the Invention with respect to Formula I, with an optionally protected 1-metalated piperazine, typically a protected lithium 1-piperazinide and preferably lithium 4-benzyl-1-piperazinide, and then deprotecting. The protected 1-metalated piperazine is prepared by cooling a solution of protected piperazine in a suitable inert organic solvent, preferably an ether (e.g., THF, diethyl ether, monoglyme, diglyme, any appropriate mixture of suitable solvents, etc., preferably THF), to between −70° and 10° C., typically to between −35° to 5° C. and preferably to approximately 0° C., adding an organometallic base, typically an alkylmetallic base and preferably an alkyl alkali metal base (e.g., n-butyllithium, n-butylsodium, n-butylpotassium, etc., preferably n-butyllithium), at a rate such that the reaction temperature remains below 15° C., preferably below 5° C., and then allowing the reaction to proceed at −70° to 45° C., typically at −10° to 35° C. and preferably at approximately 25° C., for 10 minutes to 1 hour.

The reaction with the compound of Formula 7 is carried out by cooling a solution containing the 1-metalated piperazine to between −60 and 15° C., typically to between −45° and 10° C. and preferably to approximately 0° C., adding the compound of Formula 7 and then allowing the reaction to proceed at −10° to 30° C., typically at 15° to 25° C. and preferably at approximately 25° C., for 30 minutes to 48 hours. A convenient method of deprotection when the protective group is benzyl is by treating with a suitable catalyst (e.g., 10% palladium on carbon (10% Pd/C), palladium hydroxide, palladium acetate, etc. preferably 10% Pd/C) under a hydrogen atmosphere at 0 to 50 psi, typically at 10 to 20 psi and preferably at approximately 15 psi, and in an appropriate solvent, typically an alcohol (e.g., ethanol, methanol, isopropanol, any appropriate mixture of alcohols, etc.) and preferably methanol, at 20° to 50° C., typically at 23 to 27° C. and preferably at 25° C. Further details of the reaction steps set forth in this and the preceding paragraph are provided in Example 16, infra.

A convenient method for preparing a compound of Formula 2 in which $R^1$ is pyrrol-1-yl comprises reacting a protected 4-(2-aminophenyl)piperazine, preferably 4-(2-aminophenyl)piperazine-1-carbaldehyde, with 2,5-dimethoxytetrahydrofuran and then deprotecling. The reaction with the 1-carbaldehyde is carried out in a suitable solvent, typically an acid (e.g., concentrated acetic acid, propionic acid, trifluoroacetic acid, any appropriate mixture of suitable acids, etc.) and preferably concentrated acetic acid, at 100° to 150° C., typically at 110° to 120° C. and preferably at reflux, and requires 1 to 3 hours. The deprotection can be effected with a strong base (e.g., sodium hydroxide, lithium hydroxide, potassium hydroxide, any appropriate mixture of bases, etc., preferably sodium hydroxide) in a suitable solvent, typically an alcohol (e.g., ethanol, methanol, isopropanol, any appropriate mixture of alcohols, etc.) and preferably methanol, at 20° to 65° C., typically at 50° to 55° C. and preferably at approximately 50° C., requiring 3 to 6 hours.

The 4-(2-aminophenyl)piperazine-1-carbaldehyde can be prepared by reacting 1-chloro-2-nitrobenzene with piperazine-1-carbaldehyde to give 4-(2-nitro-phenyl)

piperazine-1-carbaldehyde and then reducing. The reaction between the 1-carbaldehyde and the 2-nitrobenzene is carried out in a suitable solvent (e.g., DMF, NMP, acetonitrile, any appropriate mixture of suitable solvents, etc., preferably DMF) at 50° to 100° C., typically at 60° to 80° C. and preferably at approximately 100° C., and requires 20° to 50 hours. The reduction can be effected with a suitable chemical reducing agent (e.g., nickel boride, stannous chloride, etc., preferably nickel boride) in a suitable solvent, typically an alcohol (e.g., ethanol, methanol, isopropanol, any appropriate mixture of alcohols, etc.) and preferably methanol, at 20° to 65° C., typically at 50° to 65° C. and preferably at approximately 60° C., requiring 1to 20 hours. Alternatively, the reduction can be effected under a hydrogen atmosphere at 0 to 50 psi, typically at 10 to 20 psi and preferably at approximately 15 psi, with a suitable catalyst (e.g., 10% palladium on carbon (10% Pd/C), palladium hydroxide, palladium acetate, etc. preferably 10% Pd/C) and in an appropriate solvent, typically an alcohol (e.g., ethanol, methanol, isopropanol, any appropriate mixture of alcohols, etc.) and preferably methanol, at 20° to 50° C., typically at 23° to 27° C. and preferably at 25° C., requiring 5 to 40 hours. Further details of the reaction steps set forth in this and the preceding paragraph are provided in Example 17, infra.

A convenient method for preparing a compound of Formula 2 in which $R^2$ is hydroxy comprises de-methylating a compound of Formula 2 in which $R^2$ is methoxy. The de-methylation is effected by heating in a suitable aqueous acid (e.g., aqueous hydrobromic acid, pyridine hydrochloride, any appropriate mixture of suitable acids, etc., preferably aqueous hydrobromic acid) at 100° to 200° C., typically at 120° to 140° C. and preferably at reflux, for 5 to 20 hours (for further details see Example 18, infra.).
Compounds of Formula 3:

In general, compounds of Formula 3 can be prepared by alkylating a compound of the formula H—$R^5$ (Formula 4), or a protected derivative thereof, with a compound of Formula 8:

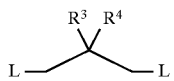

in which each L is a leaving group and $R^3$ and $R^4$ are as defined in the Summary of the Invention with respect to Formula I, and then deprotecting when necessary. The reaction is carried out in the presence of a suitable base (e.g., tetraalkylammonium halide such as tetra-n-butylammonium fluoride, tetra-n-butylammonium bromide, benzyltrimethylammonium chloride and the like, tetraalkylammonium hydroxide, tetraalkylammonium chloride with potassium hydroxide, potassium carbonate, etc., preferably tetra-n-butylammonium bromide) and in a suitable inert organic solvent (e.g., THF, DMF, acetonitrile, mixtures of toluene and water, any appropriate mixture of suitable solvents, etc., preferably DMF) at 10° to 40° C., typically at 20° to 30° C. and preferably at approximately 25° C., and requires 1 to 24 hours (for further details see Example 19, infra.). The alkylation may direct at either or both of the two secondary ring nitrogens present in the compound of Formula 3. A suitable nitrogen protective group can facilitate the direction of the alkylation. Suitable protective groups include methoxymethyl, 2-(trimethylsilyl)ethoxymethyl, tert-butyloxycarbonyl, benzyloxycarbonyl, etc., preferably methoxymethyl. Deprotection is carried out by proceeding as described above with respect to Reaction Scheme I (for further details see Example 20, infra.).

Compounds of Formula 3 in which $R^6$ is hydro can be prepared by de-benzylating the corresponding compound of Formula 3 in which $R^6$ is benzyl. The de-benzylation is carried out with ammonium formate in the presence of a palladium catalyst (e.g., 10% palladium on carbon (10% Pd/C), wet 20% palladium hydroxide on carbon, palladium black, etc., preferably 10% Pd/C) and in a suitable solvent, typically an alcohol (e.g., methanol, ethanol, 2-ethoxyethanol, any appropriate mixture of suitable alcohols, etc.) and preferably methanol, at 50° to 66° C., typically at 62° to 66° C. and preferably at reflux, and requires 3 to 96 hours (for further details see Example 21, infra.).

Compounds of Formula 3 in which $R^5$ is a group of Formula (a) wherein $R^6$ is $(C_{1-6})$alkyl, $(C_{3-6})$cycloalkyl, $(C_{3-6})$cycloalkyl$(C_{1-4})$alkyl or a group selected from aryl $(C_{1-4})$alkyl and heteroaryl$(C_{1-4})$alkyl (which aryl and heteroaryl are optionally further substituted with one to three radicals selected from halo, cyano, $(C_{1-6})$alkyloxy, $(C_{1-6})$ alkyl and aryl) can be prepared by reacting a corresponding compound of Formula 3 in which $R^6$ is hydro with 1 molar equivalent of an appropriate alkylating agent (e.g., iodomethane, benzyl bromide, 4-methylbenzyl bromide, cyclohexylmethyl bromide, pyrazin-2-ylmethyl bromide, thien-2-ylmethyl bromide, fur-3-ylmethyl bromide, biphenyl-2-ylmethyl bromide, etc.) in the presence of a suitable base (e.g., sodium carbonate, potassium carbonate, cesium carbonate, sodium hydride, etc., preferably potassium carbonate). The reaction is carried out in a suitable solvent (e.g., DMF, NMP, THF, DME, any appropriate mixture of suitable solvents, etc., preferably DMF) at 22° to 70° C., typically at 40° to 65° C. and preferably at approximately 40° C., and requires 5 to 24 hours.

Compounds of Formula 3 in which L is hydroxy and $R^3$ and $R^4$ together are ethylene can be prepared by hydrolyzing a corresponding 3- or 1-(1-cyanocycloprop-1-ylmethyl)-2,4 (1H,3H)-pyrimidinedione or 1-(1-cyanocycloprop-1-ylmethyl)-2,4,6(1H,3H,5H)-pyrimidinetrione, respectively, to give the corresponding 1-cyclopropanecarboxylic acid, reacting the carboxylic acid with methyl chloroformate to give the corresponding methoxycarbonyl carboxylate and then reducing the carboxylate. The hydrolysis can be effected by heating the nitrile with acid (e.g., concentrated hydrochloric acid, acetic acid, sulfuric acid, trifluoroacetic acid, any appropriate mixture of suitable acids, etc., typically a mixture of concentrated acetic acid and concentrated hydrochloric acid and preferably approximately 20% v/v acetic acid/concentrated hydrochloric acid) at 50° to 150° C., typically at 100° to 120° C. and preferably at reflux, for 1 to 5 hours.

Conversion of the carboxylic acid to the methoxycarbonyl carboxylate is carried out in a suitable inert organic solvent (e.g., THF, methylene chloride, 1,2-dichloroethane, ether, any appropriate mixture of suitable solvents, etc., preferably THF) under an inert atmosphere (e.g., argon, nitrogen, etc.) at −20° to 20° C., typically at 0° to 10° C. and preferably at approximately 0° C., and requires 0.2 to 2 hours. Reduction of the carboxylate can be effected with a suitable chemical reducing agent (e.g., sodium borohydride, lithium borohydride, etc., preferably sodium borohydride) at 0° to 25° C., typically at 10° to 20° C. and preferably at approximately 20° C., requiring 1 to 3 hours. Compounds of Formula 3 in which L is methanesulfonyloxy and $R^3$ and $R^4$ together are ethylene can be prepared by treating the corresponding compound of Formula 3 in which L is hydroxy with methanesulfonyl chloride in a suitable inert organic solvent (e.g., methylene chloride, dichloroethane, pyridine, any appropriate mixture of suitable solvents, etc., preferably methylene chloride) at 0° to 25° C., typically at 0° to 10° C. and preferably at approximately 0° C., requiring 0.5 to 2 hours.

The appropriate 3- and 1-(1-cyanocycloprop-1-ylmethyl)-2,4(1H,3H)-pyrimidinediones or 1-(1-cyanocycloprop-1-ylmethyl)-2,4,5(1H,3H,5H)-pyrimidinetriones are prepared by alkylating a compound of the formula H—$R^5$, or the protected derivative thereof, with 1-cyanocycloprop-1-ylmethyl methanesulfonate. The alkylation is carried out in the presence of a base (e.g., sodium hydride, potassium hydride, potassium carbonate, lithium hexamethyldisilazide, etc., preferably sodium hydride) and in a suitable inert organic solvent (e.g., DMF, THF, acetonitrile, any appropriate mixture of suitable solvents, etc., preferably DMF) at 20° to 70° C., typically at 50° to 60° C. and preferably at approximately 50° C., and requires 4 to 24 hours.

The 1-cyanocycloprop-1-ylmethyl methanesulfonate is prepared by treating 1-cyanocycloprop-1-ylmethanol with methanesulfonyl chloride in a suitable inert organic solvent (e.g., methylene chloride, dichloroethane, pyridine, any appropriate mixture of suitable solvents, etc., preferably methylene chloride) at 0° to 25° C., typically at 0° to 10° C. and preferably at approximately 0° C., requiring 0.5 to 2 hours.

The 1-cyanocycloprop-1-ylmethanol is prepared by converting 1-cyanocyclopropane-1-carboxylic acid to methoxycarbonyl 1-cyanocyclopropane-1-carboxylate and then reducing the carboxylate. The conversion of the carboxylic acid to the methoxycarbonyl carboxylate and its subsequent reduction to the corresponding alcohol are both carried out in a manner similar to that described above for preparing compounds of Formula 3 from the corresponding 1-cyclopropanecarboxylic acid. Further details of the reaction steps set forth in this and the three preceding paragraphs are provided in Example 22, infra.

The 1-cyanocyclopropane-1-carboxylic acid can be prepared by reacting 1,2-dibromoethane with ethyl cyanoacetate. The reaction is carried out in the presence of a aqueous quaternary ammonium hydroxide (e.g., triethylbenzylammonium hydroxide, tetrabutylammonium hydroxide, etc., preferably triethylbenzylammonium hydroxide) at 0° to 50° C., typically at 10° to 30° C. and preferably at approximately 22° C., requiring 0.5 to 2 hours (for further details see R. K. Singh, S. Danishefsky, *J. Org. Chem.* (1975) 40, 2969).

The N-oxides of the compounds of Formula 3 can be prepared by treating an unoxidized form of the compound of Formula 3 with an oxidizing agent (e.g., trifluoroperacetic acid, permaleic acid, perbenzoic acid, peracetic acid, 3-chloroperoxybenzoic acid, etc.) in a suitable inert organic solvent (e.g., a halogenated hydrocarbon such as methylene chloride) preferably methylene chloride) at −10° to 25° C., typically at 0° to 10° C. and preferably at approximately 0° C., requiring 1 to 14 hours (for further details see Example 23, infra).

Compounds of Formula 4:

Compounds of Formula 4 are commercially available or can be prepared by methods known to those of ordinary skill in the art. For example, compounds of Formula 4 in which $R^6$ is hydro can be prepared by reacting an acetic acid ester of the formula $R^7CH_2C(O)OR$ in which $R^7$ is as defined in the Summary of the Invention with respect to Formula I (e.g., ethyl isovalerate, methyl methoxyacetate, etc.) with ethyl formate to give a corresponding 3-oxopropionate, reacting the 3-oxopropionate with thiourea to give the corresponding 2-thioxo-4(1H,3H)-pyrimidineone and then converting the thioxopyrimidineone to the corresponding pyrimidinedione. The reaction between the acetic acid ester and ethyl formate is carried out in the presence of a suitable base (e.g., sodium, sodium hydride, potassium hydride, sodium ethoxide, etc.) in a suitable solvent (e.g., diethyl ether, ethanol, THF, any appropriate mixture of suitable solvents, etc., preferably diethyl ether) at −10° to 40° C., typically at 0° to 25° C. and preferably at approximately 10° C., requiring 20 to 90 hours. The reaction with the thiourea is carried out in a suitable solvent, typically an alcohol (e.g., ethanol, methanol, isopropanol, any appropriate mixture of alcohols, etc.) and preferably ethanol, at 20° to 100° C., typically at 50° to 80° C. and preferably at approximately 75° C., requiring 1 to 10 hours. The conversion of the thioxopyrimidineone to the pyrimidinedione is effected with aqueous acid (e.g., concentrated hydrochloric acid) in a suitable solvent (e.g., water, ethanol, DMSO, any appropriate mixture of suitable solvents, etc.) at 50° to 120° C., typically at 70° to 110° C. and preferably at approximately 100° C., and requires 2 to 12 hours (for further details see Example 2, infra.).

Compounds of Formula 4 in which $R^5$ is a group of Formula (a) wherein $R^6$ is ($C_{1-6}$)alkyl, ($C_{3-6}$)cycloalkyl, ($C_{3-6}$)cycloalkyl($C_{1-4}$)alkyl or a group selected from aryl ($C_{1-4}$)alkyl and heteroaryl($C_{1-4}$)alkyl (which aryl and heteroaryl are optionally further substituted with one to three radicals selected from halo, cyano, ($C_{1-6}$)alkyloxy, ($C_{1-6}$) alkyl and aryl) can be prepared by reacting a corresponding compound of Formula 4 in which $R^6$ is hydro with 1 molar equivalent of an appropriate alkylating agent in the presence of a suitable base. The reaction is carried out by proceeding as described above for alkylating compounds of Formula 3 in which $R^6$ is hydro (for further details see Example 5, infra.).

Alternatively, compounds of Formula 4 in which $R^5$ is a group of Formula (a) wherein $R^6$ is ($C_{1-6}$)alkyl, heterocyclo ($C_{1-4}$)alkyl, aryl($C_{1-4}$)alkyl or heteroaryl($C_{1-4}$)alkyl and certain protected derivatives of compounds of Formula 4 in which $R^5$ is a group of Formula (a) can be prepared by treating a corresponding compound of Formula 4 in which $R^6$ is hydro with a suitable silylating agent (e.g., 1,1,1,3,3,3-hexamethyldisilazane (HMDS), N,O-bistrimethylsilylacetamide, hexamethylsiloxane, etc., preferably HMDS) in a suitable inert organic solvent (e.g., trifluoromethanesulfonic acid, DMF, NMP, THF, DME, toluene, any appropriate mixture of suitable solvents, etc., preferably trifluoromethanesulfonic acid) at 100° to 180° C., typically at 150° to 180° C. and preferably at approximately 90° C., for 6 to 24 hours and then reacting with 1 molar equivalent of the alkylating agent (e.g., methoxymethyl acetate, benzyl bromide, etc.) neat or in a suitable inert organic solvent (e.g., trifluoromethanesulfonic acid, dry benzene, toluene, 1,2-dichlorobenzene, any appropriate mixture of suitable solvents, etc., preferably trifluoromethanesulfonic acid) at 60° to 150° C., typically at 60° to 110° C. and preferably at approximately 70° C., for 0.25 to 15 hours (for further details see Example 6, infra.).

Compounds of Formula 4 in which $R^5$ is a group of Formula (a) in which $R^7$ is cyano can be prepared by reacting (Z)-1-cyano-2-ethoxy-N-ethoxycarbonylacrylamide with a compound of the formula $NH_2R^6$, or a protected derivative thereof, in which $R^6$ is as defined in the Summary of the Invention with respect to Formula I. The reaction is carried out in a suitable solvent (e.g., water, ethanol, 2-methoxyethanol, any appropriate mixture of suitable solvents, etc., preferably water) at 30° to 100° C., typically at 50° to 70° C. and preferably at approximately 60° C., and requires 0.1 to 2 hours (for further details see Example 1, infra.).

Protected compounds of Formula 4 in which $R^5$ is a group of Formula (a) can be prepared by reacting a corresponding compound of Formula 4 in which $R^6$ is hydro with a suitable protecting agent (e.g., 2-(trimethylsilyl)ethoxymethyl chloride, di-tert-butyldicarbonate, etc.). For example, a protected compound of Formula 4 wherein the protective group is 2-(trimethylsilyl)ethoxymethyl can be prepared by reacting the unprotected compound with 2-(trimethylsilyl) ethoxymethyl chloride in the presence of a suitable base (e.g., diisopropylethylamine, diethylaniline, potassium carbonate, sodium hydride, etc., preferably sodium hydride) in a suitable solvent (e.g., methylene chloride, THF, DMF, NMP, etc., preferably DMF) at 0° to 30° C., typically at 20° to 30° C. and preferably at approximately 22° C., requiring 1 to 16 hours (for further details see Example 7, infra.).

A compound of Formula 4 in which $R^5$ is a group of Formula (a) wherein Z is $C(R^9)$, $R^7$ and $R^9$ together are —(CH$_2$)$_4$— and $R^9$ is hydro (i.e., 5,6,7,8-tetrahydro- 2,4 (1H,3H)-quinazolinedione) can be prepared by hydrolyzing 4-ethoxy-5,6,7,8-hexahydro-2(3H)-quinazolinone. The hydrolysis is carried out with acid (e.g., hydrochloric acid) in a suitable solvent, typically an alcohol (e.g., ethanol, methanol, isopropanol, any appropriate mixture of alcohols, etc.) and preferably ethanol, at 50° to 85° C., typically at 60° to 70° C. and preferably at approximately 65° C., and requires 0.5 to 5 hours (for further details see C. Bischoff and E. Schröder, *J. f. prakt. Chemie* 1985, 327, 129–132). The 4-ethoxy-5,6,7,8-hexahydro-2(3H)-quinazolinone is prepared by reacting ethyl 2-oxocyclohexanecarboxylate with cyanamide. The reaction with the cyanamide is carried out in a suitable solvent, typically an alcohol (e.g., ethanol, methanol, isopropanol, any appropriate mixture of alcohols, etc.) and preferably ethanol, at 25° to 100° C., typically at 50° to 80° C. and preferably at approximately 75° C., and requires 1 to 40 hours.

Compounds of Formula 4 in which $R^5$ is a group of Formula (b) can be prepared by alkylating a corresponding compound of the formula P—$R^5$ in which P is a protective group (e.g., benzyl, 2-(trimethylsilyl)ethoxymethyl, tert-butyloxycarbonyl, etc.) and $R^5$ is a group of Formula (b) wherein $R^6$ is hydro with an appropriate alkylating agent (e.g., iodomethane, benzyl bromide, 4-methylbenzyl bromide, cyclohexylmethyl bromide, pyrazin-2-ylmethyl bromide, thien-2-ylmethyl bromide, fur-3-ylmethyl bromide, biphenyl-2-ylmethyl bromide, etc.) and then deprotecting. In a similar fashion, a compound of Formula 4 in which $R^5$ is a group of Formula (b) and $R^6$ is benzyl can be prepared by alkylating a corresponding compound of Formula 4 in which $R^6$ is hydro with benzyl bromide and then deprotecting.

The alkylation is carried out with at least 2 molar equivalents of the alkylating agent in the presence of an excess amount of a suitable base (e.g., sodium carbonate, potassium carbonate, cesium carbonate, sodium hydride, etc., preferably sodium hydride) and in a suitable solvent (e.g., DMF, NMP, THF, DME, any appropriate mixture of suitable solvents, etc., preferably DMF) at 20° to 80° C., typically at 30° to 50° C. and preferably at approximately 50° C., requiring 4 to 40 hours.

The deprotection can be effected by any means which removes the protective group without removing the radical designated by $R^6$. For example, deprotection when the protective group is benzyl can be effected under conditions similar to those described above for de-benzylating a compound of Formula 3 in which $R^6$ is benzyl (for further details see Example 9, infra.). Deprotection when the protective group is 2-(trimethylsilyl)ethoxymethyl can be effected under the conditions described above for deprotecting a similarly protected compound of Formula I.

Compounds of Formula 4 in which $R^7$ is hydroxymethyl can be prepared by reacting a corresponding compound of Formula 4 in which $R^7$ is hydro with paraformaldehyde. The reaction is carried out in the presence of an aqueous base (e.g., aqueous sodium hydroxide, aqueous potassium hydroxide, etc.) at 20° to 100° C., typically at 40° to 60° C. and preferably at approximately 50° C., and requires 40 to 90 hours (for further details see Example 3, infra.).

Compounds of Formula 4 in which $R^7$ is hydroxyiminomethyl can be prepared by converting a corresponding compound of Formula 4 in which $R^7$ is hydro to a 2,4-dioxo-5(1H,3H)-pyrimidinecarbaldehyde derivative via a modified Reimer-Tiemann reaction (see Gupta, V. S. and Huennekens, F. M. (1967), *Biochemistry*, 6(7), 2168) and then reacting the carbaldehyde with hydroxylamine hydrochloride. The conversion to the carbaldehyde is carried out with chloroform in the presence of aqueous sodium hydroxide at 10° to 100° C., typically at 60° to 80° C. and preferably at reflux, and requires 0.5 to 15 hours. The reaction with the hydroxylamine hydrochloride is carried out in the presence of potassium acetate in a suitable solvent (e.g., water, methanol, 1/1 water/methanol, any appropriate mixture of suitable solvents, etc., preferable a 1/1 water/methanol) at 20° to 100° C., typically at 60° to 90° C. and preferably at reflux, and requires 0.2 to 5 hours. Further details of the reaction steps set forth above are provided in Example 4, infra.).

Compounds of Formula 4 in which $R^6$ is optionally substituted aryl or heteroaryl can be prepared by reacting a compound of Formula 4 in which $R^6$ is hydro with an appropriate alkylating agent (e.g., 1-fluoro-4-iodobenzene, bromobenzene, 2-bromopyridine, etc.) in the presence of a suitable copper source (e.g., copper(I) oxide, copper bronze, copper(I) bromide, etc., preferably copper(I) oxide) in a suitable inert organic solvent (e.g., 2,4,6-trimethylpyridine, diethylaniline, NMP, any appropriate mixture of suitable solvents, etc., preferably 2,4,6-trimethylpyridine) at 100° to 180° C., typically at 150° to 175° C. and preferably at reflux, requiring 4 to 20 hours (for further details see Example 8, infra.).

Compounds of Formula 4 in which $R^5$ is a group of Formula (c) wherein X is C(O) can be prepared by reacting a compound of the formula H$_2$NC(O)NHR$^6$ (e.g., urea, benzylurea, etc.) with an alkyl malonate of the formula (R$^8$)$_2$C(COOR)$_2$, wherein each $R^6$ and $R^8$ are as defined in the Summary of the Invention with respect to Formula I. The reaction is carried out in the presence of a base (e.g., sodium methoxide, potassium tert-butoxide, sodium hydride, etc. preferably sodium methoxide) in a suitable solvent, typically an alcohol (e.g., ethanol, methanol, isopropanol, any appropriate mixture of alcohols, etc.) and preferably methanol, at. 50° to 100° C., typically at 60° to 70° C. and preferably at reflux (for further details see Example 10, infra.).

Compounds of Formula 5:

In general, compounds of Formula 5 are prepared by reacting a compound of Formula 2 with a compound of Formula 8. The reaction is carried out in the presence of a suitable base (e.g., sodium carbonate, potassium carbonate, cesium carbonate, sodium hydride, etc., preferably potassium carbonate) and in a suitable inert organic solvent (e.g., acetonitrile, DMF, NMP, any appropriate mixture of suitable solvents, etc., preferably acetonitrile) at 50° to 85° C., typically at 70° to 80° C. and preferably at reflux, and requires 2 to 16 hours (for further details see Example 28, infra.).

Compounds of Formula 5 in which L is hydroxy and $R^3$ and $R^4$ are both methyl can be prepared by acylating a compound of Formula 2 with a protected 3-hydroxy-2,2-dimethylpropionyl halide (e.g., 3-benzyloxy-2,2-dimethylpropionyl chloride) to give the corresponding protected 3-hydroxy-2,2-dimethyl-1-(4-phenylpiperazin-1-yl)-1-propanone and then reducing and deprotecting to give the corresponding 2,2-dimethyl-3-(4-phenylpiperazin-1-yl)-1-propanol. The acylation is carried out in a suitable solvent (e.g., benzene, methylene chloride, any appropriate mixture of suitable solvents, etc.) and requires 0.1 to 6 hours at approximately 0° C. The reduction can be effected with a suitable chemical reducing agent (e.g., lithium aluminum hydride, etc.) in a suitable solvent (e.g., THF, any appropriate mixture of suitable solvents, etc.) requiring 1 to 30 hours at reflux. Deprotection when the protective group is benzyl is conveniently carried out by phase-transfer catalytic hydrogenation (e.g. ammonium formate, Pd/C; etc.) in a suitable solvent, typically an alcohol (e.g., methanol, any appropriate mixture of suitable alcohols, etc.), for 2 to 14 hours at reflux. The 1-propanol can be converted to the corresponding 1-chloro-2,2-dimethyl-3-(4-phenylpiperazin-1-yl)propane by reacting it with a suitable halogenating agent (e.g., p-toluenesulfonyl chloride, etc.) in a suitable solvent (e.g., methylene chloride, pyridine, any appropriate mixture of suitable solvents, etc.) requiring 0.1 to 12 hours at approximately 25° C.

The protected 3-hydroxy-2,2-dimethylpropionyl halide is prepared by methylating ethyl cyanoacetate to give 2-cyano-2-methylpropionic acid, reducing the propionic acid and protecting to give protected 3-hydroxy-2,2-dimethylpropanenitrile, hydrolyzing the protected 3-hydroxy-2,2-dimethylpropanenitrile to give protected 3-hydroxy-2,2-dimethylpropionic acid and then converting the propionic acid to a corresponding acid halide. The methylation can be effected with a suitable methylating agent (e.g., iodomethane, etc.) in the presence of a base (e.g., triethylbenzyl ammonium hydroxide, etc.) in a suitable solvent (e.g., water, any appropriate mixture of suitable solvents, etc.) requiring 1 to 12 hours at approximately 20° C. The reduction is carried out by reacting the propionic acid with methyl chloroformate for 0.1 to 2 hours at −5 to 0° C. and then reacting with a suitable chemical reducing agent (e.g., sodium borohydride, etc.) in a suitable solvent (e.g., THF, any appropriate mixture of suitable solvents, etc.) for 1 to 4 hours at approximately 20° C. Protecting wherein the protective group is benzyl can be effected by reacting the unprotected 3-hydroxy-2,2-dimethylpropanenitrile with benzyl bromide for 1 to 4 hours at approximately −5° C. The hydrolysis can be effected with an aqueous base (e.g., 10% sodium hydroxide, etc.) in a suitable solvent, typically an alcohol (e.g., methanol, any appropriate mixture of suitable alcohols, etc.), for 2 to 12 hours at reflux. Conversion to the acid halide can be effected with a suitable halogenating agent (e.g., oxalyl chloride, etc.) in a suitable solvent (e.g., benzene, methylene chloride, any appropriate mixture of suitable solvents, etc.) requiring 1 to 6 hours at approximately 25° C. Further details of the reaction steps set forth in this and the preceding paragraph are provided in Example 29, infra.

Compounds of Formula 6:

The compounds of Formula 6 can be prepared by reducing a corresponding nitrobenzene. The reduction can be effected with a suitable chemical reducing agent or by catalytic hydrogenation and is carried out in a manner similar to that described above for reducing 4-(2-nitrophenyl)-1-piperazinecarbaldehyde in preparing the compound of Formula 2 in which $R^1$ is pyrrol-1-yl. Nitrobenzenes suitable for preparing compounds of Formula 6 are commercially available or can be prepared by methods known to those of ordinary skill in the art. For example, suitable 2-oxynitrobenzenes can be prepared by reacting 2-fluoronitrobenzene with an appropriate alcohol (e.g., a ($C_{1-6}$)alcohol such as methanol, ethanol, 2,2,2-trifluoroethanol and the like; a ($C_{3-6}$)cycloalcohol such as cyclopropylmethanol, 2-cyclohexylethanol and the like; an arylalcohol such as phenol and the like; an aryl($C_{1-4}$)alcohol such as benzylalcohol and the like; a heteroalcohol such as 2-pyridinol and the like; a hetero($C_{1-4}$)alcohol such as 2-pyridinemethanol and the like; etc.) in the presence of a strong base (e.g., potassium tert-butoxide, sodium hydride, potassium hydride, lithium hexamethyldisilazide, etc., preferably potassium tert-butoxide). The reaction is carried out in a suitable solvent (e.g., 1,2-dimethoxyethane, THF, tert-butylmethylether, any appropriate mixture of solvents, etc., preferably 1,2-dimethoxyethane) at −30 to 30° C., typically at −20° to 20° C. and preferably at approximately −10° C., and requires 0.2 to 2 hours (for further details see Example 11, infra.).

Alternatively, suitable 2-oxynitrobenzenes can be prepared by reacting a corresponding 2-nitrophenol with a compound of the formula R—L, in which L is a leaving group (typically methanesulfonyloxy) and $R^1$ is 2-propynyl, a group selected from ($C_{1-6}$)alkyl, ($C_{3-6}$)cycloalkyl and ($C_{3-6}$)cycloalkyl($C_{1-4}$)alkyl (which group is optionally further substituted with one to three halo atoms) or a group selected from aryl($C_{1-4}$)alkyl and heteroaryl($C_{1-4}$)alkyl (which aryl and heteroaryl are optionally further substituted with one to three radicals selected from halo, cyano, ($C_{1-6}$) alkyloxy, ($C_{1-6}$)alkyl and aryl), in the presence of a suitable base, typically a nitrogen base (e.g., triethylamine, N,N-diisopropylethylamine, etc.) or a carbonate salt base (e.g., potassium carbonate, sodium carbonate, cesium carbonate, etc.) and preferably potassium carbonate, in a suitable inert organic solvent (e.g., DMF, NMP, THF, DMSO, any appropriate mixture of suitable solvents, etc., preferably DMF) at 60° to 160° C., typically at 140° to 160° C. and preferably at approximately 150° C., requiring 10 to 24 hours (for further details see Example 12, infra.).

Compounds of Formula 7:

Compounds of Formula 7 are commercially available or can be prepared by methods known to those of ordinary skill in the art. For example, a compound of Formula 7 in which L is fluoro, $R^1$ is oxazol-2-yl and $R^2$ is hydro (i.e., 2-fluoro-1-oxazol-2-ylbenzene) can be prepared by reacting 2-fluorobenzoic acid chloride with 2-bromoethylamine hydrobromide to give 2-fluoro-1-(4,5-dihydrooxazol-2-yl) benzene and then oxidizing. The reaction with the 2-bromoethylamine hydrobromide is carried out in the presence of a suitable base, typically a nitrogen base (e.g., triethylamine, N,N-diisopropylethylamine, etc., preferably triethylamine) and in a suitable solvent (e.g., benzene, methylene chloride, DMF, toluene, THF, any appropriate mixture of suitable solvents, etc., preferably benzene) at 50° to 110° C., typically at 100° to 110° C. and preferably at reflux, and requires 2 to 20 hours. The oxidation can be carried out with a suitable oxidizing agent (e.g., nickel peroxide hydrate, manganese dioxide, etc., preferably nickel peroxide hydrate) in a suitable solvent (e.g., benzene, methylene chloride, 1,2-dichloroethane, decalin, any appropriate mixture of suitable solvents, etc., preferably benzene) at 20° to 150° C., typically at 50° to 120° C. and preferably at reflux, and requires 2 to 40 hours. Further details of the process steps set forth in this paragraph are provide in Example 15, infra.

Additional Processes:

Compounds of Formula I in which $R^5$ is a group of Formula (c), wherein X is CH(OH) and one $R^8$ is cis-hydroxy, or a group of Formula (d), wherein one $R^8$ is cis-hydroxy, can be prepared by hydroxylating a corresponding compound of Formula I in which $R^5$ is a group of Formula (a) or (b), respectively, wherein Z is CH. The hydroxylation can be carried out by treating with acid (e.g., formic acid, trifluoroacetic acid, etc.) and a brominating agent such as N-bromosuccinimide, dibromantin, or a solution of bromine in water or aqueous tert-butanol, in a suitable aqueous solvent (e.g., 9:1 to 1:9 aqueous mixtures of DMSO, DMF, etc., preferably 5:1 DMSO/water) at 0° to 40° C., typically at 10° to 25° C. and preferably at approximately 20° C., requiring 4 to 24 hours, followed by neutralization to pH 7–8 by treating with a suitable aqueous base (e.g., aqueous sodium bicarbonate, potassium bicarbonate, disodium hydrogen phosphate, etc., preferably aqueous sodium bicarbonate) at –10° to 30° C., preferably at approximately 10° C. for 10 to 30 minutes (for further details see Example 35, infra, for the use of both N-bromosuccinimide and bromine in aqueous tert-butanol).

Compounds of Formula I in which $R^6$ is hydro can be prepared by de-benzylating a compound of Formula I in which $R^6$ is benzyl. The de-benzylation is carried out under conditions similar to those described above for de-benzylating a compound of Formula 3(a) in which $R^6$ is benzyl (for further details see Example 32, infra.).

Compounds of Formula I in which $R^6$ is $(C_{1-6})$alkyl, $(C_{3-6})$cycloalkyl, $(C_{3-6})$cycloalkyl$(C_{1-4})$alkyl or a group selected from aryl$(C_{1-4})$alkyl and heteroaryl$(C_{1-4})$alkyl (which aryl and heteroaryl are optionally further substituted with one to three radicals selected from halo, cyano, $(C_{1-6})$ alkyloxy, $(C_{1-6})$alkyl or aryl) can be prepared by reacting a compound of Formula I in which $R^6$ is hydro with an appropriate alkylating agent (e.g., dimethylsulfate, benzyl bromide, 4-methylbenzyl bromide, cyclohexylmethyl bromide, pyrid-2-ylmethyl chloride, 1,6-dimethylbenzyl chloride, 4-chlorobenzyl chloride, pyrazin-2-yl-methyl bromide, thien-2-ylmethyl bromide, fur-3-ylmethyl bromide, biphenyl-2-yl-methyl bromide, etc.). Typically the reaction is carried out in the presence of a suitable base (e.g., tetraalkylammonium halide such as tetrabutylammonium fluoride, benzyltrimethylammonium chloride and the like, tetraalkylammonium hydroxide, tetraalkylammonium chloride with potassium hydroxide, potassium carbonate, etc., preferably tetrabutylammonium fluoride) and in a suitable inert organic solvent (e.g., THF, DME, DMF, any appropriate mixture of suitable solvents, etc., preferably THF) at 10° to 50° C., typically at 20° to 25° C. and preferably at approximately 20° C., and requires 1 to 20 hours (for further details see Example 33, infra.).

Compounds of Formula I in which $R^6$ is optionally substituted aryl or heteroaryl can be prepared by reacting a compound of Formula I in which $R^6$ is hydro with an appropriate alkylating agent (e.g., 1-fluoro-4-iodobenzene, bromobenzene, 2-bromopyridine, etc.) in the presence of a suitable copper source (e.g., copper(I) oxide, copper bronze, copper(I) bromide, etc., preferably copper(I) oxide) in a suitable inert organic solvent (e.g., 2,4,6-trimethylpyridine, diethylaniline, NMP, any appropriate mixture of suitable solvents, etc., preferably 2,4,6-trimethylpyridine) at 100° to 180° C., typically at 150° to 170° C. and preferably at reflux, requiring 4 to 24 hours.

Compounds of Formula I in which $R^7$ is carbamoyl can be prepared by treating a compound of Formula I in which $R^7$ is cyano with acid (e.g., trifluoroacetic acid (TFA), concentrated sulfuric acid, any appropriate mixture of suitable acids, etc., preferably TFA) at 50° to 100° C., typically at 70° to 85° C. and preferably at reflux, for 0.1 to 96 hours (for further details see Example 34, infra.).

Compounds of Formula I in which $R^1$ is amino can be prepared by hydrogenating a compound of Formula I in which $R^1$ is nitro. The hydrogenation is carried out with a suitable catalyst (e.g., 10% Pd/C, palladium hydroxide, palladium acetate, etc., preferably 10% Pd/C) in a suitable alcohol solvent (e.g., ethanol, methanol, any appropriate mixture of suitable alcohols, etc., preferably ethanol) at 20° to 40° C., typically at 20° to 30° C. and preferably at approximately 25° C., and 15 to 40 psi, typically at 15 to 30 psi and preferably at approximately 15 psi, and requires 4 to 24 hours.

Compounds of Formula I in which $R^1$ is acetylamino, trifluoroacetylamino or methylsulfonylamino can be prepared by reacting a compound of Formula I in which $R^1$ is amino with acetic anhydride, trifluoroacetic anhydride or methanesulfonyl chloride, respectively. The reaction is carried out in a suitable inert organic solvent (e.g., pyridine, 2,6-dimethylpyridine, dichloromethane, triethylamine, any appropriate mixture of suitable solvents, etc., preferably pyridine) at 0° to 40° C., typically at 0° to 10° C. and preferably at approximately 0° C., and requires 0.5 to 3 hours.

Compounds of Formula I in which $R^1$, $R^2$ and/or $R^5$ is hydroxy can be prepared by demethylating a compound of Formula I in which $R^1$, $R^2$ and/or $R^5$ is methoxy. The de-methylation can be carried out with an appropriate demethylating agent (e.g., sodium cyanide, boron tribromide, boron trichloride, etc., preferably sodium cyanide) in a suitable inert organic solvent (e.g., dimethyl sulfoxide (DMSO), NMP, HMPA, methylene chloride, 1,2-dichloroethane, any appropriate mixture of suitable solvents, etc., preferably DMSO) at 80° to 180° C., typically at 100° to 160° C. and preferably at reflux, and requires 2 to 24 hours. Alternatively, the de-methylation can be effected with a suitable aqueous acid (e.g., aqueous hydrobromic acid, pyridine hydrochloride, any appropriate mixture of suitable acids, etc., preferably aqueous hydrobromic acid) at reflux, for 5 to 20 hours. Proceeding as described above the following compound of Formula I was prepared: 3-(3-{4-[4-fluoro-2-(2,2,2-trifluoroethoxy)phenyl]piperazin-1-yl}propyl)-5-hydroxy-2,4(1H,3H)-pyrimidinedione, m.p. 192–194; Anal.: Calcd. for $C_{19}H_{22}F_4N_4O_4$. $(C_2H_2O_2)_{1.5}$: C, 48.39; H, 4.55; N, 9.03%; Found: C, 48.20; H, 4.67; N, 9.18%.

Compounds of Formula I in which $R^2$ is halo can be prepared by halogenating a compound of Formula I in which $R^2$ is hydro. The halogenation can be carried out with a suitable halogenating agent (e.g., NCS, NBS, etc.) in a suitable inert organic solvent (e.g., DMF, DMSO, 1,3-dimethyl-3,4,5,6-tetrahydro-2(1H)-pyrimidinone (DMPU), NMP, any appropriate mixture of suitable solvents, etc., preferably DMF) at 0° to 100° C., typically at 20° to 6020 C. and preferably at approximately 2020 C., requiring 1 to 48 hours.

Compounds of Formula I in which $R^2$ is cyano can be prepared by cyano-de-halogenation of a compound of Formula I in which $R^2$ is halo. The reaction is carried out with copper(I) cyanide in a suitable inert organic solvent (e.g., NMP, DMPU, DMF, any appropriate mixture of suitable solvents, etc., preferably NMP) under an inert atmosphere (e.g., argon, nitrogen, etc.) at 150° to 20020 C., preferably at approximately 200° C., and requires 8 to 24 hours.

Compounds of Formula I may be prepared as pharmaceutically acceptable acid addition salts by reacting the free base forms of a compound of Formula I with a pharmaceutically acceptable inorganic or organic acid. Alternatively, the pharmaceutically acceptable base addition salts of compounds of Formula I may be prepared by reacting the free acid forms of compounds of Formula I with pharmaceutically acceptable inorganic or organic bases. Inorganic and organic acids and bases suitable for the preparation of the pharmaceutically acceptable salts of compounds of Formula I are set forth in the definitions section of this application. Alternatively, the salt forms of the compounds of Formula I may be prepared using salts of the starting materials or intermediates.

The free acid or free base forms of the compounds of Formula I can be prepared from the corresponding base addition salt or acid addition salt form. For example, compounds of Formula I in an acid addition salt form may be converted to the corresponding free base by treating with a suitable base (e.g., ammonium hydroxide solution, sodium hydroxide, etc.). Compounds of Formula I in a base addition salt form may be converted to the corresponding free acid by treating with a suitable acid (e.g., hydrochloric acid, etc).

The N-oxides of the compounds of Formula I can be prepared by treating an unoxidized form of the compound of Formula I with an oxidizing agent (e.g., trifluoroperacetic acid, permaleic acid, perbenzoic acid, peracetic acid, meta-chloroperoxybenzoic acid, etc.) in a suitable inert organic solvent (e.g., a halogenated hydrocarbon such as methylene chloride) at approximately 0° C. Alternatively, the N-oxides of the compounds of Formula I can be prepared from the N-oxide of an appropriate starting material.

Compounds of Formula I in unoxidized form can be prepared from N-oxides of compounds of Formula I by treating with a reducing agent (e.g., sulfur, sulfur dioxide, triphenylphosphine, lithium borohyciride, sodium borohydride, phosphorus trichloride, tribromide, etc.) in an suitable inert organic solvent (e.g., acetonitrile, ethanol, aqueous dioxane, eta.) at 0° to 80° C.

As will be apparent to one of ordinary skill in the art, compounds of Formula I may be prepared as individual isomers or mixtures of isomers. Isomers which are diastereomers have distinct physical properties (e.g., melting points, boiling points, solubilities, reactivity, etc.) and are readily separated by taking advantage of these dissimilarities. For example, diastereomers can be separated by chromatography (for further details see Example 35, infra) or, preferably, by separation/resolution techniques based upon differences in solubility. Optical isomers can be separated by reacting the racemic mixture with an optically active resolving agent to form a pair of diastereomeric compounds. The isomers are then separated by any of the techniques described above for the separation of diastereomers and the pure optical isomer recovered, along with the resolving agent, by any practical means that would not result in racemization. While resolution of optical isomers can be carried out using covalent diastereomeric derivatives of compounds of Formula I, dissociable complexes are preferred, e.g., crystalline diastereomeric salts. Suitable resolving acids include tartaric acid, o-nitrotartranilic acid, mandelic acid, malic acid, the 2-arylpropionic acids in general, and camphorsulfonic acid.

Individual isomers of compounds of Formula I can also be separated by such methods as direct or selective crystallization or by any other method known to one of ordinary skill in the art. A more detailed description of the techniques applicable to the resolution of stereoisomers of compounds of Formula I can be found in Jean Jacques, Andre Collet, Samuel H,. Wilen, *Enantiomers, Racemates and Resolutions*, John Wiley & Sons, Inc. (1981). Alternatively, individual isomers of compounds of Formula I can be prepared using the isomeric forms of the starting materials.

In summary, an aspect of this invention is a process for preparing a compound of Formula I:

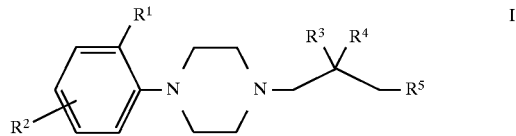

in which:

$R^1$ is acetylamino, amino, cyano, trifluoroacetylamino, halo, hydro, hydroxy, nitro, methylsulfonylamino, 2-propynyloxy, a group selected from $(C_{1-6})$alkyl, $(C_{3-6})$cycloalkyl, $(C_{3-6})$cycloalkyl$(C_{1-4})$alkyl, $(C_{1-6})$alkyloxy, $(C_{3-6})$cycloalkyloxy, $(C_{3-6})$cycloalkyl$(C_{1-4})$alkyloxy and $(C_{1-4})$alkylthio (which group is optionally further substituted with one to three halo atoms) or a group selected from aryl, aryl$(C_{1-4})$alkyl, heteroaryl, heteroaryl$(C_{1-4})$alkyl, aryloxy, aryl$(C_{1-4})$alkyloxy, heteroaryloxy and heteroaryl$(C_{1-4})$alkyloxy (which aryl and heteroaryl are optionally further substituted with one to two radicals independently selected from halo and cyano);

$R^2$ is cyano, halo, hydro, hydroxy or a group selected from $(C_{1-6})$alkyl and $(C_{1-6})$alkyloxy (which group is optionally further substituted with one to three halogen atoms);

$R^3$ and $R^4$ are both hydro or methyl or together are ethylene; and $R^5$ is a group selected from Formulae (a), (b), (c) and (d):

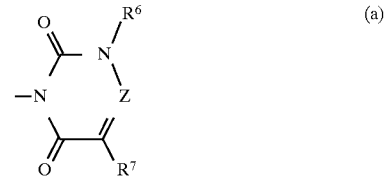

(a)

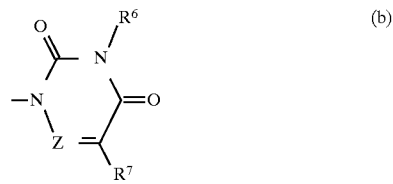

(b)

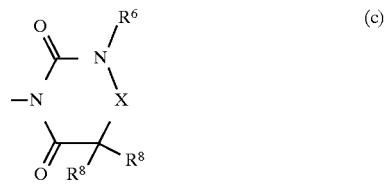

(c)

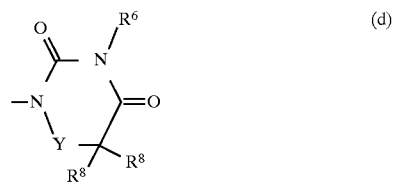

(d)

in which:

X is C(O), $CH_2$ or CH(OH);

Y is $CH_2$ or CH(OH);

Z is N or C($R^9$), wherein $R^9$ is hydro, $(C_{1-6})$alkyl or hydroxy;

R⁶ is hydro, a group selected from (C₁₋₆)alkyl, (C₃₋₆) cycloalkyl, (C₃₋₆)cycloalkyl(C₁₋₄)alkyl (which group is optionally further substituted with one to three halo atoms) or a group selected from aryl, heteroaryl, aryl(C₁₋₄)alkyl and heteroaryl(C₁₋₄)alkyl (which aryl and heteroaryl are optionally further substituted with one to three radicals selected from halo, cyano, (C₁₋₆)alkyloxy, (C₁₋₆)alkyl and aryl);

R⁷ is (C₁₋₆)alkanoyl, carbamoyl, cyano, di(C₁₋₆) alkylamino, halo, hydro, hydroxy, hydroxyiminomethyl, (C₁₋₆)alkylsulfonyl, (C₁₋₆) alkylthio, a group selected from (C₁₋₆)alkyl, (C₃₋₆) cycloalkyl, (C₁₋₆)alkyloxy and (C₁₋₆)alkyloxy(C₁₋₄) alkyl (which group is optionally further substituted with one to three radicals selected from halo, hydroxy or (C₁₋₆)alkyloxy) or a group selected from aryl, heteroaryl, aryl(C₁₋₄)alkyl and heteroaryl(C₁₋₄) alkyl (which aryl and heteroaryl are optionally further substituted with one to three radicals selected from halo, cyano, (C₁₋₆)alkyloxy, (C₁₋₆)alkyl and aryl) or R⁷ and R⁹ together are tetramethylene; and each R⁸ is independently hydro, hydroxy, methyl or ethyl; and the pharmaceutically acceptable salts and N-oxicles thereof, which process comprises:

(a) alkylating a compound of Formula 3:

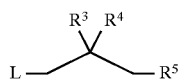

or a protected derivative thereof, in which L is a leaving group and each R³, R⁴ and R⁵ are as defined above with respect to Formula I, with a compound of Formula 2:

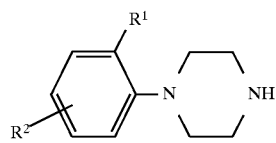

or a protected derivative thereof, in which each R¹ and R² are as defined above with respect to Formula I, and then deprotecting when necessary; or (b) alkylating a compound of the formula H—R⁵ with a compound of Formula 5:

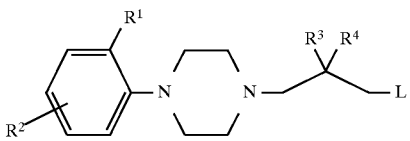

in which L is a leaving group and each R¹, R², R³ and R⁴ are as defined above with respect to Formula I; and (c) optionally further de-benzylating a compound of Formula I in which R⁶ is benzyl to give a compound of Formula I in which R⁶ is hydro;

(d) optionally further alkylating a compound of Formula I in which R⁶ is hydro to give a compound of Formula I in which R⁶ is (C₁₋₆)alkyl, (C₃₋₆)cycloalkyl, (C₃₋₆)cycloalkyl(C₁₋₄)alkyl or a group selected from aryl, heteroaryl, aryl(C₁₋₄) alkyl and heteroaryl(C₁₋₄)alkyl (which aryl and heteroaryl are optionally further substituted with one to three radicals selected from halo, cyano, (C₁₋₆)alkyloxy, (C₁₋₆)alkyl and aryl);

(e) optionally further oxidizing a compound of Formula I to give an N-oxide derivative;

(f) optionally further reducing an N-oxide derivative of a compound of Formula I to unoxidized form;

(g) optionally further converting a compound of Formula I into a pharmaceutically acceptable salt; and (h) optionally further converting a salt form of a compound of Formula I to non-salt form.

In any of the above processes, a reference to Formula I refers to such Formula wherein Z, R¹, R², R³, R⁴, R⁵, R⁶, R⁷ and R⁸ are as defined in their broadest definitions set forth in the Summary of the Invention, with the processes applying particularly well to the presently preferred embodiments.

EXAMPLES

Example 1

1-(4-Methoxybenzyl)-5-cyano-2,4(1H,3H)-pyrimidinedione

The following is the preparation of a compound of Formula 4 in which R⁵ is a group of Formula (a) wherein Z is CH, R⁶ is 4-methoxybenzyl and R⁷ is cyano.

A mixture of (Z)-1-cyano-2-ethoxy-N-ethoxycarbonylacrylamide (1 g, 4.71 mmol), 4-methoxybenzylamine (1.29 g, 9.42 mmol) and water (15 mL) was heated 10 minutes at approximately 70° C. The reaction mixture was cooled and treated with 10N hydrochloric acid (1 mL). The solids were collected, washed with water, dried in vacuo and recrystallized from ethanol/chloroform to give 1-benzyl-5-cyano-1-(4-methoxybenzyl)-2,4(1H,3H)-pyrimidinedione (788 mg, 3.06 mmol).

Example 2

5-prop-2-yl-2,4(1H,3H)-pyrimidinedione

The following is the preparation of a compound of Formula 4 in which R⁵ is a group of Formula (a) wherein Z is CH, R⁶ is hydro and R⁷ is prop-2-yl.

A suspension of sodium (2.84 g, 123.5 mmol) in dry diethyl ether (27 mL) was cooled to 0° C. and a mixture of ethyl isovalerate (23.04 mL, 153 mmol), ethyl formate (16.65 mL, 206 mmol) and dry diethyl ether (19 mL) was added dropwise. The mixture was cooled 48 hours at 0° C. and allowed to stand 24 hours at 25° C. and then concentrated in vacuo. The residue was stirred 7 hours at reflux with thiourea (5.95 g, 78 mmol) and absolute ethanol (44 mL). The mixture was concentrated and the residue was dissolved in water (40 mL). The solution was washed with diethyl ether, treated with concentrated hydrochloric acid and cooled to 0° C. The solids were collected and recrystallized from ethanol. The crystals were suspended in 10%; aqueous chloroacetic acid (11 mL) and the suspension was heated 8 hours at reflux and then cooled. The solids were collected and recrystallized from ethanol to give 5-prop-2-yl-2,4(1H, 3H)-pyrimidinedione, m.p. 284°–286° C.

Proceeding as in Example 2, but substituting methyl methoxyacetate for ethyl isovalerate gave 5-methoxy-2,4 (1H,3H)-pyrimidinedione.

Example 3

5-Hydroxymethyl-2,4(1H,3H)-pyrimidinedione

The following is the preparation of a compound of Formula 4 in which R⁵ is a group of Formula (a) wherein which Z is CH, R⁶ is hydro and R⁷ is hydroxymethyl.

A mixture of uracil (9 g, 80.3 mmol), paraformaldehyde (3 g) and 0.42N potassium hydroxide (125 mL) was heated 90 hours at 50° C. The reaction mixture was diluted with water (350 mL), stirred with Dowex® 50 ion-exchange resin (30 g, H form, 100–200 mesh), filtered, concentrated in vacuo to a volume of 20 mL and refrigerated. The solids were collected and recrystallized from water (50 mL) to give 5-hydroxymethyl-2,4(1H,3H)-pyrimidinedione (9.5 g, 65.04 mmol), m.p. 260°–300° C. (dec).

Example 4
5-Hydroxyiminomethyl-2.4(1H,3H)-pyrimidinedione

The following is the preparation of a compound of Formula 4 in which $R^5$ is a group of Formula (a) wherein Z is CH, $R^6$ is hydro and $R^7$ is hydroxyiminomethyl.

A mixture of uracil (6 g, 53.5 mmol), 50% sodium hydroxide (12 mL, 150 mmol) and chloroform (5 mL) was heated at reflux and additional chloroform (20 mL) was added over 15 minutes. The mixture was heated 4 hours at reflux and then concentrated at 50° C. using a water aspirator. The residue was dissolved in water (5 mL) and the solution was treated with 5N hydrochloric acid. The solution was chromatographed on Dowex® 50 eluting with water to give gave 2,4-dioxo-5(1H,3H)-pyrimidinecarbaldehyde (1.79 g, 11.2 mmol).

A mixture of 2,4-dioxo-5(1H,3H)-pyrimidinecarbaldehyde (1.79 g, 12.8 mmol), methanol (35 mL) and water (35 mL) was heated at reflux and then a mixture of hydroxylamine hydrochloride (905 mg, 13 mmol), potassium acetate (1.28 g, 13 mmol) and water (15 mL) was added. The mixture was cooled and the solids were collected, washed with water and recrystallized from water/methanol to give 5-hydroxyiminomethyl-2,4(1H,3H)-pyrimidinedione (1.68 g, 10.8 mmol).

Example 5
1-Benzyl-5-methyl-2,4(1H,3H)-pyrimidinedione

The following is the preparation of a compound of Formula 4 in which $R^5$ is a group of Formula (a) wherein Z is CH, $R^6$ is benzyl and $R^7$ is methyl.

A mixture of thymine (7.68 g, 61 mmol), benzyl bromide (10.55 g, 61 mmol), potassium carbonate (17.05 g, 123 mmol) and DMF (90 mL) was stirred 12 hours at 25° C. The reaction mixture was poured into water (500 mL) and extracted with ethyl acetate (3×200 mL). The combined extract was washed with water (5×100 mL), dried ($Na_2SO_4$) and concentrated in vacuo. The residue was crystallized from hexane/ethyl acetate to give 1-benzyl-5-methyl-2,4 (1H,3H)-pyrimidinedione (9.4 g, 43.9 mmol), m.p. 170°–173° C.

Proceeding as in Example 5, but substituting a different starting material for benzyl bromide and/or 5-methyl-2,4 (1H,3H)-pyrimidinedione gave the following compounds of Formulae 3 and 4:
substituting 3-(3-chloropropyl)-5-methyl-2,4(1H,3H)-pyrimidinedione and pyrid-4-ylmethyl chloride gave 3-(3-chloropropyl)-5-methyl-1-pyrid-4-ylmethyl-2,4(1H, 3H)-pyrimidinedione;
substituting 5-ethyl-2,4(1H,3H)-pyrimidinedione gave 1-benzyl-5-ethyl-2,4(1H,3H)-pyrimidinedione, m.p. 154°–155° C.;
substituting 5-propyl-2,4(1H,3H)-pyrimidinedione gave 1-benzyl-5-propyl-2,4(1H,3H)-pyrimidinedione;
substituting 5-trifluoromethyl-2,4(1H,3H)-pyrimidinedione gave 1-benzyl-5-trifluoromethyl-2,4(1H,3H)-pyrimidinedione, m.p. 194°–195° C.;
substituting 6-methyl-1,2,4-triazine-3,5(2H,4H)-dione gave 4-benzyl-6-methyl-1,2,4-triazine-3,5(2H,4H)-dione, m.p. 143°–146° C.;
substituting 2,4-dioxo-5(1H,3H)-pyrimidinecarbaldehyde gave 1-benzyl-2,4-dioxo-5(1H,3H)-pyrimidinecarbaldehyde;
substituting 6-cyano-5-methyl-2,4(1H,3H)-pyrimidinedione gave 1-benzyl-6-cyano-5-methyl-2,4(1H,3H)-pyrimidinedione;
substituting 2,4(1H,3H)-pyrimidinedione gave 1-benzyl-2,4 (1H,3H)-pyrimidinedione;
substituting 4-methoxybenzyl bromide gave 1-(4-methoxybenzyl)-5-methyl-2,4(1H,3H)-pyrimidinedione;
substituting 2,4-dimethylbenzyl bromide gave 1-(2,4-dimethylbenzyl)-5-methyl-2,4(1H,3H)-pyrimidinedione;
substituting 2-methylbenzyl bromide gave 1-(2-methylbenzyl)-5-methyl-2,4(1H,3H)-pyrimidinedione;
substituting biphenyl-3-ylmethyl bromide gave 1-biphenyl-3-ylmethyl-5-methyl-2,4(1H,3H)-pyrimidinedione;
substituting cyclohexylmethyl bromide gave 1-cyclohexylmethyl-5-methyl-2,4(1H,3H)-pyrimidinedione;
substituting pyrazin-2-ylmethyl chloride gave 1-pyrazin-2-ylmethyl-5-methyl-2,4(1H,3H)-pyrimidinedione;
substituting pyrid-4-ylmethyl chloride gave 1-pyrid-4-ylmethyl-5-methyl-2,4(1H,3H)-pyrimidinedione;
substituting pyrid-3-ylmethyl chloride gave 1-pyrid-3-ylmethyl-5-methyl-2,4(1H,3H)-pyrimidinedione;
substituting fur-2-ylmethyl chloride gave 1-fur-2-ylmethyl-5-methyl-2,4(1H,3H)-pyrimidinedione;
substituting fur-3-ylmethyl chloride gave 1-fur-3-ylmethyl-5-methyl-2,4(1H,3H)-pyrimidinedione;
substituting thien-2-ylmethyl chloride gave 1-thien-2-ylmethyl-5-methyl-2,4(1H,3H)-pyrimidinedione; and
substituting methyl iodide gave 1,5-dimethyl-2,4(1H,3H)-pyrimidinedione.

Example 6
1-Methoxymethyl-5-methyl-2,4(1H,3H)-pyrimidinedione

The following is the preparation of a protected derivative compound of Formula 4 in which $R^5$ is a group of Formula (a) wherein Z is $C(CH_3)$, $R^7$ is methyl and the protective group is methoxymethyl.

A mixture of thymine (100 g, 0.79 mol), trifluoromethanesulfonic acid (2 mL, 20 mmol) and HMDS (418 mL, 1.98 mol) was heated 16 hours with stirring at 90° C. and briefly at reflux and then distilled in vacuo at 80° C. to remove the excess HMDS. The mixture was treated with trifluoromethanesulfonic acid (1.5 mL, 20 mmol) and then methoxymethyl acetate (88 mL, 0.89 mol) was added at a rate such that the reaction temperature did not exceed 95° C. The mixture was heated 20 minutes at 70° C. and then distilled in vacuo to remove the trimethysilyl acetate formed as byproduct. The reaction mixture was poured into isopropanol (800 mL) and stirred 18 hours. The solids were collected, washed with ethyl acetate and dried to give 1-methoxymethyl-5-methyl-2,4(1H,3H)-pyrimidinedione (116 g, 0.68 mol).

Proceeding similarly as in Example 5, but substituting different starting materials for thymine and/or methoxymethyl acetate, gave the following compounds of Formula 4:
substituting 5,6-dimethyl-2,4(1H,3H)-pyrimidinedione and benzyl bromide gave 1-benzyl-5,6-dimethyl-2,4(1H,3H)-pyrimidinedione, m.p. 187°–189° C.;
substituting 5-methoxymethyl-2,4(1H,3H)-pyrimidinedione and benzyl bromide gave 1-benzyl-5-methoxymethyl-2,4 (1H,3H)-pyrimidinedione, m.p. 134°–136° C.;
substituting 6-methyl-2,4(1H,3H)-pyrimidinedione and benzyl bromide gave 1-benzyl-6-methyl-2,4(1H,3H)-pyrimidinedione, m.p. 228°–230° C.;
substituting 5-hydroxyiminomethyl-2,4(1H,3H)-pyrimidinedione and benzyl bromide gave 1-benzyl-5-hydroxyiminomethyl-2,4(1H,3H)-pyrimidinedione, m.p. 172°–174° C.; and substituting 2,2,2-trifluoroethyl p-toluenesulfonate gave 1-(2,2,2-trifluoroethoxy)-5-methyl-2,4(1H,3H)-pyrimidinedione.

Example 7
1-[2-(Trimethylsilyl)ethoxymethyl]-2,4(1H,3H)-pyrimidinedione

The following is a of the preparation of a protected compound of Formula 4 in which $R^5$ is a group of Formula (a) wherein Z is CH, $R^7$ is hydro and the protective group is 2-(trimethylsilylethoxy)methylbenzyl.

A solution of 60% sodium hydride (2 g, 50 mmol) in mineral oil was washed with hexanes (2×20 mL) and cooled to 0° C. The solution was diluted with DMF (200 mL) and then uracil (5.6 g, 50 mmol) was added portionwise over 30 minutes. The mixture was treated with 2-(trimethylsilyl) ethoxymethyl chloride (8.8 mL, 50 mmol) and allowed to warm to 25° C. and stand 4 hours. The reaction mixture was diluted with water (500 mL) and extracted with diethyl ether (4×100 mL). The combined extract was washed with brine, dried ($Na_2SO_4$), filtered and concentrated. The residue was purified by chromatography on silica gel eluting with hexanes/ethyl acetate (2:1) to give 1-[2-(trimethylsilyl) ethoxymethyl]-2,4(1H,3H)-pyrimidinedione (1.8 g, 7.4 mmol), M.p. 120°–122° C.

Proceeding as in Example 7, but a different starting material for uracil and/or 2-(trimethylsilyl)ethoxymethyl chloride gave the following protected compounds of Formula 4:

substituting 5-prop-2-yl-2,4(1H,3H)pyrimidinedione and di-tert-butyl dicarbonate gave tert-butyl 5-prop-2-yl-2,4-dioxo-(1H,3H)-1-pyrimidinecarboxylate;

substituting 5-methylthio-2,4(1H,3H)pyrimidinedione and di-tert-butyl dicarbonate gave tert-butyl 5-methylthio-2,4-dioxo-(1H,3H)-1-pyrimidinecarboxylate;

substituting 5-fur-2-yl-2,4(1H,3H)pyrimidinedione and di-tert-butyl dicarbonate gave tert-butyl 5-fur-2-yl-2,4-dioxo-(1H,3H)-1-pyrimidinecarboxylate;

substituting 5-methoxy-2,4(1H,3H)-pyrimidinedione gave 1-[2-(trimethylsilyl)ethoxymethyl]-5-hydroxymethyl-2,4 (1H,3H)-pyrimidinedione; and substituting 5-hydroxymethyl-2,4(1H,3H)-pyrimidinedione gave 1-[2-(trimethylsilyl)ethoxymethyl]-5-hydroxymethyl-2,4(1H,3H)-pyrimidinedione.

Example 8
1- and 3-(4-Fluorophenyl)-5-methyl-2,4(1H3H)-pyrimidinedione

The following is the preparation of a compound of Formula 4 in which $R^5$ is a group of Formula (a) wherein Z is CH, $R^6$ is 4-fluorophenyl and $R^7$ is methyl and a compound of Formula 4 in which $R^5$ is a group of Formula (b) wherein Z is CH, $R^6$ is 4-fluorophenyl and $R^7$ is methyl.

A mixture of thymine (5 g, 39.6 mmol), 1-fluoro-4-iodobenzene (9.68 g, 5 mL, 43.6 mmol), copper(I) oxide (6.24 g, 43.6 mmol) and 2,4,6-trimethylpyridine (200 mL) was heated 12 hours at reflux with stirring and under an argon atmosphere. The reaction mixture then was cooled to 25° C., diluted with methylene chloride (300 mL), washed with 5% sulfuric acid (5×300 mL) and concentrated. The residue was purified by flash chromatography on silica gel eluting with hexane/ethyl acetate (1:1) to give 1-(4-fluorophenyl)-5-methyl-2,4(1H,3H)-pyrimidinedione (1.85 g, 9.2 mmol), m.p. 212°–214° C., and 3-(4-fluorophenyl)-5-methyl-2,4(1H,3H)-pyrimidinedione (2.39 g, 10.2 mmol), m.p. 229°–231° C.

Proceeding as in Example 8, but substituting bromobenzene for 1-fluoro-4-iodobenzene gave 5-methyl-1-phenyl-2, 4(1H,3H)-pyrimidinedione, m.p. 200°–202° C., and 5-methyl-3-phenyl-2,4(1H,3H)-pyrimidinedione, m.p. 258°–260° C.

Example 9
3-Benzyl-5-methyl-2,4(1H,3H)-pyrimidinedione

The following is the preparation of a compound of Formula 4 in which $R^5$ is a group of Formula (b) wherein Z is CH, $R^6$ is benzyl and $R^7$ is methyl.

A mixture of 1,3-dibenzyl-5-methyl-2,4(1H,3H)-pyrimidinedione (2 g, 6.5 mmol), 5% palladium on carbon (3 g) and 0.4N ammonium formate (250 mL in methanol) was heated 1.5 hours at reflux. The reaction mixture then was filtered and concentrated in vacuo. The residue was purified by column chromatography on silica gel eluting with methylene chloride/methanol (95:5) to give 3-benzyl-5-methyl-2,4(1H,3H)-pyrimidinedione, m.p. 208°–210° C.

Proceeding as in Example 9, but substituting different starting materials for 1,3-dibenzyl-5-methyl-2,4(1H,3H)-pyrimidinedione, the following compounds of Formula 4 were prepared:

substituting 2,4-dibenzyl-6-methyl-1,2,4-triazine-3,5(2H, 4H)-dione gave 2-benzyl-6-methyl-1,2,4-triazine-3,5(2H, 4H)-dione, m.p. 141°–142° C.;

substituting 1,3-dibenzyl-5,6-dimethyl-2,4(1H,3H)-pyrimidinedione gave 3-benzyl-5,6-dimethyl-2,4(1H,3H)-pyrimidinedione; and substituting 1,3-dibenzyl-6-methyl-2,4(1H,3H)-pyrimidinedione gave 3-benzyl-6-methyl-2,4(1H,3H)-pyrimidinedione.

Example 10
1-Benzyl-5,5-dimethyl-2,4,6(1H,3H,5)-pyrimidinetrione

The following is the preparation of a compound of Formula 4 in which $R^5$ is a group of Formula (c) wherein X is C(O), $R^6$ is benzyl and each $R^8$ is methyl.

A mixture of sodium methoxide (0.343 g, 14.9 mmol), benzylurea (1.6 g, 10.6 mmol), diethyl dimethylmalonate (1.9 g, 10 mmol) and methanol (15 mL) was heated 6 hours at reflux. The reaction mixture was concentrated and the residue was stirred with water (30 mL) at 5° C. and then hydrochloric acid was added. The solids were collected, washed with water and dried to give 1-benzyl-5,5-dimethyl-2,4,6(1H,3H,5H)-pyrimidinetrione, m.p 136°–137° C.

Example 11
4-Fluoro-2-(2,2,2-trifluoroethoxy)aniline

The following is the preparation of a compound of Formula 6 in which $R^1$ is 2,2,2-trifluoromethoxy and $R^2$ is fluoro at the 4-position.

A solution of trifluoroethanol (88 g, 64 mL, 88 mol) was added to a slurry of potassium tert-butoxide (98.8 g, 0.88 mol) in 1,2-dimethoxyethane (145 mL) such that the reaction temperature remained below 11° C. The mixture then was cooled 1.5 hours at 0° to 5° C. and added over 2.5 hours to a solution of 2,4-difluoronitrobenzene (135 g, 0.85 mol) in 1,2-dimethoxyethane (150 mL) at −10° C. The mixture was cooled 1 hour at −10° C. and then aqueous potassium dihydrogen phosphate solution (13 g, 130 mL) was added. The mixture was warmed to 25° C. and solid potassium dihydrogen phosphate (7 g) was added. The mixture was diluted with methyl tert-butyl ether (600 mL) and water (300 mL) and the organic layer was separated, diluted with methyl tert-butyl ether (100 mL), washed with water (2×400 mL), filtered through Celite (2 g) and concentrated in vacuo to give 4-fluoro-2-(2,2,2-trifluoroethoxy)nitrobenzene (13 g, 57.2 mmol)

A slurry of 20% palladium hydroxide on carbon (30 mg) in ethyl acetate (3 mL) was hydrogenated 17 hours with stirring and then a solution of 4-fluoro-2-(trifluoroethoxy) nitrobenzene (3 g, 13 mmoL) in ethyl acetate (6 mL) was added. The mixture was hydrogenated 16 hours with stirring, filtered on celite, washed with ethyl acetate (10 mL), diluted with 4.3M hydrogen chloride (3 mL, 13 mmol in isopropanol) and concentrated in vacuo. The residue was taken up in ethyl acetate (25 mL) and the slurry was concentrated, diluted with ethyl acetate (25 mL), reconcentrated and diluted with ethyl acetate (5 mL). The slurry was stirred 17 hours, diluted with ethyl acetate (10 mL) and stirred 5 hours. The solids were collected, washed with ethyl acetate (3 mL) and dried in vacuo at 60° C. to give 4-fluoro-2-(2,2,2-trifluoroethoxy)aniline hydrochloride (2.5 g, 10.4 mmol), m.p. 203°–204° C.

Example 12

2-(2,2,2-Trifluoroethoxy)aniline

The following is the preparation of a compound of Formula 6 in which $R^1$ is 2,2,2-trifluoromethoxy and $R^2$ is hydro.

A mixture of 2-nitrophenol (18.8 g, 135 mmol), 2,2,2-trifluoroethyl para-toluenesulfonate (34.36 g, 135 mmol), potassium carbonate (18.7 g, 135 mmol) and DMF (200 mL) was heated 16 hours at 140° C. The reaction mixture then was cooled, diluted with water (600 mL) and extracted with ether/hexanes (1:1; 3×400 mL). The combined extracts were washed with saturated sodium bicarbonate (3×100 mL) and brine, dried ($Na_2SO_4$), filtered and concentrated to give 1-(2,2,2-trifluoroethoxy)-2-nitrobenzene (27 g, 117 mmol) as an oil.

A mixture of 1-(2,2,2-trifluoroethoxy)-2-nitrobenzene (15 g, 68 mmol), platinum oxide hydrate (100 mg) and absolute ethanol (80 mL) was hydrogenated 18 hours with stirring at 25° C. and 15 psi of pressure. The reaction mixture then was filtered and concentrated. The residue was purified by column chromatography on silica gel eluting with hexane/ethyl acetate (9:1) to give 2-(2,2,2-trifluoroethoxy)aniline (10.4 g, 54.5 mol), m.p. 49°–50° C.

Example 13

1-[2-(2.2.2-Trifluoroethoxy)phenyl]piperazine

The following is the preparation of a compound of Formula 2 in which $R^1$ is 2,2,2-trifluoroethoxy and $R^2$ is hydro.

A mixture of 2-(2,2,2-trifluoroethoxy)aniline (2.85 g, 14.9 mmol), bis(2-chloroethyl)amine hydrochloride (2.66 g, 14.9 mmol), potassium carbonate (2.06 g, 14.9 mmol), sodium iodide (0.45 g, 3 mmol) and bis(2-methoxyethyl) ether (7.3 mL) was heated 8 hours at reflux. The reaction mixture then was cooled, treated with concentrated ammonium hydroxide, poured into water (30 mL) and extracted with ethyl acetate (3×30 mL). The combined extracts were washed with water (2×30 mL) and brine (1×30 mL), dried ($MgSO_4$) and concentrated in vacuo. The residue was purified by column chromatography on silica gel eluting with methylene chloride/methanol (95:5) to give 1-[2-(2,2,2-trifluoroethoxy)phenyl]piperazine (2.93 g, 11.2 mmol), m.p. 107°–108° C.

Proceeding as in Example 13, but substituting different starting materials for 2-(2,2,2-trifluoroethoxy)aniline the following-compounds of Formula 2 were prepared:

substituting 4-chloro-2-methoxyaniline gave 1-(4-chloro-2-methoxyphenyl)-piperazine as an oil;

substituting 4-chloro-2-(2,2,2-trifluoroethoxy)aniline gave 1-[4-chloro-2-(2,2,2-trifluoroethoxy)phenyl]piperazine as a foam;

substituting 4-fluoro-2-(2,2,2-trifluoroethoxy)aniline and recrystallizing from a solution of hydrochloric acid in alcohol gave 1-[4-fluoro-2-(2,2,2-trifluoroethoxy)phenyl]piperazine hydrochloride 206°–20° C.;

substituting 5-fluoro-2-methoxyaniline gave 1-(5-fluoro-2-methoxyphenyl)piperazine, m.p. 181°–183° C.;

substituting 4-fluoro-2-ethoxyaniline gave 1-(4-fluoro-2-ethoxyphenyl)piperazine as an oil;

substituting 2-(trifluoromethoxy)aniline gave 1-(2-trifluoromethoxyphenyl)piperazine as an oil;

substituting 4-fluoro-2-methoxyaniline and recrystallizing from a solution of hydrochloric acid in alcohol gave 1-(4-fluoro-2-methoxyphenyl)piperazine hydrochloride, m.p. 202°–204° C.;

substituting 5-chloro-2-methoxyaniline gave 1-(5-chloro-2-methoxyphenyl)piperazine;

substituting 5-chloro-2-(2,2,2-trifluoroethoxy)aniline gave 1-[5-chloro-2-(2,2,2-trifluoroethoxy)phenyl]piperazine;

substituting 2-aminobiphenyl gave 1-biphenyl-2-ylpiperazine as an oil;

substituting 4-methyl-2-(2,2,2-trifluoroethoxy)aniline and recrystallizing from a solution of hydrochloric acid in alcohol gave 1-[4-methyl-2-(2,2,2-trifluoroethoxy)phenyl]piperazine, m.p. 215° C. (dec);

substituting 4-methoxy-2-(2,2,2-trifluoroethoxy)aniline gave 1-[4-methoxy-2-(2,2,2-trifluoroethoxy)phenyl]piperazine;

substituting 2-trifluoromethylaniline gave 1-(2-trifluoromethylphenyl)piperazine;

substituting 2-n-propylaniline gave 1-(2-n-propylphenyl) piperazine, m.p. 213°–215° C.;

substituting 2-neopentoxyaniline gave 1-(2-neopentoxyphenyl)piperazine;

substituting 2-(2-propynyloxy)aniline gave 1-[2-(2-propynyloxy)phenyl]piperazine;

substituting 2-cyclopropylaniline gave 1-(2-cyclopropylphenyl)piperazine dihydrochloride, m.p. 124°–133° C.;

substituting 2-benzylaniline gave 1-(2-benzylphenyl) piperazine;

substituting N-(2-aminophenyl)acetamide gave N-(2-piperazin-1-ylphenyl)acetamide;

substituting N-(2-aminophenyl)trifluoroacetamide gave N-(2-piperazin-1-ylphenyl)trifluoroacetamide;

substituting 4-methyl-2-methoxyaniline gave 1-(4-methyl-2-methoxyphenyl)piperazine, m.p. 207°–224° C.;

substituting 2-bromo-4-fluoroaniline gave 1-(2-bromo-4-fluorophenyl)piperazine;

substituting 2,4-di(2,2,2-trifluoroethoxy)aniline gave 1-[2,4-di(2,2,2-trifluoroethoxy)phenyl]piperazine; and substituting 2-(2,2,2-trifluoroethoxy)-2-methylaniline gave 1-[2-(2,2,2-trifluoroethoxy)-4-methylphenyl]piperazine.

Example 14

1-[4-Fluoro-2-(2,2,2-trifluoroethoxy)phenyl]piperazine

The following is the preparation of a compound of Formula 2 in which $R^1$ is 2,2,2-trifluoroethoxy and $R^2$ is fluoro at the 4-position.

A mixture of bis(2-chloroethyl)amine hydrochloride (14.3 g, 80 mmol), 2-(4-fluoro-2,2,2-trifluoroethoxyaniline hydrochloride (20 g, 81 mmol), prepared as in Example 11, o-dichlorobenzene (40 mL) and n-hexanol (4 mL) was heated 4 hours at reflux. The reaction mixture was allowed to cool to 80° C., then slowly diluted with ethyl acetate (100 mL) and allowed to cool to 25° C. The solids were collected, washed with ethyl acetate (20 mL) and dried in vacuo at 60° to 65° C. to give 1-[4-fluoro-2-(2,2,2-trifluoroethoxy) phenyl]piperazine dihydrochloride (20.1 g, 56.4 mmol), m.p. 208°–210° C.

Example 15
2-Fluoro-1-oxazol-2-ylbenzene

The following is the preparation of a compound of Formula 7 in which L is fluoro, $R^1$ is oxazol-2-yl and $R^2$ is hydro.

A mixture of 2-fluorobenzoic acid (4.5 g, 32.14 mmol), oxalyl chloride (4.1 mL, 48.2 mL), DMF (2 drops) and methylene chloride (40 mL) was heated 2 hours at reflux. The reaction mixture was allowed to cool to 25° C., then stirred approximately 12 hours and concentrated. The residue was slowly added to a suspension of 2-bromoethylamine hydrobromide (5.7 g, 28 mmol), triethylamine (21 mL, 160 mmol) and benzene (200 mL). The mixture was heated 12 hours at reflux, allowed to cool to 25° C., stirred an additional 12 hours and diluted with water. The aqueous layer was separated and extracted with methylene chloride (2×50 mL). The combined extracts were dried (MgSO$_4$) and concentrated. The residue was purified on silica gel by column chromatography eluting with hexanes/ethyl acetate (5:1) to give 2-fluoro-1-(4,5-dihydrooxazol-2-yl)benzene (1.96 g, 11.9 mmol).

A mixture of 2-fluoro-1-(4,5-dihydrooxazol-2-yl)benzene (4.5 g, 27.3 mmol), nickel peroxide hydrate (7 g) and benzene (40 mL) was heated 24 hours at reflux. The reaction mixture was allowed to cool to 25° C., then filtered and concentrated by rotary evaporation. The residue was purified on silica gel by column chromatography eluting with hexanes/ethyl acetate (5:1) to give 2-fluoro-1-oxazol-2-ylbenzene (0.5 g, 3.07 mmol).

Example 16
1-(2-Oxazol-2-ylphenyl)piperazine

The following is the preparation of a compound of Formula 2 in which $R^1$ is oxazol-2-yl and $R^2$ is hydro.

A mixture of N-benzylpiperazine (3.56 g, 20.2 mmol) and THF (25 mL) was cooled to 0° C. and n-butyllithium (2.5M in hexanes, 7.6 mL, 19 mmol) was added. The mixture was cooled 30 minutes with stirring at 0° C., stirred 1 hour at 25° C., then cooled to 0° C. and 2-fluoro-1-oxazol-2-ylbenzene (1.1 g, 6.75 mmol) was added slowly. The reaction mixture was allowed to warm to 25° C., then stirred 90 minutes and diluted with water. The aqueous layer was separated and extracted with ethyl acetate (3×30 mL). The combined extracts were washed with brine, dried (MgSO$_4$) and concentrated. The residue was purified on silica gel by column chromatography eluting with hexanes/ethyl acetate (9:1) to give 4-benzyl-1-(2-oxazol-2-ylphenyl)piperazine (0.805 g, 2.52 mmol).

A mixture of the 4-benzyl-1-(2-oxazol-2-ylphenyl) piperazine (0.906 g, 2.84 mmol), obtained as in the proceeding paragraph, 10% palladium on carbon (1 g) and methanol (20 mL) was stirred 4 hours at 25° C. under a hydrogen atmosphere (15 psi). The reaction mixture then was filtered and concentrated by rotary evaporation to give 1-(2-oxazol-2-ylphenyl)piperazine (0.480 g, 2.1 mmol).

Proceeding as in Example 16, but substituting 2,4-difluoro-1-oxazol-2-ylbenzene gave 1-(4-fluoro-2-oxazol-2-ylphenyl)piperazine.

Example 17
1-(2-pyrrol-1-ylphenyl)piperazine

The following is the preparation of a compound of Formula 2 in which $R^1$ is pyrrol-1-yl and $R^2$ is hydro.

A mixture of 1-chloro-2-nitrobenzene (6.54 g, 41.5 mmol), piperazine-1-carboxaldehyde (4.7 g, 41.5 mmol) and DMF (18 mL) was heated 48 hours at 100° C. The reaction mixture then was cooled, diluted with water and extracted with ethyl acetate (3×). The combined extracts were washed with water, dried (MgSO$_4$), filtered and concentrated. The residue was purified by column chromatography on silica gel eluting with methylene chloride/methanol (98:2) to give 4-(2-nitrophenyl)piperazine-1-carbaldehyde (3.2 g, 13.7 mmol).

A mixture of the 4-(2-nitrophenyl)piperazine-1-carbaldehyde (3.57 g, 15.2 mmol), obtained as in the proceeding paragraph, 10% palladium on carbon and ethanol (50 mL) was stirred approximately 12 hours at 25° C. under a hydrogen atmosphere (15 psi). The reaction mixture then was filtered and concentrated to give 4-(2-aminophenyl) piperazine-1-carbaldehyde (2.91 g, 14.1 mmol), m.p. 129°–133° C.

A mixture of 4-(2-aminophenyl)piperazine-1-carbaldehyde (1.27 g, 6.2 mmol), 2,5-dimethoxytetrahydrofuran (1.13 g, 8.6 mmol) and concentrated acetic acid (4 mL) was heated 1.75 hours at reflux. The reaction mixture then was cooled in an ice-bath, diluted with water/ice and extracted with methylene chloride. The methylene chloride extract was washed with aqueous sodium hydroxide and then water, dried (MgSO$_4$), filtered and concentrated. The residue was purified by column chromatography on silica gel eluting with methylene chloride/methanol (97.5/2.5) to give 4-(2-pyrrol-1-ylphenyl)piperazine-1-carbaldehyde (1.12 g, 4.4 mmol) as an oil.

A mixture of 4-(2-pyrrol-1-ylphenyl)piperazine-1-carbaldehyde (1.12 g, 4.4 mmol), sodium hydroxide (440 mg, 11 mmoL) and methanol (10 mL) was heated 14 hours at 50° C. The reaction mixture was allowed to cool to approximately 25° C. and then partitioned between water (20 mL) and dichloroethane (30 mL). The aqueous layer was separated and extracted with dichloroethane (3×30 mL). The combined dichloroethane was washed with brine and dried (K$_2$CO$_3$). The residue was purified by column chromatography on silica gel eluting with a gradient of 1 to 5% methanol/0.1% triethylamine/dichloroethane to give 1-(2-pyrrol-1-ylphenyl)piperazine (0.77 g, 3.4 mmol).

Proceeding as in Example 17, but substituting 4-chloro-3-nitrotoluene for 1-chloro-2-nitrobenzene gave 1-(4-methyl-2-pyrrol-1-ylphenyl)piperazine.

Example 18
1-[2-(2,2,2-trifluoroethoxy)-4-hydroxyphenyl]piperazine

The following is the preparation of a compound of Formula 2 in which $R^1$ is 2,2,2-trifluoroethoxy and $R^2$ is hydro.

A mixture of 1-[2-(2,2,2-trifluoroethoxy)-4-methoxyphenyl]piperazine (1.87 g, 6.4 mmol) and 48% aqueous hydrobromic acid (5 mL) was heated 17 hours at reflux. The reaction mixture was allowed lo cool and then concentrated in vacuo. The residue was dissolved in ethanol (10 mL) at approximately 55° C. and the solution was cooled to 0° C. The solids were collected, washed with cold ethanol (3×10 mL) and dried in vacuo at approximately 80° C. to give 1-[2-(2,2,2-trifluoroethoxy)-4-hydroxyphenyl] piperazine hydrobromide, m.p. 190–194. Anal.: Calcd. for $C_{12}H_{14}F_3N_2O_2 \cdot (HBr)_{0.5} \cdot H_2O$: C, 43.00; H, 5.27; N, 8.37%; Found: C, 43.41; H, 4.97; N, 8.36%.

Example 19
1-methoxymethyl-3-(3-chloropropyl)-5-methyl-2,4(1H,3H)-pyrimidinedione The following is the preparation of a protected derivative of a compound of Formula 3 in which L is chloro, $R^3$ and $R^4$ are each hydro and $R^5$ is a group of Formula (a) wherein Z is CH, $R^7$ is methyl and the protective group is methoxymethyl.

A mixture of 1-methoxymethyl-5-methyl-2,4(1H,3H)-pyrimidinedione (115 g, 0.68 mol), prepared as in Example 6, sodium hydroxide (29.7 g, 0.74 mol), tetra-n-butylammonium bromide (10.9 g, 30 mmol) and DMF (350 mL) was heated with vigorous stirring at 25° to 35° C. until a nearly homogeneous solution was obtained. The mixture then was cooled to 25° C. and 1-bromo-3-chloropropane (73.5 mL, 0.75 mol) was added. The mixture was heated 16 hours with stirring at 25° to 35° C. and then partitioned between ethyl acetate (250 mL) and water (600 mL). The aqueous layer was extracted with ethyl acetate (4×50 mL) and the combined extracts were washed with dilute sodium hydroxide and water, dried (MgSO$_4$), filtered and concentrated in vacuo to give 1-methoxymethyl-3-(3-chloropropyl)-5-methyl-2,4(1H,3H)1-pyrimidinedione (154.5 g, 0.63 mol) as an oil.

Proceeding as in Example 19, but substituting a different starting material for 1-methoxymethyl-5-methyl-2,4(1H,3H)-pyrimidinedione, gave the following compounds of Formula 3 or a protected derivative thereof:

substituting 1-benzyl-5-methyl-2,4(1H,3H)-pyrimidinedione gave 1-benzyl-3-(3-chloropropyl)-5-methyl-2,4(1H,3H)-pyrimidinedione, m.p. 48°–50° C.;

substituting 4-benzyl-6-methyl-1,2,4-triazine-3,5(2H,4H)-dione gave 2-(3-chloropropyl)-6-methyl-1,2,4-triazine-3,5(2H,4H)-dione;

substituting 2-benzyl-6-methyl-1,2,4-triazine-3,5(2H,4H)-dione gave 4-(3-chloropropyl)-6-methyl-1,2,4-triazine-3,5(2H,4H)-dione;

substituting 1-(4-methoxybenzyl)-5-cyano-2,4(1H,3H)-pyrimidinedione gave 3-(3-chloropropyl)-1-(4-methoxybenzyl)-5-cyanc)-2,4(1H,3H)-pyrimidinedione;

substituting 1-benzyl-5-ethyl-2,4(1H,3H)-pyrimidinedione gave 1-benzyl-3-(3-chloropropyl)-5-ethyl-2,4(1H,3H)-pyrimidinedione as an oil;

substituting 1-benzyl-5-propyl-2,4(1H,3H)-pyrimidinedione gave 1-benzyl-3-(3-chloropropyl)-5-propyl-2,4(1H,3H)-pyrimidinedione as an oil;

substituting 1-[2-(trimethylsilyl)ethoxymethyl]-2,4(1H,3H)-pyrimidinedione gave 3-(3-chloropropyl)-1-[2-(trimethylsilyl)ethoxymethyl]-2,4(1H,3H)-pyrimidinedione as an oil;

substituting 1-benzyl-6-methyl-2,4(1H,3H)-pyrimidinedione gave 1-benzyl-3-(3-chloropropyl)-6-methyl-2,4(1H,3H)-pyrimidinedione;

substituting 3-benzyl-6-methyl-2,4(1H,3H)-pyrimidinedione gave 3-benzyl-1-(3-chloropropyl)-6-methyl-2,4(1H,3H)-pyrimidinedione;

substituting 5-methyl-1-phenyl-2,4(1H,3H)-pyrimidinedione gave 3-(3-chloropropyl)-5-methyl-1-phenyl-2,4(1H,3H)-pyrimidinedione;

substituting 5-methyl-3-phenyl-2,4(1H,3H)-pyrimidinedione gave 1-(3-chloropropyl)-5-methyl-3-phenyl-2,4(1H,3H)-pyrimidinedione;

substituting 1-(4-fluorophenyl)-5-methyl-2,4(1H,3H)-pyrimidinedione gave 3-(3-chloropropyl)-1-(4-fluorophenyl)-5-methyl-2,4(1H,3H)-pyrimidinedione;

substituting 3-(4-fluorophenyl)-5-methyl-2,4(1H,3H)-pyrimidinedione gave 1-(3-chloropropyl)-3-(4-fluorophenyl)-5-methyl-2,4(1H,3H)-pyrimidinedione;

substituting 1-benzyl-5-cyano-2,4(1H,3H)-pyrimidinedione gave 1-benzyl-3-(3-chloropropyl)-5-cyano-2,4(1H,3H)-pyrimidinedione;

substituting 1-biphenyl-3-ylmethyl-5-methyl-2,4(1H,3H)-pyrimidinedione gave 1-biphenyl-3-ylmethyl-3-(3-chloropropyl)-5-methyl-2,4(1H,3H)-pyrimidinedione;

substituting 1-(2-methylbenzyl)-5-methyl-2,4(1H,3H)-pyrimidinedione gave 3-(3-chloropropyl)-1-(2-methylbenzyl)-5-methyl-2,4(1H,3H)-pyrimidinedione;

substituting 1-(2,4-dimethylbenzyl)-5-methyl-2,4(1H,3H)-pyrimidinedione gave 3-(3-chloropropyl)-1-(2,4-dimethylbenzyl)-5-methyl-2,4(1H,3H)-pyrimidinedione;

substituting 1-(4-methoxybenzyl)-5-methyl-2,4(1H,3H)-pyrimidinedione gave 3-(3-chloropropyl)-1-(4-methoxybenzyl)-5-methyl-2,4(1H,3H)-pyrimidinedione;

substituting 1-cyclohexylmethyl-5-methyl-2,4(1H,3H)-pyrimidinedione gave 3-(3-chloropropyl)-1-cyclohexylmethyl-5-methyl-2,4–41H,3H)-pyrimidinedione;

substituting 5-methyl-1-pyrazin-2-yl-2,4(1H,3H)-pyrimidinedione gave 3-(3-chloropropyl)-5-methyl-1-pyrazin-2-yl-2,4(1H,3H)-pyrimidinedione;

substituting 1-benzyl-2,4-dioxo-5(1H,3H)-pyrimidinecarbaldehyde gave 1-benzyl-3-(3-chloropropyl)-2,4-dioxo-5(1H,3H)-pyrimidinecarbaldehyde;

substituting 1-fur-2-yl-5-methyl-2,4(1H,3H)-pyrimidinedione gave 1-fur-2-yl-3-(3-chloropropyl)-5-methyl-2,4(1H,3H)-pyrimidinedione;

substituting 1,5-dimethyl-2,4(1H,3H)-pyrimidinedione gave 3-(3-chloropropyl)-1,5-dimethyl-2,4(1H,3H)-pyrimidinedione;

substituting 5-methyl-1-thien-2-yl-2,4(1H,3H)-pyrimidinedione gave 3-(3-chloropropyl)-5-methyl-1-thien-2-yl-2,4(1H,3H)-pyrimidinedione;

substituting 1-fur-3-yl-5-methyl-2,4(1H,3H)-pyrimidinedione gave 1-fur-3-yl-3-(3-chloropropyl)-5-methyl-2,4(1H,3H)-pyrimidinedione;

substituting 5-methyl-1-pyrid-4-yl-2,4(1H,3H)-pyrimidinedione gave 3-(3-chloropropyl)-5-methyl-1-pyrid-4-yl-2,4(1H,3H)-pyrimidinedione;

substituting 1-benzyl-2,4(1H,3H)-pyrimidinedione gave 1-benzyl-3-(3-chloropropyl)-2,4(1H,3H)-pyrimidinedione;

substituting 5-methyl-1-pyrid-3-yl-2,4(1H,3H1)-pyrimidinedione gave 3-(3-chloropropyl)-5-methyl-1-pyrid-3-yl-2,4(1H,3H)-pyrimidinedione;

substituting 5-methyl-1-pyrid-2-yl-2,4(1H,3H)-pyrimidinedione gave 3-(3-chloropropyl)-5-methyl-1-pyrid-2-yl-2,4(1H,3H)-pyrimidinedione;

substituting 3-benzyl-5,6-dimethyl-2,4(1H,3H)-pyrimidinedione gave 3-benzyl-1-(3-chloropropyl)-5,6-dimethyl-2,4(1H,3H)-pyrimidinedione;

substituting 1-benzyl-5,6-dimethyl-2,4(1H,3H)-pyrimidinedione gave 1-benzyl-3-(3-chloropropyl)-5,6-dimethyl-2,4(1H,3H)-pyrimidinedione, m.p. 72°–74° C.;

substituting 3-benzyl-5-methyl-2,4(1H,3H)-pyrimidinedione gave 3-benzyl-1-(3-chloropropyl)-5-methyl-2,4(1H,3H)-pyrimidinedione, as an oil;

substituting 1-benzyl-5-trifluoromethyl-2,4(1H,3H)-pyrimidinedione gave 1-benzyl-3-(3-chloropropyl)-5-trifluoromethyl-2,4(1H,3H)-pyrimidinedione, m.p. 100°–101° C.;

substituting 5-hydroxymethyl-1-[2-(trimethylsilyl)ethoxymethyl]-2,4(1H,3H)-pyrimidinedione gave 3-(3-chloropropyl)-5-hydroxymethyl-1-[2-(trimethylsilyl)ethoxymethyl]-2,4(1H,3H)-pyrimidinedione;

substituting 1-[2-(trimethylsilyl)ethoxymethyl]-5-methoxy-2,4(1H,3H)-pyrimidinedione gave 3-(3-chloropropyl)-1-[2-(trimethylsilyl)ethoxymethyl]-5-methoxy-2,4(1H,3H)-pyrimidinedione;

substituting tert-butyl 5-prop-2-yl-2,4-dioxo-(1H,3H)-1-pyrimidinecarboxylate gave tert-butyl 3-(3-chloropropyl)-5-prop-2-yl-2,4-dioxo-(1H,3H)-1-pyrimidinecarboxylate;

substituting 1-(2,2,2-trifluoroethoxy)-5-methyl-2,4(1H,3H)-pyrimidinedione gave 3-(3-chloropropyl)-1-(2,2,2-trifluoroethoxy)-5-methyl-2,4(1H,3H)-pyrimidinedione;

substituting tert-butyl 5-methylthio-2,4-dioxo-(1H,3H)-1-pyrimidinecarboxylate gave tert-butyl 3-(3-chloropropyl)-5-methylthio-2,4-dioxo-(1H,3H)-1-pyrimidinecarboxylate; and substituting tert-butyl 5-fur-2-yl-2,4-dioxo-(1H,3H)-1-pyrimidinecarboxylate gave tert-butyl 3-(3-chloropropyl)-5-fur-2-yl-2,4-dioxo-(1H,3H)-1-pyrimidinecarboxylate.

Example 20

3-(3-chloropropyl)-5-methyl-2,4(1H,3H)-pyrimidinedione

The following is the preparation of a compound of Formula 3 in which L is chloro, $R^3$ and $R^4$ are each hydro and $R^5$ is a group of Formula (a) wherein Z is CH, $R^6$ is hydro and $R^7$ is methyl.

A mixture of 1-methoxymethyl-3-(3-chloropropyl)-5-methyl-2,4(1H,3H)-pyrimidinedione (40.4 g, 0.16 mol) and isopropanol (200 mL) was heated to 60° C. and added to refluxing concentrated hydrochloric acid (200 mL) at a rate such that the reaction mixture remained at gentle reflux. The mixture was heated 3 hours at reflux and then distilled to remove methanol byproduct. The mixture was heated 4.5 hours at 92° C., cooled to 25° C., poured into water (650 mL), saturated with sodium hydroxide and extracted with ethyl acetate (5×300 mL). The combined extracts were washed with sodium bicarbonate and water and concentrated in vacuo. The residue was recrystallized from toluene/isopropanol (10:1, 55 mL) and the solids were collected, washed with hexanes and dried at 60° C. (15 g 1st crop). The mother liquors were concentrated and the solids were collected, dried (2nd crop) and combined with the first crop to give 3-(3-chloropropyl)-5-methyl-2,4(1H,3H)-pyrimidinedione (19.8 g, 94 mmol), m.p. 145°–147° C.

Example 21

3-(3-chloropropyl)-5-methyl-2,4(1H,3H)-pyrimidinedione

The following is the preparation of a compound of Formula 3 in which L is chloro, $R^3$ and $R^4$ are each hydro and $R^5$ is a group of Formula (a) wherein Z is CH, $R^6$ is hydro and $R^7$ is methyl.

A mixture of 1-benzyl-3-(3-chloropropyl)-5-methyl-2,4(1H,3H)-pyrimidinedione (1 g, 3.41 mmol), prepared as in Example 19, 10% palladium on carbon (1 g) and 0.1M ammonium formate/methanol (340 mL) was heated 3 hours at reflux under argon. The reaction mixture was allowed to cool to 25° C., then filtered and concentrated in vacuo. The residue was purified by column chromatography on silica gel eluting with hexane-ethyl acetate (1:1) to give 3-(3-chloropropyl)-5-methyl-2,4(1H,3H)-pyrimidinedione (0.52 g, 2.57 mmol), m.p. 117°–121° C.

Proceeding as in Example 21, but substituting different a starting material for 1-benzyl-3-(3-chloropropyl)-5-methyl-2,4(1H,3H)-pyrimidinedione, gave the following compounds of Formula 3 or a protected derivative thereof:

substituting 4-benzyl-2-(3-chloropropyl)-6-methyl-1,2,4-triazine-3,5(2H,4H)-dione gave 2-(3-chloropropyl)-6-methyl-1,2,4-triazine-3,5(2H,4H)-dione;

substituting 2-benzyl-2-(3-chloropropyl)-6-methyl-1,2,4-triazine-3,5(2H,4H)-dione gave 4-(3-chloropropyl)-6-methyl-1,2,4-triazine-3,5(2H,4H)-dione;

substituting 3-benzyl-1-(3-chloropropyl)-5-methyl-2,4(1H,3H)-pyrimidinedione gave 1-(3-chloropropyl)-5-methyl-2,4(1H,3H)-pyrimidinedione;

substituting 3-benzyl-1-(3-chloropropyl)-5,6-dimethyl-2,4(1H,3H)-pyrimidinedione gave 1-(3-chloropropyl)-5,6-dimethyl-2,4(1H,3H)-pyrimidinedione;

substituting 3-benzyl-1-(3-chloropropyl)-6-methyl-2,4(1H,3H)-pyrimidinedione gave 1-(3-chloropropyl)-6-methyl-2,4(1H,3H)-pyrimidinedione;

substituting 1-benzyl-3-(3-chloropropyl)-5-trifluoromethyl-2,4(1H,3H)-pyrimidinedione gave 3-(3-chloropropyl)-5-trifluoromethyl-2,4(1H,3H)-pyrimidinedione;

substituting 1-benzyl-3-(3-chloropropyl)-6-methyl-2,4(1H,3H)-pyrimidinedione gave 3-(3-chloropropyl)-6-methyl-2,4(1H,3H)-pyrimidinedione;

substituting 1-benzyl-3-(3-chloropropyl)-5-ethyl-2,4(1H,3H)-pyrimidinedione gave 3-(3-chloropropyl)-5-ethyl-2,4(1H,3H)-pyrimidinedione;

substituting 1-benzyl-5-methyl-2,4,6(1H,3H, 5H)-pyrimidinetrione gave 5-methyl-2,4,6(1H,3H,5H)-pyrimidinetrione; and substituting 1-benzyl-3-(3-chloropropyl)-5-methyl-2,4(1H,3H)-pyrimidinedione gave 3-(3-chloropropyl)-5-methyl-2,4(1H,3H)-pyrimidinedione.

Example 22

1-(1-Benzyl-5-methyl-2,4-dioxo-(1H,3)-pyrimidin-3-ylmethyl)cycloprop-1-ylmethyl methanesulfonate The following is the preparation of a compound of Formula 3 in which L is methanesulfonyloxy, $R^3$ and $R^4$ together are ethylene and $R^5$ is a group of Formula (a) wherein Z is CH, $R^6$ is benzyl and $R^7$ is methyl.

A mixture of 1-cyano-1-cyclopropanecarboxylic acid (2 g, 18 mmol), dry triethylamine (3.3 mL, 23.5 mmol) and THF (25 mL) was cooled to between –5° C. and 0° C. and a mixture of methyl chloroformate (1.7 mL, 21.5 mmol) and THF (10 mL) was added at a rate such that the temperature of the reaction mixture remained between -5° C. and 0° C. The mixture was stirred 30 minutes, cooled to 0° C. and filtered (washing through with THF (5×10 mL)). The combined filtrate was cooled to 0° C. under argon and added to a mixture of sodium borohydride (2.04 g, 53.9 mmol) and water (12.5 mL) at <10° C. The mixture was stirred 2 hours at 25° C., treated with 10% hydrochloric acid and concentrate. The residual mixture was treated with 10% sodium bicarbonate and extracted with ethyl acetate. The organic layer was washed with brine, dried ($MgSO_4$) and concentrated to dryness. The residue was purified by flash chromatography on silica gel eluting with hexane/ethyl acetate (7:3) to give 1-cyanocycloprop-1-ylmethanol (1.16 g, 11.9 mmol) as an oil.

A mixture of 1-cyanocycloprop-1-ylmethanol (4.31 g, 44.4 mmol), obtained as in the proceeding paragraph, triethylamine (9.04 mL, 64.8 mmol) and methylene chloride (78 mL) was cooled under argon to between 0° and 5° C. and methanesulfonyl chloride (4.67 mL, 59.9 mmol) was added slowly. The mixture was cooled 3 hours with stirring at 0° to 5° C., then diluted with water and extracted with methylene chloride. The extract was washed with 5% sodium bicarbonate, dried ($MgSO_4$) and concentrated to dryness to give 1-cyano-cycloprop-1-ylmethyl methanesulfonate.

A mixture of the 1-cyanocycloprop-1-ylmethyl methanesulfonate and DMF (78 mL) was added to a mixture of 1-benzyl-5-methyl-2,4(1H,3H)-pyrimidinedione (9.1 g, 42.2 mmol), 60% sodium hydride (1.95 g, 48.8 mmol) and DMF (117 mL) at 0° to 5° C. The mixture was heated 20 hours at 45° to 55° C., then diluted with water (20 mL) and saturated ammonium chloride (20 mL) and extracted with ethyl acetate. The extract was washed with water and then brine, dried ($MgSO_4$) and concentrated to dryness. The residue was purified by flash chromatography on silica gel eluting with hexane/ethyl acetate (1:1) to give 1-benzyl-3-(1-cyanocycloprop-1-ylmethyl)-5-methyl-2,4(1H,3H)-pyrimidinedione (10.4 g, 35.2 mmol).

A mixture of 1-benzyl-3-(1-cyanocycloprop-1-ylmethyl)-5-methyl-2,4(1H,3H)-pyrimidinedione (10.4 g, 35.2 mmol), acetic acid (37.4 mL) and concentrated hydrochloric acid (164.4 mL) was heated 2 hours at reflux. The reaction mixture then was diluted with water (150 mL) and extracted with methylene chloride. The extract was extracted with 5% sodium hydroxide (3×). The combined aqueous phase was treated with 10% hydrochloric acid and extracted with methylene chloride. The methylene chloride extract was washed with water, dried ($MgSO_4$) and concentrated to dryness to give 1-(1-benzyl-5-methyl-2,4-dioxo-(1H,3H)-pyrimidin-3-ylmethyl)-1-cyclopropanecarboxylic acid (11.03 g, 35.1 mmol).

A mixture of 1-(1-benzyl-5-methyl-2,4-dioxo-(1H,3H)-pyrimidin-3-ylmethyl)-1-cyclopropanecarboxylic acid (11 g, 35 mmol), triethylamine (6.46 mL, 45.6 mmol) and THF (138 mL) was cooled to 0° C. under argon and a mixture of methyl chloroformate (3.23 mL, 42 mmol) and THF (20 mL) was added at a rate such that the temperature of the reaction mixture remained at 0° C. The mixture was cooled 30 minutes with stirring at 0° to 2° C. and then filtered (washing through with THF (3×50 mL)). The combined filtrate was cooled to 0° C. under argon and added to a mixture of sodium borohydride (3.29 g, 87 mmol) and water (23.3 mL) at <10° C. The mixture was stirred 2 hours, diluted with water (20 mL), treated with 10% hydrochloric acid, diluted with brine (40 mL) and extracted with ethyl acetate (4×100 mL). The combined extracts were washed with brine, dried ($MgSO_4$) and concentrated to dryness. The residue was purified by flash chromatography on silica gel eluting with hexane/ethyl acetate (7:3) to give 1-(1-benzyl-5-methyl-2,4-dioxo-(1H,3H)-pyrimidin-3-ylmethyl)cycloprop-1-ylmethanol (9.52 g, 31.7 mmol), m.p. 81.5° C.

A mixture of 1-(1-benzyl-5-methyl-2,4-dioxo-(1H,3H)-pyrimidin-3-ylmethyl)cycloprop-1-ylmethanol (1.95 g, 6.5 mmol), triethylamine (1.32 mL, 9.5 mmol) and methylene chloride (20 mL) was cooled to between 0° and 5° C. under argon and methanesulfonyl chloride (0.69 mL, 8.85 mmol) was added slowly. The mixture was stirred cooled 2 hours at 0° to 5° C., then diluted with water (20 mL) and extracted with methylene chloride. The extract was washed with 5% sodium bicarbonate, dried ($MgSO_4$) and concentrated to give 1-(1-benzyl-5-methyl-2,4-dioxo-(1H,3H)-pyrimidin-3-ylmethyl)cycloprop-1-ylmethyl methanesulfonate.

Example 23
3-(3-Chloropropyl)-5-methyl-2,4-dioxo-(1H,3H)-pyrimidin-1-ylmethylpyridine 1-oxide The following is the preparation of a compound of Formula 3 in which L is chloro, Z is CH, $R^3$ and $R^4$ are each hydro and $R^5$ is a group of Formula (a) wherein $R^6$ is 1-oxidopyrid-4-ylmethyl and $R^7$ is methyl.

A mixture of 3-(3-chloropropyl)-5-methyl-1-pyrid-4-yl-2,4-(1H,3H)-pyrimidinedione (0.54 g, 1.84 mmol), prepared as in Example 4, and methylene chloride (20 mL) was cooled to 0° C., treated with 3-chloroperoxybenzoic acid (tech. grade 0.55 g, 2.2 mmol), stirred 10 hours and then partitioned between aqueous sodium bicarbonate (20 mL) and methylene chloride (50 mL). The organic layer was separated, washed with 10% sodium sulfate (10 mL) and brine (10 mL) and concentrated in vacuo to give 3-(3-chloropropyl)-5-methyl-2,4-dioxo-(1H,3H)-pyrimidin-1-ylmethylpyridine-1-oxide (0.53 g, 1.7 mmol).

Example 24
3-{3-[4-(4-chloro-2-methoxyphenyl)piperazin-1-yl]propyl}-5-methyl-2,4(1H,3H)-pyrimidinedione The following is the preparation of a compound of Formula I in which $R^1$ is methoxy, $R^2$ is chloro at the 4-position, $R^3$ and $R^4$ are each hydro and $R^5$ is a group of Formula (a) wherein Z is CH, $R^6$ is hydro and $R^7$ is methyl.

A mixture of 3-(3-chloropropyl)-5-methyl-2,4(1H,3H)-pyrimidinedione (223 mg, 0.98 mmol), prepared as in Example 19, and 1-(4-chloro-2-methoxyphenyl)piperazine (200 mg, 0.98 mmol), prepared as in Example 12, was heated 2 hours with stirring at 180° to 190° C., allowed to cool to 25° C. and then purified by preparative thin layer chromatography on silica gel eluting with methylene chloride/(methylene chloride/methanol/ammonium hydroxide-60:10:1) (7:3) to give 3-{3-[4-(4-chloro-2-methoxyphenyl)piperazin-1-yl]propyl}-5-methyl-2,4(1H, 3H)-pyrimidinedione. The free base was recrystallized from a solution of hydrogen chloride in methanol to give 3-{3-[4-(4-chloro-2-methoxyphenyl)piperazin-1-yl]propyl}-5-methyl-2,4(1H,3H)-pyrimidinedione hydrochloride, m.p. 182°–184° C. Anal.: Calcd. for $C_{19}H_{25}ClN_4O_3 \cdot (HCl)_2$: C, 48.25; H, 5.92; N, 11.84%; Found: C, 48.55; H, 5.81; N, 11.85%.

Proceeding as in Example 24, but substituting a different starting material for 4-(4-chloro-2-methoxyphenyl)piperazine and/or 3-(3-chloropropyl)-5-methyl-2,4(1H,3H)-pyrimidinedione, gave the following compounds of Formula I:

substituting 1-[4-chloro-2-(2,2,2-trifluoroethoxy)phenyl]piperazine and recrystallizing from a solution of fumaric acid in alcohol gave 3-{3-[4-(4-chloro-2-(2,2,2-trifluoroethoxy)phenyl)piperazin-1-yl]propyl}-5-methyl-2,4(1H,3H)-pyrimidinedione fumarate, m.p. 180°–182° C.; Anal.: Calcd. for $C_{20}H_{24}ClN_4O_3 \cdot C_4H_4O_4$: C, 49.19; H, 4.84; N, 9.57%; Found: C, 49.29; H, 4.78; N, 9.40%; substituting 1-(2-fur-2-ylphenyl)piperazine and 1-tert-butyl 3-(3-chloropropyl)-5-methyl-2,4-dioxo-(1H,3H)-1-pyrimidinecarboxylate and recrystallizing from a solution of oxalic acid in alcohol gave 3-{3-(4-(2-fur-2-ylphenyl)-piperazin-1-yl]propyl}-5-methyl-2,4(1H,3H)-pyrimidinedione oxalate, m.p. 225°–226° C.;

substituting 1-(4-fluoro-2-hydroxyphenyl)piperazine and 1-tert-butyl 3-(3-chloropropyl)-5-methyl-2,4-dioxo-(1H,3H)-1-pyrimidinecarboxylate and recrystallizing from a solution of hydrobromic acid in alcohol gave 3-{3-[4-(4-fluoro-2-hydroxyphenyl)piperazin-1-yl]propyl}-5-methyl-2,4(1H,3H)-pyrimidinedione hydrobromide, m.p. 265°–268° C.; Anal.: Calcd. for $C_{18}H_{23}FN_4O_3 \cdot HBr$: C, 41.24; H, 4.81; N, 10.69%; Found: C, 41.44; H, 4.91; N, 10.61%; substituting 1-[4-fluoro-2-(2,2,2-trifluoroethoxy)phenyl]piperazine and 1-tert-butyl 3-(3-chloropropyl)-5-methylthio-2,4-dioxo-(1H,3H)-1-pyrimidinecarboxylate gave 3-{3-[4-(4-fluoro-2-(2,2,2-trifluoroethoxyphenyl)piperazin-1-yl]propyl}-5-methyl-2,4(1H,3H)-pyrimidinedione hydrochloride, m.p. 183°–186° C. (dec); Anal.: Calcd. for $C_{20}H_{25}F_4N_4O_3 \cdot HCl$: C, 46.83; H, 4.91; N, 10.92%; Found: C, 46.91; H, 5.01; N, 10.78%;

substituting 1-[4-fluoro-2-(2,2,2-trifluoroethoxy)phenyl]piperazine and tert-butyl 3-(3-chloropropyl)-5-prop-2-yl-2,4-dioxo-(1H,3H)-1-pyrimidinecarboxylate gave 3-{3-[4-(2-(4-fluoro-2,2,2-trifluoroethoxy)phenyl)piperazin-1-yl]propyl}-5-prop-2-yl-2,4(1H,3H)-pyrimidinedione hydrochloride, m.p. 204°–206° C.; Anal.: Calcd. for $C_{22}H_{28}F_4O_3 \cdot (HCl)_{1.5} \cdot (H_2O)_{0.5}$: C, 49.28; H, 5.73; N. 10.45%; Found: C, 49.57; H, 5.62; N, 10.42%; and substituting 1-[2-(2,2,2-trifluoroethoxy)phenyl]piperazine and tert-butyl 3-(3-chloropropyl)-5-fur-2-yl-2,4-dioxo-(1H,3H)-1-pyrimidinecarboxylate and recrystallizing from a solution of oxalic acid in alcohol gave 3-{3-[4-(2-(2,2,2-trifluoroethoxy)phenyl)piperazin-1-yl]propyl}-5-fur-2-yl-2,4(1H,3H)-pyrimidinedione oxalate, m.p. 202°–206° C.; Anal.: Calcd. for $C_{23}H_{25}F_3N_4O_2 \cdot C_2H_2O_4$: C, 52.81; H, 4.78; N, 9.85%; Found: C, 52.68; H, 4.89; N, 9.61%.

Example 25
1-Benzyl-3-{3-[4-(2-methoxyphenyl)piperazin-1-yl]propyl}-5-methyl-2,4(1H,3H)-pyrimidinedione The following is the preparation of a compound of Formula I in which $R^1$ is methoxy, $R^3$, $R^3$ and $R^4$ are each hydro and $R^5$ is a group of Formula (a) wherein Z is CH, $R^6$ is benzyl and $R^7$ is methyl.

A mixture of 1-benzyl-3-(3-chloropropyl)-5-methyl-2,4(1H,3H)-pyrimidinedione (550 mg, 1.87 mmol), prepared as in Example 19, 1-(2-methoxyphenyl)piperazine (367 g, 1.87 mmol), sodium iodide (623 g, 3.75 mmol), potassium carbonate (260 mg, 1.81 mmol) and acetonitrile (50 mL) was stirred 8 hours at reflux. The reaction mixture then was poured into water (200 mL) and extracted with methylene chloride (3×100 mL). The combined extracts were dried ($Na_2SO_4$) and concentrated in vacuo. The residue was purified by column chromatography on silica gel eluting with hexane/ethyl acetate (1:1) to give 1-benzyl-3-{3-[4-(2-methoxyphenyl)piperazin-1-yl]propyl}-5-methyl-2,4(1H,3H)-pyrimidinedione (800 mg, 1.78 mmol) as an oil. The free base was recrystallized from a solution of hydrochloric acid in alcohol to give 1-benzyl-3-{3-[4-(2-methoxyphenyl)piperazin-1-yl]propyl}-5-methyl-2,4(1H,3H)-pyrimidinedione hydrochloride, m.p. 195°–198° C. Anal.: Calcd. for $C_{26}H_{32}N_4O_3.(HCl)_2$: C, 59.88; H, 6.57; N, 10.74%; Found: C, 59.71; H, 6.64; N, 10.73%.

Proceeding as in Example 25, but substituting different starting materials for 3-(3-chloropropyl)-1-benzyl-5-methyl-2,4(1H,3H)-pyrimidinedione and/or 1-(2-methoxyphenyl)piperazine the following compounds of Formula I or the protected derivatives thereof were prepared:

substituting 3-benzyl-1-(3-chloropropyl)-5-methyl-2,4(1H, 3H)-pyrimidinedione gave 3-benzyl-1-{3-[4-(2-methoxyphenyl)piperazin-1-yl]propyl}-5-methyl-2,4(1H, 3H)-pyrimidinedione hydrochloride, m.p. 209°–211° C.; Anal.: Calcd. for $C_{26}H_{32}N_4O_3.(HCl)_2$: C, 59.88; H, 6.57; N, 10.74%; Found: C, 59.85; H, 6.57; N, 10.70%;

substituting 1-[2-(2,2,2-trifluoroethoxy)phenyl]piperazine gave 1-benzyl-3-{3-[4-(2,2,2-trifluoroethoxy)phenyl)piperazin-1-yl]propyl}-5-methyl-2,4(1H,3H)-pyrimidinedione hydrochloride, m.p. 87°–89° C.; Anal.: Calcd. for $C_{27}H_{31}F_3N_4O_3.HCl$: C, 55.91; H, 6.08; N, 9.66%; Found: C, 56.20; H, 5.96; N, 9.33%, substituting 1-(5-fluoro-2-methoxyphenyl)piperazine gave 1-benzyl-3-{3-[4-(5-fluoro-2-methoxyphenyl)piperazin-1-yl]propyl}-5-methyl-2,4(1H,3H)-pyrimidinedione hydrochloride, m.p. 165°–167° C.; Anal.: Calcd. for $C_{26}H_{31}FN_4O_3.(HCl)_2$: C, 57.88; H, 6.16; N, 10.38%; Found: C, 57.67; H, 6.20; N, 10.30%;

substituting 1-[4-chloro-2-(2,2,2-trifluoroethoxy)phenyl]piperazine and recrystallizing from a solution of fumaric acid in alcohol gave 1-benzyl-3-{3-[4-(4-chloro-2-(2,2,2-trifluoroethoxy)phenyl)piperazin-1-yl]propyl}-5-methyl-2,4(1H,3H)-pyrimidinedione fumarate, m.p. 156°–158° C.; Anal.: Calcd. for $C_{27}H_{30}F_3N_4O_3.C_4H_4O_4$: C, 55.07; H, 5.22; N, 8.29%; Found: C, 55.22; H, 5.16; N, 8.30%;

substituting 3-(3-chloropropyl)-1-benzyl-5,6-dimethyl-2,4(1H,3H)-pyrimidinedione gave 1-benzyl-3-{3-[4-(2-methoxyphenyl)piperazin-1-yl]propyl}-5,6-dimethyl-2,4(1H,3H)-pyrimidinedione hydrochloride, m.p. 239°–241° C.; Anal.: Calcd. for $C_{27}H_{34}N_4O_3.(HCl)_2$: C, 60.55; H, 6.77; N, 10.46%, Found: C, 60.33; H, 6.79; N, 10.37%;

substituting 1-(4-fluoro-2-methoxyphenyl)piperazine gave 1-benzyl-3-{3-[4-(4-fluoro-2-methoxyphenyl)piperazin-1-yl]propyl}-5-methyl-2,4(1H,3H)-pyrimidinedione hydrochloride, m.p. 178°–180° C.; Anal.: Calcd. for $C_{26}H_{31}FN_4O_3.(HCl)_2$: C, 57.50; H, 6.20; N, 10.32%; Found: C, 57.42; H, 6.14; N, 10.13%;

substituting 1-(4-chloro-2-methoxyphenyl)piperazine gave 1-benzyl-3-{3-[4-(4-chloro-2-methoxyphenyl)piperazin-1-yl]propyl}-5-methyl-2,4(1H,3H)-pyrimidinedione hydrochloride, m.p. 184°–186° C.; Anal.: Calcd. for $C_{26}H_{31}ClN_4O_3.(HCl)_2$: C, 55.86; H, 5.96; N, 10.00%; Found: C, 55.53; H, 5.85; N, 9.95%;

substituting 3-(3-chloropropyl)-1-benzyl-5-trifluoromethyl-2,4(1H,3H)-pyrimidinedione gave 1-benzyl-3-{3-[4-(2-methoxyphenyl)piperazin-1-yl]propyl}-5-trifluoromethyl-2,4(1H,3H)-pyrimidinedione hydrochloride, m.p. 240°–241° C.; Anal.: Calcd. for $C_{26}H_{29}F_3N_4O_3.(HCl)_2$: C, 54.26; H, 5.43; N, 9.73%; Found: C, 53.97; H, 5.40; N, 9.59%;

substituting 3-(3-chloropropyl)-5-cyano-1-(4-methoxybenzyl)-2,4(1H,3H)-pyrimidinedione gave 5-cyano-1-(4-methoxybenzyl)-3-{3-[4-(2-methoxyphenyl)piperazin-1-yl]propyl}-2,4(1H,3H)-pyrimidinedione hydrochloride, m.p. 248°–249° C. (dec); Anal.: Calcd. for $C_{27}H_{31}N_5O_4.(HCl)_{1.5}$: C, 57.67; H, 6.18; N, 12.46%; Found: C, 57.68; H, 6.02; N, 12.36%;

substituting 1-[4-fluoro-2-(2,2,2-trifluoroethoxy)phenyl]piperazine and recrystallizing from a solution of fumaric acid in alcohol gave 1-benzyl-3-(3-{4-[4-fluoro-2-(2,2,2-trifluoroethoxy)phenyl]piperazin-1-yl}propyl)-5-methyl-2,4(1H,3H)-pyrimidinedione fumarate, m.p. 145°–146° C.; Anal.: Calcd. for $C_{27}H_{30}F_4N_4O_3.C_4H_4O_4$: C, 57.22; H, 5.26; N, 8.61%; Found: C, 57.07; H, 5.28; N, 8.46%;

substituting 1-[2-(2,2,2-trifluoroethoxy)phenyl]piperazine and 3-(3-chloro)propyl-1-(2,4-dimethylbenzyl)-5-methyl-2,4(1H,3H)-pyrimidinedione gave 3-(3-{4-[2-(2,2,2-trifluoroethoxy)phenyl]piperazin-1-yl}propyl)-1-(2,4-dimethylbenzyl)-5-methyl-2,4(1H,3H)-pyrimidinedione hydrochloride, m.p. 113°–115° C.; Anal.: Calcd. for $C_{29}H_{37}F_3N_4O_3.(HCl)_2$: C, 55.04; H, 6.16; N, 8.85%; Found: C, 55.33; H, 6.00; N, 8.64%;

substituting 1-[2-(2,2,2-trifluoroethoxy)phenyl]piperazine and 3-(3-chloro)propyl-1-(2-methylbenzyl)-2,4(1H,3H)-pyrimidinedione gave 3-(3-{4-[2-(2,2,2-trifluoroethoxy)phenyl]piperazin-1-yl}propyl)-1-(2-methylbenzyl)-2,4(1H,3H)-pyrimidinedione hydrochloride, m.p. 172°–174° C.; Anal.: Calcd. for $C_{28}H_{34}F_3N_4O_3.HCl$: C, 57.93; H, 6.16; N, 9.65%; Found: C, 57.86; H, 6.02; N, 9.55%;

substituting 3-(3-chloropropyl)-1-benzyl-5-propyl-2,4(1H, 3H)-pyrimidinedione gave 1-benzyl-3-{3-[4-(2-methoxyphenyl)piperazin-1-yl]propyl}-5-propyl-2,4(1H, 3H)-pyrimidinedione hydrochloride, m.p. 202°–204° C.; Anal.: Calcd. for $C_{28}H_{36}N_4O_3.HCl$: C, 65.30; H, 7.28; N, 10.88%; Found: C, 65.07; H, 7.24; N, 10.74%;

substituting 3-(3-chloropropyl)-1-benzyl-5-ethyl-2,4(1H, 3H)-pyrimidinedione gave 1-benzyl-3-{3-[4-(2-methoxyphenyl)piperazin-1-yl]propyl}-5-ethyl-2,4(1H, 3H)-pyrimidinedione hydrochloride, m.p. 183°–185° C.; Anal.: Calcd. for $C_{27}H_{34}N_4O_3.(HCl)_2$: C, 60.55; H, 6.77; N, 10.46%; Found: C, 60.40; H, 6.86; N, 10.25%;

substituting 1-(2-(2,2,2-trifluoroethoxy)phenyl]piperazine and 1-biphenyl-3-ylmethyl-3-(3-chloropropyl)-5-methyl-2,4(1H,3H)-pyrimidinedione gave 1-biphenyl-3-ylmethyl-3-(3-{4-[2-(2,2,2-trifluoroethoxy)phenyl]piperazin-1-yl}-propyl)-5-methyl-2,4(1H,3H)-pyrimidinedione hydrochloride, m.p. 93°–94° C.; Anal.: Calcd. for $C_{33}H_{35}F_3N_4O_3.HCl$: C, 63.06; H, 5.77; N, 8.92%; Found: C, 61.66; H, 5.90; N, 8.50%;

substituting 1-[2-(2,2,2-trifluoroethoxy)phenyl]piperazine and 3-(3-chloropropyl)-1-benzyl-5-ethyl-2,4(1H,3H)-pyrimidinedione gave 1-benzyl-3-{3-[4-(2-(2,2,2-trifluoroethoxy)phenyl)piperazin-1-yl]propyl}-5-ethyl-2, 4(1H,3H)-pyrimidinedione hydrochloride, m.p.

180°–181° C.; Anal.: Calcd. for $C_{28}H_{33}F_3N_4O_3.HCl$: C, 58.56; H, 6.11; N, 9.76%; Found: C, 58.83; H, 6.11; N, 9.77%;

substituting 1-(4-fluoro-2-methoxyphenyl)piperazine and 1-(3-chloropropyl)-3-benzyl-5-methyl-2,4(1H,3H)-pyrimidinedione gave 3-benzyl-1-{3-[4-(4-fluoro-2-methoxyphenyl)piperazin-1-yl]propyl}-5-methyl-2,4(1H,3H)-pyrimidinedione hydrochloride, m.p. 210°–212° C.; Anal.: Calcd. for $C_{26}H_{31}FN_4O_3.(HCl)_2$: C, 57.88; H, 6.16; N, 10.38%; Found: C, 57.50; H, 6.18; N, 10.62%;

substituting 1-[2-(2,2,2-trifluoroethoxy)phenyl]piperazine and 3-(3-chloropropyl)-1-benzyl-5,6-dimethyl-2,4(1H,3H)-pyrimidinedione gave 1-benzyl-3-(3-{4-[2-(2,2,2-trifluoroethoxy)phenyl]piperazin-1-yl}propyl)-5,6-dimethyl-2,4(1H,3H)-pyrimidinedione hydrochloride, m.p. 221°14 222° C.; Anal.: Calcd. for $C_{28}H_{33}F_3N_4O_3.(HCl)_{1.1}$: C, 58.37; H, 6.06; N, 9.72%; Found: C, 58.38; H, 5.96; N, 9.58%;

substituting 1-[2-(2,2,2-trifluoroethoxy)phenyl]piperazine and 1-(3-chloropropyl)-3-benzyl-5-methyl-2,4(1H,3H)-pyrimidinedione gave 3-benzyl-1-(3-{4-(2-(2,2,2-trifluoroethoxy)phenyl]piperazin-1-yl}propyl)-5-methyl-2,4(1H,3H)-pyrimidinedione hydrochloride, m.p. 168°–169° C.; Anal.: Calcd. for $C_{27}H_{31}F_3N_4O_3.(HCl)_{1.9}$: C, 55.01; H, 5.69; N, 9.50%; Found: C, 54.95; H, 5.59; N, 9.43%;

substituting 1-[2-(2,2,2-trifluoroethoxy)phenyl]piperazine and 3-(3-chloropropyl)-1-cyclohexylmethyl-5-methyl-2,4(1H,3H)-pyrimidinedione gave 1-cyclohexylmethyl-3-(3-{4-[2-(2,2,2-trifluoroethoxy)phenyl]piperazin-1-yl}propyl)-5-methyl-2,4(1H,3H)-pyrimidinedione hydrochloride, m.p. 130°–132° C.; Anal.: Calcd. for $C_{27}H_{37}F_3N_4O_3.HCl$: C, 57.99; H, 6.88; N, 10.02%; Found: C, 58.01; H, 6.80; N, 9.87%;

substituting 1-[2-(2,2,2-trifluoroethoxy)phenyl]piperazine and 3-(3-chloropropyl)-1-pyrazin-2-ylmethyl-5-methyl-2,4(1H,3H)-pyrimidinedione and recrystallizing from a solution of fumaric acid in alcohol gave 3-(3-{4-[2-(2,2,2-trifluoroethoxy)phenyl]piperazin-1-yl}propyl)-5-methyl-1-pyrazin-2-ylmethyl-2,4(1H,3H)-pyrimidinedione fumarate, m.p. 149°–151° C.; Anal.: Calcd. for $C_{25}H_{29}F_3N_6O_3.C_4H_4O_4$: C, 53.08; H, 5.44; N, 12.81%, Found: C, 52.87; H, 5.13; N, 12.83%;

substituting 1-(4-chloro-2-methoxyphenyl)piperazine and 3-benzyl-1-(3-chloropropyl)-5-methyl-2,4(1H,3H)-pyrimidinedione gave 3-benzyl-1-{3-[4-(4-chloro-2-methoxyphenyl)piperazin-1-yl]propyl}-5-methyl-2,4(1H,3H)-pyrimidinedione hydrochloride, m.p. 194°–195° C.; Anal.: Calcd. for $C_{26}H_{31}ClN_4O_3.(HCl)_2$: C, 55.63; H, 6.03; N, 9.98%; Found: C, 55.82; H, 5.94; N, 9.85%;

substituting 1-[4-chloro-2-(2,2,2-trifluoroethoxy)phenyl]piperazine and 3-benzyl-1-(3-chloropropyl)-5-methyl-2,4(1H,3H)-pyrimidinedione gave 3-benzyl-1-(3-{4-[4-chloro-2-(2,2,2-trifluoroethoxy)phenyl]piperazin-1-yl}propyl)-5-methyl-2,4(1H,3H)-pyrimidinedione hydrochloride, m.p. 251°–252° C.; Anal.: Calcd. for $C_{27}H_{30}F_3ClN_4O_3.HCl$: C, 53.55; H, 5.49; N, 9.25%; Found: C, 53.74; H, 5.26; N, 9.37%;

substituting 1-[2-(2,2,2-trifluoroethoxy)phenyl]piperazine and 1-benzyl-3-(3-chloropropyl)-5-propyl-2,4(1H,3H)-pyrimidinedione gave 1-benzyl-3-(3-{4-[2-(2,2,2-trifluoroethoxy)phenyl]piperazin-1-yl}propyl)-5-propyl-2,4(1H,3H)-pyrimidinedione hydrochloride, m.p. 178° C.; Anal.: Calcd. for $C_{29}H_{35}F_3N_4O_3.HCl$: C, 59.03; H, 6.32; N, 9.49%; Found: C, 59.08; H, 6.26; N, 9.52%;

substituting 1-[2-(2,2,2-trifluoroethoxy)phenyl]piperazine and 1-benzyl-3-(3-chloropropyl)-5-trifluoromethyl-2,4(1H,3H)-pyrimidinedione gave 1-benzyl-3-(3-(4-[2-(2,2,2-trifluoroethoxy)phenyl]piperazin-1-yl)propyl)-5-trifluoromethyl-2,4(1H,3H)-pyrimidinedione hydrochloride, m.p. 125°–127° C.; Anal.: Calcd. for $C_{27}H_{28}F_6N_4O_3.HCl$: C, 52.65; H, 4.91; N, 9.10%; Found: C, 52.44; H, 4.79; N, 8.92%;

substituting 1-benzyl-3-(3-chloropropyl)-2,4-dioxo-5(1H,3H)-pyrimidinecarbaldehyde and recrystallizing from a solution of fumaric acid in alcohol gave 1-benzyl-3-{3-[4-(2-methoxyphenyl)piperazin-1-yl]propyl}-2,4-dioxo-5(1H,3H)-pyrimidinecarbaldehyde fumarate, m.p. 198° C.; Anal.: Calcd. for $C_{26}H_{30}N_4O_4.(C_4H_4O_4)_{0.5}$: C, 64.37; H, 6.16; N, 10.72%; Found: C, 64.07; H, 6.25; N, 11.12%;

substituting 1-[2-(2,2,2-trifluoroethoxy)phenyl]piperazine and 1-benzyl-3-(3-chloropropyl)-5-cyano-2,4(1H,3H)-pyrimidinedione gave 1-benzyl-3-(3-{4-[2-(2,2,2-trifluoroethoxy)phenyl]piperazin-1-yl}propyl)-5-cyano-2,4(1H,3H)-pyrimidinedione hydrochloride, m.p. 142°–143° C.; Anal.: Calcd. for $C_{27}H_{28}F_3N_5O_3.(HCl)_{1.2}.(H_2O)_{0.5}$: C, 57.50; H, 5.18; N, 12.42%; Found: C, 55.93; H, 5.22; N, 11.94%;

substituting 1-[2-(2,2,2-trifluoroethoxy)phenyl]piperazine and 3-(3-chloropropyl)-1-fur-2-ylmethyl-5-methyl-2,4(1H,3H)-pyrimidinedione gave 3-(3-{4-[2-(2,2,2-trifluoroethoxy)phenyl]piperazine-1-yl}propyl)-1-fur-2-ylmethyl-5-methyl-2,4(1H,3H)-pyrimidinedione hydrochloride, m.p. 132°–134° C.; Anal.: Calcd. for $C_{25}H_{29}F_3N_4O_4.(HCl)_2$: C, 51.81; H, 5.39; N, 9.66%; Found: C, 51.89; H, 5.44; N, 9.55%;

substituting 1-[2-(2,2,2-trifluoroethoxy)phenyl]piperazine and 3-(3-chloropropyl)-5-trifluoromethyl-2,4(1H,3H)-pyrimidinedione gave 3-(3-{4-[2-(2,2,2-trifluoroethoxy)phenyl]piperazin-1-yl}propyl)-5-trifluoromethyl-2,4(1H,3H)-pyrimidinedione hydrochloride, m.p. 225°–226° C.; Anal.: Calcd. for $C_{20}H_{22}F_6N_4O_3.(HCl)_2$: C, 43.061; H, 4.43; N, 10.04%; Found: C, 43.12; H, 4.59; N, 9.81%;

substituting 1-[2-(2,2,2-trifluoroethoxy)phenyl]piperazine and 3-(3-chloropropyl)-1,5-dimethyl-2,4(1H,3H)-pyrimidinedione gave 3-(3-{4-[2-(2,2,2-trifluoroethoxy)phenyl]piperazin-1-yl}propyl)-1,5-dimethyl-2,4(1H,3H)-pyrimidinedione hydrochloride, m.p. 212°14 213° C.; Anal.: Calcd. for $C_{21}H_{27}F_3N_4O_3.(HCl)_2$: C, 49.12; H, 5.69; N, 10.91%; Found: C, 48.97; H, 5.68; N, 10.77%;

substituting 1-(4-fluoro-2-methoxyphenyl)piperazine and 1-(3-chloropropyl)-5-methyl-2,4(1H,3H)-pyrimidinedione gave 1-{3-[4-(4-fluoro-2-methoxyphenyl)piperazin-1-yl]propyl}-5-methyl-2,4(1H,3H)-pyrimidinedione hydrochloride, m.p. 196°–197° C.; Anal.: Calcd. for $C_{19}H_{25}FN_4O_3.(HCl)_2$: C, 49.79; H, 6.16; N, 12.22%; Found: C, 50.13; H, 6.37; N, 12.27%;

substituting 1-[2-(2,2,2-trifluoroethoxy)phenyl]piperazine and 1-(3-chloropropyl)-3-benzyl-5,6-dimethyl-2,4(1H,3H)-pyrimidinedione and recrystallizing from a solution of fumaric ac:Ld in alcohol gave 1-(3-{4-[2-(2,2,2-trifluoroethoxy)phenyl]piperazin-1-yl}propyl)-3-benzyl-5,6-dimethyl-2,4(1H,3H)-pyrimidinedione fumarate, m.p. 125°–127° C.; Anal.: Calcd. for $C_{28}H_{33}F_3N_4O_3.C_2H_2O_2$: C, 58.62; H, 5.84; N, 8.55%; Found: C, 58.63; H, 5.67; N, 8.42%;

substituting 1-[4-chloro-2-(2,2,2-trifluoroethoxy)phenyl]piperazine and 1-(3-chloropropyl)-5-methyl-2,4(1H,3H)-pyrimidinedione gave 1-(3-{4-[4-chloro-2-(2,2,2-trifluoroethoxy)phenyl]piperazin-1-yl}propyl)-5-methyl-2,4(1H,3H)-pyrimidinedione hydrochloride, m.p. 205°–206° C.; Anal.: Calcd. for $C_{20}H_{24}ClF_3N_4O_3.(HCl)_2$: C, 43.53; H, 5.10; N, 10.15%; Found: C, 43.77; H, 5.10; N, 10.13%;

substituting 1-(4-chloro-2-methoxyphenyl)piperazine and 1-(3-chloropropyl)-5-methyl-2,4(1H,3H)-pyrimidinedione gave 1-{3-[4-(4-chloro-2-methoxyphenyl)piperazin-1-yl]propyl}-5-methyl-2,4(1H,3H)-pyrimidinedione hydrochloride, m.p. 154°–155° C.; Anal.: Calcd. for $C_{19}H_{25}ClN_4O_3 \cdot (HCl)_2$: C, 44.05; H, 6.37; N, 10.81%; Found: C, 44.26; H, 6.08; N, 10.46%;

substituting 1-[2-(2,2,2-trifluoroethoxy)phenyl]piperazine and 3-(3-chloropropyl)-5-methyl-1-thien-2-ylmethyl-2,4(1H,3H)-pyrimidinedione gave 3-(3-{4-[2-(2,2,2-trifluoroethoxy)phenyl]piperazin-1-yl}propyl)-5-methyl-1-thien-2-yl-2,4(1H,3H)-pyrimidinedione hydrochloride, m.p. 103°–106° C.; Anal.: Calcd. for $C_{25}H_{29}SF_3N_4O_3 \cdot (HCl)_2$: C, 53.03; H, 5.48; N, 9.89%; Found: C, 53.25; H, 5.31; N, 9.52%;

substituting 1-[2-(2,2,2-trifluoroethoxy)phenyl]piperazine and 1-benzyl-3-(3-chloropropyl)-2,4-dioxo-5(1H,3H)-pyrimidinecarbaldehyde and recrystallizing from a solution of fumaric acid in alcohol gave 1-benzyl-3-(3-{4-[2-(2,2,2-trifluoroethoxy)phenyl]piperazin-1-yl}propyl)-2,4-dioxo-5(1H,3H)-pyrimidinecarbaldehyde fumarate, m.p. 175° C.; Anal.: Calcd. for $C_{27}H_{29}F_3N_4O_4 \cdot C_4H_4O_4$: C, 57.58; H, 5.14; N, 8.66%; Found: C, 57.42; H, 5.13; N, 8.61%;

substituting 1-[4-hydroxy-2-(2,2,2-trifluoroethoxy)phenyl]piperazine and 3-(3-chloropropyl)-5-methyl-2,4(1H,3H)-pyrimidinedione gave 3-(3-{4-[4-hydroxy-2-(2,2,2-trifluoroethoxy)phenyl]piperazin-1-yl}propyl)-5-methyl-2,4(1H,3H)-pyrimidinedione hydrochloride, m.p. 232°–242° C.; Anal.: Calcd. for $C_{20}H_{25}F_3N_4O_4 \cdot HCl$: C, 49.63; H, 5.59; N, 11.02%; Found: C, 49.62; H, 5.65; N, 10.66%;

substituting 1-[2-(2,2,2-trifluoroethoxy)phenyl]piperazine and 3-(3-chloropropyl)-1-fur-3-ylmethyl-5-methyl-2,4(1H,3H)-pyrimidinedione gave 3-(3-{4-[2-(2,2,2-trifluoroethoxy)phenyl]piperazin-1-yl}propyl)-1-fur-3-yl-methyl-5-methyl-2,4(1H,3H)-pyrimidinedione hydrochloride, m.p. 128°–131° C.; Anal.: Calcd. for $C_{25}H_{29}F_3N_4O_4 \cdot (HCl)_2$: C, 50.26; H, 5.57; N, 9.38%; Found: C, 50.55; H, 5.25; N, 9.22%;

substituting 1-[2-(2,2,2-trifluoroethoxy)phenyl]piperazine and 1-(3-chloropropyl)-5,6-dimethyl-2,4(1H,3H)-pyrimidinedione and recrystallizing from a solution of fumaric acid in alcohol gave 1-(3-{4-[2-(2,2,2-trifluoroethoxy)phenyl]piperazin-1-yl}propyl)-5,6-dimethyl-2,4(1H,3H)-pyrimidinedione fumarate, m.p. 201°–203° C.; Anal.: Calcd. for $C_{21}H_{27}F_3N_4O_3 \cdot C_4H_4O_4$: C, 53.95; H, 5.61; N, 10.06%; Found: C, 53.93; H, 5.71; N, 10.00%;

substituting 3-(3-chloropropyl)-5-methyl-1-pyrid-4-ylmethyl-2,4(1H,3H)-pyrimidinedione and recrystallizing from a solution of fumaric acid in alcohol gave di(3-{3-[4-(2-methoxyphenyl)piperazin-1-yl]propyl}-5-methyl-1-pyrid-4-ylmethyl-2,4(1H,3H)-pyrimidinedione) fumarate, m.p. 210°–212° C.; Anal.: Calcd. for $(C_{25}H_{31}N_5O_3)_2 \cdot C_4H_4O_4$: C, 66.33; H, 6.59; N, 13.68%; Found: C, 63.49; H, 6.65; N, 13.58%;

substituting 3-benzyl-1-(3-chloropropyl)-5,6-dimethyl-2,4(1H,3H)-pyrimidinedione and recrystallizing from a solution of fumaric acid in alcohol gave 3-benzyl-1-{3-[4-(2-methoxyphenyl)piperazin-1-yl]propyl}-5,6-dimethyl-2,4(1H,3H)-pyrimidinedione fumarate, m.p. 164°–166° C.; Anal.: Calcd. for $C_{27}H_{34}N_4O_3 \cdot C_4H_4O_4$: C, 64.35; H, 6.62; N, 9.68%; Found: C, 64.57; H, 6.67; N, 9.71%;

substituting 1-[2-(2,2,2-trifluoroethoxy)phenyl]piperazine and 3-(3-chloropropyl)-5-methyl-1-pyrid-4-ylmethyl-2,4(1H,3H)-pyrimidinedione and recrystallizing from a solution of fumaric acid in alcohol gave 3-(3-{4-[2-(2,2,2-trifluoroethoxy)phenyl]piperazin-1-yl}propyl)-5-methyl-1-pyrid-4-ylmethyl-2,4(1H,3H)-pyrimidinedione fumarate, m.p. 122°–124° C.; Anal.: Calcd. for $C_{26}H_{30}F_3N_5O_3 \cdot C_4H_4O_4$: C, 56.07; H, 5.49; N, 10.90%; Found: C, 56.36; H, 5.55; N, 10.61%;

substituting 3-(3-chloropropyl)-6-methyl-2,4(1H,3H)-pyrimidinedione gave 3-{3-[4-(2-methoxyphenyl)piperazin-1-yl]propyl}-6-methyl-2,4(1H,3H)-pyrimidinedione hydrochloride, m.p. 232°–234° C.; Anal.: Calcd. for $C_{19}H_{26}N_4O_3 \cdot (HCl)_2$: C, 51.19; H, 6.68; N, 12.56%; Found: C, 51.11; H, 6.47; N, 12.44%;

substituting 1-[2-(2,2,2-trifluoroethoxy)phenyl]piperazine and 1-benzyl-3-(3-chloropropyl)-2,4(1H,3H)-pyrimidinedione gave 1-benzyl-3-(3-{4-[2-(2,2,2-trifluoroethoxy)phenyl]piperazin-1-yl}propyl)-2,4(11H,3H)-pyrimidinedione hydrochloride; Anal.: Calcd. for $C_{26}H_{29}F_3N_4O_3 \cdot (HCl)_2$: C, 53.43; H, 5.52; N, 9.59%; Found: C, 53.22; H, 5.34; N, 9.37%;

substituting 1-[4-methyl-2-(2,2,2-trifluoroethoxy)phenyl]piperazine and 3-(3-chloropropyl)-5-methyl-2,4(1H,3H)-pyrimidinedione and recrystallizing from a solution of hydrobromic acid in alcohol gave 3-(3-{4-[4-methyl-2-(2,2,2-trifluoroethoxy)phenyl]piperazin-1-yl)propyl)-5-methyl-2,4(1H,3H)-pyrimidinedione hydrobromide, m.p. 86°–90° C.; Anal.: Calcd. for $C_{21}H_{27}F_3N_4O_3 \cdot HBr$: C, 48.38; H, 5.41; N, 10.75%; Found: C, 48.73; H, 5.62; N, 10.51%;

substituting 1-[2-(2,2,2-trifluoroethoxy)pheny]piperazine and 3-(3-chloropropyl)-6-methyl-2,4(1H,3H)-pyrimidinedione gave 3-(3-{4-[2-(2,2,2-trifluoroethoxy)phenyl]piperazin-1-yl}propyl)-6-methyl-2,4(1H,3H)-pyrimidinedione hydrochloride, m.p. 218°–220° C.; Anal.: Calcd. for $C_{20}H_{25}F_3N_4O_3 \cdot (HCl)_2$: C, 48.10; H, 5.44; N, 11.22%; Found: C, 47.85; H, 5.48; N, 11.08%;

substituting 1-[2-(2,2,2-trifluoroethoxy)phenyl]piperazine and 3-(3-chloropropyl)-5-methyl-1-pyrid-3-ylmethyl-2,4(1H,3H)-pyrimidinedione and recrystallizing from a solution of fumaric acid in alcohol gave 3-(3-{4-[2-(2,2,2-trifluoroethoxy)phenyl]piperazin-1-yl}propyl)-5-methyl-1-pyrid-3-ylmethyl-2,4(1H,3H)-pyrimidinedione fumarate, m.p. 158°–160° C.; Anal.: Calcd. for $C_{26}H_{30}F_3N_5O_3 \cdot C_4H_4O_4$: C, 56.55; H, 5.93; N, 10.30%; Found: C, 56.27; H, 5.82; N, 10.05%;

substituting 1-[2-(2,2,2-trifluoroethoxy)phenyl]piperazine and 3-(3-chloropropyl)-5-methyl-1-phenyl-2,4(1H,3H)-pyrimidinedione and recrystallizing from a solution of fumaric acid in alcohol gave 3-(3-{4-[2-(2,2,2-trifluoroethoxy)phenyl]piperazin-1-yl}propyl)-5-methyl-1-phenyl-2,4(1H,3H)-pyrimidinedione fumarate, m.p. 190°–192° C.; Anal.: Calcd. for $C_{26}H_{29}F_3N_4O_3 \cdot C_4H_4O_4$: C, 58.25; H, 5.38; N, 9.06%; Found: C, 58.11; H, 5.45; N, 9.20%;

substituting 1-[2-(2,2,2-trifluoroethoxy)phenyl]piperazine and 1-(3-chloropropyl)-5-methyl-3-phenyl-2,4(1H,3H)-pyrimidinedione and recrystallizing from a solution of fumaric acid in alcohol gave 1-(3-(4-[2-(2,2,2-trifluoroethoxy)phenyl]piperazin-1-yl}propyl)-5-methyl-3-phenyl-2,4(1H,3H)-pyrimidinedione fumarate; Anal.: Calcd. for $C_{26}H_{29}F_3N_4O_3 \cdot C_4H_4O_4$: C, 57.41; H, 5.46; N, 8.93%; Found: C, 57.37; H, 5.45; N, 8.63%;

substituting 1-(3-chloropropyl)-6-methyl-2,4(1H,3H)-pyrimidinedione gave 1-{3-[4-(2-methoxyphenyl)piperazin-1-yl]propyl}-6-methyl-2,4(1H,3H)-pyrimidinedione hydrochloride, m.p. 228°–230° C.; Anal.: Calcd. for $C_{19}H_{26}N_4O_3 \cdot (HCl)_2$: C, 51.39; H, 6.66; N, 12.62%; Found: C, 51.14; H, 6.36; N, 12.38%;

substituting 1-[2-(2,2,2-trifluoroethoxy)phenyl]piperazine and 1-(3-chloropropyl)-6-methyl-2,4(1H,3H)-pyrimidinedione gave 1-(3-{4-[2-(2,2,2-trifluoroethoxy)phenyl]piperazin-1-yl}propyl)-6-methyl-2,4(1H,3H)-pyrimidinedione hydrochloride, m.p. 217°–219° C.; Anal.: Calcd. for $C_{20}H_{25}F_3N_4O_3.(HCl)_2$: C, 48.10; H, 5.44; N, 11.22%; Found: C, 47.96; H, 5.46; N, 11.15%;

substituting 1-(4-fluoro-2-methoxyphenyl)piperazine and 3-(3-chloropropyl)-6-methyl-2,4(1H,3H)-pyrimidinedione gave 3-{3-[4-(4-fluoro-2-methoxyphenyl)piperazin-1-yl]propyl}-6-methyl-2,4(1H,3H)-pyrimidinedione hydrochloride, m.p. 235°–237° C.; Anal.: Calcd. for $C_{19}H_{25}FN_4O_3.(HCl)_2$: C, 49.20; H, 6.21; N, 12.08%; Found: C, 49.02; H, 6.22; N, 12.01%;

substituting 1-(4-fluoro-2-methoxyphenyl)piperazine and 3-(3-chloropropyl)-5-methyl-1-pyrid-3-ylmethyl-2,4(1H,3H)-pyrimidinedione and recrystallizing from a solution of fumaric acid in alcohol gave 3-{3-[4-(4-fluoro-2-methoxyphenyl)piperazin-1-yl]propyl}-5-methyl-1-pyrid-3-ylmethyl-2,4(1H,3H)-pyrimidinedione fumarate; Anal.: Calcd. for $C_{25}H_{30}FN_5O_3.C_4H_4O_4$: C, 57.90; H, 6.03; N, 11.64%; Found: C, 58.07; H, 5.93; N, 11.34%;

substituting 1-(4-fluoro-2-ethoxyphenyl)piperazine and 3-(3-chloropropyl)-5-ethyl-2,4(1H,3H)-pyrimidinedione and recrystallizing from a solution of hydrobromic acid in alcohol gave 3-{3-[4-(4-fluoro-2-ethoxyphenyl)piperazin-1-yl]propyl}-5-ethyl-2,4(1H,3H)-pyrimidinedione hydrobromide, m.p. 224°–227° C.; Anal.: Calcd. for $C_{21}H_{29}FN_4O_3.HBr$: C, 44.54; H, 5.52; N, 9.89%; Found: C, 44.22; H, 5.48; N, 9.76%;

substituting 1-(4-fluoro-2-oxazol-2-ylphenyl)piperazine and 3-(3-chloropropyl)-5-methyl-2,4(1H,3H)-pyrimidinedione and recrystallizing from a solution of oxalic acid in alcohol gave 3-{3-[4-(4-fluoro-2-oxazol-2-ylphenyl)piperazin-1-yl]propyl}-5-methyl-2,4(1H,3H)-pyrimidinedione oxalate, m.p. 207°–210° C.; Anal.: Calcd. for $C_{21}H_{24}FN_5O_3.C_2H_2O_4$: C, 54.86; H, 5.20; Found: C, 54.71; H, 5.30; N, 13.93%;

substituting 1-(2-oxazol-2-ylphenyl)piperazine and 3-(3-chloropropyl)-5-methyl-2,4(1H,3H)-pyrimidinedione and recrystallizing from a solution of oxalic acid in alcohol gave 3-{3-[4-(2-oxazol-2-ylphenyl)piperazin-1-yl]propyl}-5-methyl-2,4(1H,3H)-pyrimidinedione oxalate, m.p. 214°–215° C.; Anal.: Calcd. for $C_{21}H_{25}N_5O_3.C_2H_2O_4$: C, 55.13; H, 6.11; N, 13.851; Found: C, 55.22; H, 5.70; N, 14.15%;

substituting 3-(3-chloropropyl)-5-methyl-1-pyrid-2-ylmethyl-2,4(1H,3H)-pyrimidinedione and recrystallizing from a solution of fumaric acid in alcohol gave 3-{3-[4-(2-methoxyphenyl)piperazin-1-yl]propyl}-5-methyl-1-pyrid-2-ylmethyl-2,4(1H,3H)-pyrimidinedione fumarate as a foam; Anal.: Calcd. for $C_{25}H_{31}N_5O_3.(C_4H_4O_4)_5.(H_2O)_{0.25}$: C, 59.27; H, 6.02; N, 11.15%; Found: C, 59.25; H, 6.13; N, 11.27%;

substituting 1-(4-fluoro-2-methoxyphenyl)piperazine and 3-(3-chloropropyl)-6-methyl-2,4(1H,3H)-pyrimidinedione gave 3-{3-[4-(4-fluoro-2-methoxyphenyl)piperazin-1-yl]propyl}-6-methyl-2,4(1H,3H)-pyrimidinedione hydrochloride, m.p. 227°–229° C.; Anal.: Calcd. for $C_{19}H_{25}FN_4O_3.(HCl)_2$: C, 48.82; H, 6.20; N, 11.98%; Found: C, 48.72; H, 5.87; N, 11.72%;

substituting 2-(3-chloropropyl)-6-methyl-1,2,4-triazine-3,5(2H,4H)-dione and recrystallizing from a solution of fumaric acid in alcohol gave di(2-{3-[4-(2-methoxyphenyl)piperazin-1-yl]propyl}-6-methyl-1,2,4-triazine-3,5(2H,4H)-dione) fumarate, m.p. 235°–237° C.; Anal.: Calcd. for $(C_{18}H_{25}N_5O_3)_2.C_4H_4O_4$: C, 56.93; H, 6.57; N, 16.60%; Found: C, 56.97; H, 6.59; N, 16.54%;

substituting 1-[2-(2,2,2-trifluoroethoxy)phenyl]piperazine and 4-(3-chloropropyl)-6-methyl-1,2,4-triazine-3,5(2H,4H)-dione and recrystallizing from a solution of fumaric acid in alcohol gave di[4-(3-{4-[2-(2,2,2-trifluoroethoxy)phenyl]piperazin-1-yl}propyl)-6-methyl-1,2,4-triazine-3,5(2H,4H)-dione] fumarate, m.p. 242°–245° C.; Anal.: Calcd. for $(C_{19}H_{24}F_3N_5O_3)_2.C_4H_4O_4$: C, 51.48; H, 5.45; N, 14.29%; Found: C, 51.20; H, 5.29; N, 14.20%;

substituting 4-(3-chloropropyl)-6-methyl-1,2,4-triazine-3,5(2H,4H)-dione and recrystallizing from a solution of fumaric acid in alcohol gave 4-{3-[4-(2-methoxyphenyl)piperazin-1-yl]propyl}-6-methyl-1,2,4-triazine-3,5(2H,4H)-dione) fumarate, m.p. 204°–206° C.; Anal.: Calcd. for $C_{18}H_{25}N_5O_3.C_4H_4O_4$: C, 54.54; H, 6.24; N, 14.45%; Found: C, 54.28; H, 6.38; N, 14.65%;

substituting 1-(4-fluoro-2-methoxyphenyl)piperazine and 4-(3-chloropropyl)-6-methyl-1,2,4-triazine-3,5(2H,4H)-dione and recrystallizing from a solution of fumaric acid in alcohol gave 4-{3-[4-(4-fluoro-2-methoxyphenyl)piperazin-1-yl]propyl}-6-methyl-1,2,4-triazine-3,5(2H,4H)-dione) fumarate, m.p. 193°–195° C.; Anal.: Calcd. for $C_{18}H_{25}N_5O_3.C_4H_4O_4$: C, 51.75; H, 5.90; N, 13.72%; Found: C, 51.93; H, 5.56; N, 13.91%;

substituting 1-(2-trifluoromethoxyphenyl)piperazine and 3-(3-chloropropyl)-5-ethyl-2,4(1H,3H)-pyrimidinedione and recrystallizing from a solution of hydrobromic acid in alcohol gave 3-{3-[4-(2-trifluoromethoxyphenyl)piperazin-1-yl]propyl}-5-ethyl-2,4(1H,3H)-pyrimidinedione hydrobromide, m.p. 64°–73° C.; Anal.: Calcd. for $C_{20}H_{25}F_3N_4O_3.(HBr)_{0.25}$: C, 53.78; H, 5.70; N, 12.54%; Found: C, 54.39; H, 6.09; N, 12.61%;

substituting 1-[4-fluoro-2-(2,2,2-trifluoroethoxy)phenyl]piperazine and 3-(3-chloropropyl)-5-ethyl-2,4(1H,3H)-pyrimidinedione gave 3-(3-{4-[4-fluoro-2-(2,2,2-trifluoroethoxyphenyl)piperazin-1-yl]propyl}-5-ethyl-2,4(1H,3H)-pyrimidinedione hydrochloride, m.p. 186°–188° C.; Anal.: Calcd. for $C_{21}H_{27}F_4N_4O_3.(HCl)_2$: C, 47.46; H, 5.31; N, 10.54%; Found: C, 47.67; H, 5.34; N, 10.64%;

substituting 1-[4-fluoro-2-(2,2,2-trifluoroethoxy)phenyl]piperazine and 3-(3-chloropropyl)-6-methyl-2,4(1H,3H)-pyrimidinedione gave 3-(3-{4-[4-fluoro-2-(2,2,2-trifluoroethoxyphenyl)piperazin-1-yl]propyl}-6-methyl-2,4(1H,3H)-pyrimidinedione hydrochloride, m.p. 225°–228° C.; Anal.: Calcd. for $C_{20}H_{24}F_4N_4O_3.(HCl)_2$: C, 46.12; H, 5.06; N, 10.83%; Found: C, 46.28; H, 4.98; N, 10.66%;

substituting 1-[2-(2,2,2-trifluoroethoxy)phenyl]piperazine and 1-(1-benzyl-5-methyl-2,4-dioxo-(1H,3H)-pyrimidin-3-ylmethyl)cycloprop-1-ylmethyl methanesulfonate gave 1-benzyl-3-(1-{4-[2-(2,2,2-trifluoroethoxy)phenyl]piperazin-1-ylmethyl}cycloprop-1-ylmethyl)-5-methyl-2,4(1H,3H)-pyrimidinedione as an oil;

substituting 1-(4-fluoro-2-methoxyphenyl)piperazine and 1-benzyl-3-(3-chloropropyl)-5,5-dimethyl-2,4,6(1H,3H,5H)-pyrimidinetrione and recrystallizing from a solution of fumaric acid in alcohol gave 1-benzyl-3-{3-[4-(4-fluoro-2-methoxyphenyl)piperazin-1-yl]propyl}-5,5-dimethyl-2,4,6(1H,3H,5H)-pyrimidinetrione fumarate, m.p. 168°–169° C.; Anal.: Calcd. for $C_{27}H_{33}FN_4O_4.(C_4H_4O_4)_{0.5}.(H_2O)_{0.5}$: C, 61.80; H, 6.44; N, 9.94%; Found: C, 61.72; H, 6.25; N, 10.02%;

substituting 1-[2-(2,2,2-trifluoroethoxy)phenyl]piperazine and 1-benzyl-3-(3-chloropropyl)-5,5-dimethyl-2,4,6(1H,3H,5H)-pyrimidinetrione and recrystallizing from a solution of fumaric acid in alcohol gave 1-benzyl-3-(3-{4-[2-(2,2,2-trifluoroethoxy)phenyl]piperazin-1-yl}propyl)-5,5-dimethyl-2,4,6(1H,3H,5H)-pyrimidinetrione fumarate, m.p. 176°–177° C.; Anal.: Calcd. for $C_{28}H_{33}F_3N_4O_4.C_4H_4O_4$: C, 58.00; H, 5.63; N, 8.45%; Found: C, 58.20; H, 5.62; N, 8.48%;

substituting 1-benzyl-3-(3-chloropropyl)-5,5-dimethyl-2,4,6 (1H,3H,5H)-pyrimidinetrione and recrystallizing from a solution of fumaric acid in alcohol gave 1-benzyl-3-{3-[4-(2-methoxyphenyl)piperazin-1-yl]propyl}-5,5-dimethyl-2,4,6(1H,3H,5H)-pyrimidinetrione fumarate, m.p. 184° C.; Anal.: Calcd. for $C_{27}H_{34}N_4O_4.C_4H_4O_4.(CH_4O)_{0.5}$: C, 61.95; H, 6.60; N, 9.171%; Found: C, 62.00; H, 6.89; N, 9.45%;

substituting 1-[2-(2,2,2-trifluoroethoxy)phenyl]piperazine and 1-(3-chloropropyl)-3-(4-fluorophenyl)-5-methyl-2,4 (1H,3H)-pyrimidinedione gave 1-(3-{4-[2-(2,2,2-trifluoroethoxy)phenyl]piperazin-1-yl}propyl)-3-(4-fluorophenyl)-5-methyl-2,4(1H,3H)-pyrimidinedione hydrochloride, m.p. 220°–222° C.; Anal.: Calcd. for $C_{26}H_{28}F_4N_4O_3.(HCl)_2.(H_2O)_{0.1}$: C, 52.46; H, 5.11; N, 9.41%; Found: C, 52.21; H, 4.91; N, 9.26%;

substituting 1-(4-fluoro-2-methoxyphenyl)piperazine and 3-(3-chloropropyl)-1-pyrid-4-ylmethyl-5-methyl-2,4(1H,3H)-pyrimidinedione and recrystallizing from a solution of fumaric acid in alcohol gave 3-{3-[4-(4-fluoro-2-methoxyphenyl)piperazin-1-yl]propyl}-1-pyrid-4-ylmethyl-5-methyl-2,4(1H,3H)-pyrimidinedione fumarate as a foam; Anal.: Calcd. for $C_{25}H_{30}FN_5O_3.(C_4H_4O_4)_{1.5}$: C, 58.03; H, 5.65; N, 10.91%; Found: C, 57.92; H, 5.71; N, 11.00%;

substituting 1-[2-(2,2,2-trifluoroethoxy)phenyl]piperazine and 3-(3-chloropropyl)-1-(4-fluorophenyl)-5-methyl-2,4 (1H,3H)-pyrimidinedione gave 3-(3-{4-[2-(2,2,2-trifluoroethoxy)phenyl]piperazin-1-yl}propyl)-1-(4-fluorophenyl)-5-methyl-2,4(1H,3H)-pyrimidinedione hydrochloride, m.p. 166°–168° C.; Anal.: Calcd. for $C_{26}H_{28}F_4N_4O_3HCl.(C_4H_{10}O)_{0.3}$: C, 56.34; H, 5.56; N, 9.66%; Found: C, 56.06; H, 5.76; N, 9.36%;

substituting 1-(2-pyrrol-1-ylphenyl)piperazine and 3-(3-chloropropyl)-5-methyl-2,4(1H,3H)-pyrimidinedione gave 3-{3-[4-(2-pyrrol-1-ylphenyl)piperazin-1-yl]propyl}-5-methyl-2,4(1H,3H)-pyrimidinedione hydrobromide, m.p. 249°–252° C.; Anal.: Calcd. for $C_{22}H_{27}N_5O_2.HBr$: C, 55.60; H, 5.95; N, 14.80%; Found: C, 55.49; H, 6.10; N, 14.04%;

substituting 1-[2-(2,2,2-trifluoroethoxy)phenyl]piperazine and 3-(3-chloropropyl)-5-methyl-2,4-dioxo-(1H,3H)-pyrimidin-1-ylmethylpyridine 1-oxide gave 3-(3-{4-[2-(2,2,2-trifluoroethoxy)phenyl]piperazin-1-yl}propyl)-5-methyl-2,4-dioxo-(1H,3H)-pyrimidin-1-ylmethylpyridine 1-oxide fumarate, m.p. 120°–122° C. Anal.: Calcd. for $C_{26}H_{30}F_3N_5O_4.(C_4H_4O_4)_{1.5}$: C, 54.31; H, 5.13; N, 9.906%; Found: C, 54.55; H, 5.15; N, 9.93%;

substituting 1-(4-fluoro-2-methoxyphenyl)piperazine and 3-(3-chloropropyl)-1-(2,2,2-trifluoroethoxy)-5-methyl-2,4(1H,3H)-pyrimidinedione gave 3-{3-[4-(4-fluoro-2-methoxyphenyl)piperazin-1-yl]propyl}-1-(2,2,2-trifluoroethoxy)-5-methyl-2,4(1H,3H)-pyrimidinedione hydrobromide, m.p. 179°–181° C.; Anal.: Calcd. for $C_{21}H_{26}F_4N_4O_3.HBr$: C, 46.76; H, 5.05; N, 10.39%; Found: C, 47.13; H, 5.15; N, 10.21;

substituting 3-(3-chloropropyl)-1-[2-(trimethylsilyl)ethoxymethyl]-2,4(1H,3H)-pyrimidinedione gave 3-(3-{4-[2-(2,2,2-trifluoroethoxy)phenyl]piperazin-1-yl}propyl)-1-[2-(trimethylsilyl)ethoxymethyl]-2,4(1H,3H)-pyrimidinedione;

substituting 1-[4-fluoro-2-(2,2,2-trifluoroethoxy)phenyl] piperazine and 3-(3-chloropropyl)-1-[2-(trimethylsilyl) ethoxymethyl]-2,4(1H,3H)-pyrimidinedione gave 3-(3-{4-[4-fluoro-2-(2,2,2-trifluoroethoxy)phenyl]piperazin-1-yl}propyl)-1-[2-(trimethylsilyl)ethoxymethyl]-2,4(1H, 3H)-pyrimidinedione;

substituting 1-[2-(2,2,2-trifluoroethoxy)phenyl]piperazine and 2-(3-chloropropyl)-6-methyl-4-[2-(trimethylsilyl) ethoxymethyl]-1,2,4-triazine-3,5(2H,4H)-dione gave 2-(3-{4-[2-( 2,2,2-trifluoroethoxy)phenyl]piperazin-1-yl}propyl)-6-methyl-4-[2-(trimethylsilyl)ethoxymethyl]-1,2,4-triazine-3,5(2H,4H)-dione;

substituting 1-(4-fluoro-2-methoxyphenyl)piperazine and 2-(3-chloropropyl)-6-methyl-4-[2-(trimethylsilyl) ethoxymethyl]-1,2,4-triazine-3,5(2H,4H)-dione gave 2-{3-[4-(4-fluoro-2-methoxyphenyl)piperazin-1-yl] propyl}-6-methyl-4-[2-(trimethylsilyl)ethoxymethyl]-1, 2,4-triazine-3,5(2H,4H)-dione;

substituting 1-[4-fluoro-2-(2,2,2-trifluoroethoxy)phenyl] piperazine and 3-(3-chloropropyl)-5-hydroxymethyl-1-[2-(trimethylsilyl)ethoxymethyl]-2,4(1H,3H)-pyrimidinedione gave 3-(3-{4-[4-fluoro-2-(2,2,2-trifluoroethoxy)phenyl]piperazin-1-yl}propyl)-5-hydroxymethyl-1-[2-(trimethylsilyl)ethoxymethyl]-2,4 (1H,3H)-pyrimidinedione;

substituting 1-(2-chlorophenyl)piperazine and 3-(3-chloropropyl)-5-methyl-1-[2-(trimethylsilyl) ethoxymethyl]-2,4(1H,3H)-pyrimidinedione gave 3-{3-[4-(2-chlorophenyl)piperazin-1-yl]propyl}-5-methyl-1-[2-(trimethylsilyl)ethoxymethyl]-2,4(1H,3H)-pyrimidinedione;

substituting 1-[4-fluoro-2-(2,2,2-trifluoroethoxy)phenyl] piperazine and 3-(3-chloropropyl)-5-fluoro-1-[2-(trimethylsilyl)ethoxymethyl]-2,4(1H,3H)-pyrimidinedione gave 3-(3-{4-[4-fluoro-2-(2,2,2-trifluoroethoxy)phenyl]piperazin-1-yl}propyl)-5-fluoro-1-[2-(trimethylsilyl)ethoxymethyl]-2,4(1H,3H)-pyrimidinedione;

substituting 1-[2-(4-fluoro-2,2,2-trifluoroethoxy)phenyl] piperazine and 3-(3-chloropropyl)-5-chloro-1-[2-(trimethylsilyl)ethoxymethyl]-2,4(1H,3H)-pyrimidinedione gave 3-(3-{4-[4-fluoro-2-(2,2,2-trifluoroethoxy)phenyl]piperazin-1-yl}propyl)-5-chloro-1-[2-trimethylsilyl)ethoxymethyl]-2,4(1H,3H)-pyrimidinedione;

substituting 1-[4-fluoro-2-(2,2,2-trifluoroelhoxy)phenyl] piperazine and 1-[2-(trimethylsilyl)ethoxymethyl]-5-methoxy-2,4(1H,3H)-pyrimidinedione gave 3-(3-{4-[4-fluoro-2-(2,2,2-trifluoroethoxy)phenyl]piperazin-1-yl}propyl)-1-(2-(trimethylsilyl)ethoxymethyl)-5-methoxy-2,4(1H,3H)-pyrimidinedione as an oil;

substituting 1-[2-(2,2,2-trifluoroethoxy)phenyl]piperazine and 1-[2-(trimethylsilyl)ethoxymethyl]-5-hydroxymethyl-2,4(1H,3H)-pyrimidinedione gave 3-(3-{4-[2-(2,2,2-trifluoroethoxy)phenyl]piperazin-1-yl}propyl)-1-[2-(trimethylsilyl)ethoxymethyl]-5-hydroxymethyl-2,4(1H,3H)-pyrimidinedione as an oil; and substituting 1-[4-fluoro-2-($^2$,$^2$,$^2$-trifluoroethoxy)phenyl] piperazine and 2-(3-chloropropyl)-6-methyl-4-[2-(trimethylilyl)ethoxymethyl]-1,2,4-triazine-3,5(2H,4H)-dione gave 2-(3-{4-[4-fluoro-2-(2,2,2-trifluoroethoxy) phenyl]piperazin-1-yl}propyl)-6-methyl-4-[2-(trimethylsilyl)ethoxymethyl]-1,2,4-triazine-3,5(2H,4H)-dione.

Example 26

3-(3-{4-[4-Fluoro-2-(2,2,2-trifluoroethoxy)phenyl] piperazin-1-yl}propyl)-5-dimethylamino-1-[2-(trimethylsilyl)ethoxymethyl]-2,4(1H,3H)-pyrimidinedione The following is the preparation of a protected derivative of a compound of Formula I in which $R^1$ is 2,2,2- trifluoroethoxy, $R^2$ is fluoro at the 4-position, $R^3$ and $R^4$ are each hydro and $R^5$ is a group of Formula (a) wherein Z is CH, $R^7$ is dimethyl amino and the protective group is 2-(trimethylsilyl)ethoxymethyl.

A mixture of 3-(3-{4-[4-fluoro-2-(2,2,2-trifluoroethoxy) phenyl]piperazin-1-yl}propyl)-5-chloro-1-[2-(trimethylsilyl)ethoxymethyl]-2,4(1H,3H)-pyrimidinedione (0.5 g, 0.84 mmol), prepared as in Example 25, aqueous dimethylamine (40%, 3 mL) and ethanol (3 mL) was heated in a sealed tube 3 hours at 130° C. The reaction mixture was concentrated and the residue was purified by column chromatography on silica gel eluting with methylene chloride/methanol (95:5+3% ammonium hydroxide) to give 3-(3-{4-[4-fluoro-2-(2,2,2-trifluoroethoxy)phenyl]piperazin-1-yl}propyl)-5-dimethylamino-1-[2-(trimethylsilyl) ethoxymethyl]-2,4(1H,3H)-pyrimidinedione (0.26 g, 0.44 mmol).

Example 27

3-{3-[4-(2-(2,2,2-Trifluoroethoxyphenyl)piperazin-1-yl] propyl}-2,4(1H,3H)-pyrimidinedione The following is the preparation of a compound of Formula I in which $R^1$ is 2,2,2-trifluoroethoxy, $R^2$, $R^3$ and $R^4$ are each hydro and $R^5$ is a group of Formula (a) wherein Z is CH and $R^6$ and $R^7$ are each hydro.

A mixture of the 3-(3-{4-[2-(2,2,2-trifluoroethoxy) phenyl]piperazin-1-yl}-propyl)-1-[2-(trimethylsilyl) ethoxymethyl]-2,4(1H,3H)-pyrimidinedione (273 mg, 0.5 mmol), prepared as in Example 25, tetrabutylammonium fluoride (2 mmol) and THF (5 mL) was stirred 24 hours at 25° C. The reaction mixture then was concentrated and the residue was purified by column chromatography on silica gel eluting with ethyl acetate to give 3-(3-{4-[2-(2,2,2-trifluoroethoxy)phenyl]piperazin-1-yl}propyl)-2,4(1H,3H)-pyrimidinedione (160 mg, 0.39 mmol). The free base was recrystallized from a solution of hydrogen chloride in ethanol to give 3-(3-{4-[2-(2,2,2-trifluoroethoxy)phenyl] piperazin-1-yl}propyl)-2,4(1H,3H)-pyrimidinedione hydrochloride, m.p. 247°–249° C. Anal.: Calcd. for $C_{19}H_{23}F_3N_4O_3$.(HCl)$_2$: C, 47.01; H, 5.19; N, 11.54%; Found: C, 46.84; H, 5.18; N, 11.34%.

Proceeding as in Example 27, but substituting a different starting material for 3-(3-{4-[2-(2,2,2-trifluoroethoxy) phenyl]piperazin-1-yl}propyl)-1-[2-(trimethylsilyl) ethoxymethyl]-2,4(1H,3H)-pyrimidinedione gave the following compounds of Formula I:

substituting 3-(3-{4-[4-fluoro-2-(2,2,2-trifluoroethoxy) phenyl]piperazin-1-yl}-propyl)-1-[2-(trimethylsilyl) ethoxymethyl]-2,4(1H,3H)-pyrimidinedione and recrystallizing from a solution of fumaric acid in alcohol gave 3-(3-{4-[4-fluoro-2-(2,2,2-trifluoroethoxy)phenyl] piperazin-1-yl}propyl)-2,4(1H,3H)-pyrimidinedione fumarate, m.p. 187° C. Anal.: Calcd. for $C_{19}H_{22}F_4N_4O_3.C_4H_4O_4$: C, 50.55; H, 4.80; N, 10.25%; Found: C, 50.46; H, 4.75; N, 10.13%;

substituting 2-(3-{4-[2-(2,2,2-trifluoroethoxy)phenyl] piperazin-1-yl}propyl)-6-methyl-4-[2-(trimethylsilyl) ethoxymethyl]-1,2,4-triazine-3,5(2H,4H)-dione and recrystallizing from a solution of fumaric acid in alcohol gave di[2-(3-{4-[2-(2,2,2-trifluoroethoxy)phenyl] piperazin-1-yl}propyl)-6-methyl-1,2,4-triazine-3,5(2H,4H)-dione] fumarate, m.p. 213°–215° C.; Anal.: Calcd. for $(C_{19}H_{24}F_3N_5O_3)_2.C_4H_4O_4$: C, 51.96; H, 5.40; N, 14.43%; Found: C, 52.23; H, 5.38; N, 14.35%;

substituting 2-{3-[4-(4-fluoro-2-methoxyphenyl)piperazin-1-yl]propyl}-6-methyl-4-[2-(trimethylsilyl) ethoxymethyl]-1,2,4-triazine-3,5(2H,4H))-dione and recrystallizing from a solution of fumaric acid in alcohol gave 2-{3-[4-(4-fluoro-2-methoxyphenyl)piperazin-1-yl] propyl}-6-methyl-1,2,4-triazine-3,5(2H,4H)-dione fumarate, m.p. 201°–203° C.;

substituting 3-(3-{4-[4-fluoro-2-(2,2,2-trifluoroethoxy) phenyl]piperazin-1-yl}-propyl)-5-hydroxymethyl-1-[2-(trimethylsilyl)ethoxymethyl]-2,4(1H,3H)-pyrimidinedione and recrystallizing from a solution of fumaric acid in alcohol gave 3-(3-{4-[4-fluoro-2-(2,2,2-trifluoroethoxy)phenyl]piperazin-1-yl}propyl)-5-hydroxymethyl-2,4(1H,3H)-pyrimidinedione fumarate, m.p. 181° C.; Anal.: Calcd. for $C_{20}H_{24}F_4N_4O_4.(C_4H_4O_4)_{0.5}$: C, 50.18; H, 5.49; N, 10.18%; Found: C, 49.98; H, 5.49; N, 10.01%;

substituting 3-{3-[4-(2-chlorophenyl)piperazin-1-yl] propyl}-5-methyl-1-[2-(trimethylsilyl)ethoxymethyl]-2,4 (1H,3H)-pyrimidinedione gave 3-{3-[4-(2-chlorophenyl) piperazin-1-yl]propyl}-5-methyl-2,4(1H,3H)-pyrimidinedione hydrochloride, m.p. 240°–242° C.; Anal.: Calcd. for $C_{18}H_{23}ClN_4O_2.HCl.(H_2O)_{0.75}$: C, 52.37; H, 6.23; N, 13.57%; Found: C, 52.14; H, 6.03; N, 13.54%;

substituting 3-(3-{4-[4-fluoro-2-(2,2,2-trifluoroethoxy) phenyl]piperazin-1-yl}-propyl)-5-fluoro-1-[2-(trimethylsilyl)ethoxymethyl]-2,4(1H,3H)-pyrimidinedione gave 3-(3-{4-[4-fluoro-2-(2,2,2-trifluoroethoxy)phenyl]piperazin-1-yl}propyl)-5-fluoro-2,4(1H,3H)-pyrimidinedione hydrochloride, m.p. 187°–189° C.; Anal.: Calcd. for $C_{19}H_{21}F_5N_4O_3.(HCl)_2$: C, 43.77; H, 4.44; N, 10.74%; Found: C, 43.52; H, 4.35; N, 10.83%;

substituting 3-(3-{4-[4-fluoro-2-(2,2,2-trifluoroethoxy) phenyl]piperazin-1-yl}-propyl)-5-chloro-1-[2-(trimethylsilyl)ethoxymethyl]-2,4(1H,3H)-pyrimidinedione and recrystallizing from a solution of fumaric acid in alcohol gave 3-(3-{4-[4-fluoro-2-(2,2,2-trifluoroethoxy)phenyl]piperazin-1-yl}propyl)-5-chloro-2,4(1H,3H)-pyrimidinedione fumarate, m.p. 210°–212° C.; Anal.: Calcd. for $C_{19}H_{21}F_4N_4O_3.C_4H_4O_4.(CH_4O)_{0.5}$: C, 47.28; H, 4.56; N, 9.39%; Found: C, 47.44; H, 4.28; N, 9.08%;

substituting 3-(3-{4-[4-fluoro-2-(2,2,2-trifluoroethoxy) phenyl]piperazin-1-yl}-propyl)-5-dimethylamino-1-[2-(trimethylsilyl)ethoxymethyl]-2,4(1H,3H)-pyrimidinedione and recrystallizing from a solution of fumaric acid in alcohol gave 3-(3-{4-[4-fluoro-2-(2,2,2-trifluoroethoxy)phenyl]piperazin-1-yl}propyl)-5-dimethylamino-2,4(1H,3H)-pyrimidinedione fumarate, m.p. 182°–184° C.; Anal.: Calcd. for $C_{21}H_{27}F_4N_5O_3.C_4H_4O_4$: C, 50.93; H, 5.30; N 11.88%; Found: C, 50.82; H, 5.35; N, 11.62%;

substituting 3-(3-{4-[4-fluoro-2-(2,2,2-trifluoroethoxy) phenyl]piperazin-1-yl}-propyl)-1-[2-(trimethylsilyl) ethoxymethyl]-5-methoxy-2,4(1H,3H)-pyrimidinedione gave 3-(3-{4-[4-fluoro-2-(2,2,2-trifluoroethoxy)phenyl] piperazin-1-yl}propyl)-5-methoxy-2,4(1H,3H)-pyrimidinedione hydrochloride, m.p. 188°–189° C.; Anal.: Calcd. for $C_{20}H_{24}F_4N_4O_4.(HCl)_2$: C, 45.04; H, 4.91; N, 10.51%; Found: C, 44.88; H, 4.87; N, 10.40%;

substituting 3-(3-{4-[2-(2,2,2-trifluoroethoxy)phenyl] piperazin-1-yl}propyl)-1-[2-(trimethylsilyl) ethoxymethyl]-5-hydroxymethyl-2,4(1H,3H)-pyrimidinedione and recrystallizing from a solution of fumaric acid in alcohol gave 3-(3-{4-[2-(2,2,2-trifluoroethoxy)phenyl]piperazin-1-yl}propyl)-5-hydroxymethyl-2,4(1H,3H)-pyrimidinedione fumarate, m.p. 143° C.; Anal.: Calcd. for $C_{20}H_{25}F_3N_4O_4.C_2H_2O_2$: C, 51.41; H, 5.34; N, 9.89%; Found: C, 51.15; H, 5.56; N, 10.29%; and substituting 2-(3-{4-[4-fluoro-2-(2,2,2-trii-luoroethoxy) phenyl]piperazin-1-yl}-propyl)-6-methyl-4-[2-(trimethylsilyl)ethoxymethyl]-1,2,4-triazine-3,5(2H,4H)-dione and recrystallizing from a solution of fumaric acid in alcohol gave 2-(3-{4-[4-fluoro-2-(2,2,2-trifluoroethoxy)phenyl]piperazin-1-yl}propyl)-6-methyl-1,2,4-triazine-3,5(2H,4H)-dione fumarate, m.p. 204°–206° C.; Anal.: Calcd. for $C_{19}H_{23}F_4N_5O_3 \cdot (C_4H_4O_4)_{0.5}$: C, 49.63; H, 4.92; N, 13.15%; Found: C, 49.03; H, 5.12; N, 13.19%.

Example 28

1-Bromo-3-{4-[2-(2,2,2-trifluoroethoxy)phenyl]piperazin-1-yl}propane

The following is the preparation of a compound of Formula 5 in which is bromo, $R^1$ is 2,2,2-trifluoroethoxy and $R^2$, $R^3$ and $R^4$ are each hydro.

A mixture of 4-[2-(2,2,2-trifluoroethoxy)phenyl] piperazine (2.37 g, 9.1 mmol), 1-bromo-3-chloropropane (14.34 g, 9 mL, 91.1 mmol), potassium carbonate (1.88 g, 13.6 mmol) and acetonitrile (40 mL) was heated 16 hours at reflux under argon. The reaction mixture was allowed to cool to 25° C., then filtered and concentrated in vacuo. The residue was further concentrated at 60° C. in vacuo to remove excess 1-bromo-3-chloropropane. The residue was purified by flash chromatography on silica gel eluting with hexane/ethyl acetate (1:1) to give a mixture of 1-chloro- and 1-bromo-3-{4-[2-(2,2,2-trifluoroethoxy)phenyl]piperazin-1-yl}propane (1.4 g).

Example 29

1-Chloro-2,2-dimethyl-3-{4-[2-(2,2,2-trifluoroethoxy) phenyl]piperazin-1-yl}propane The following is the preparation of a compound of Formula 5 in which L is chloro, $R^1$ is 2,2,2-trifluoroethoxy and $R^2$ is hydro and $R^3$ and $R^4$ are each methyl.

A mixture of ethyl cyanoacetate (5 g, 4 mL, 44 mmol), triethylbenzylammonium chloride (10.05 g, 44 mmol), iodomethane (11 mL, 177 mmol) and 50% sodium hydroxide (88 mL) was stirred 2 hours at 20° C. The reaction mixture then was diluted with water (220 mL) and the aqueous phase was separated, washed with diethyl ether, treated with concentrated hydrochloric acid and extracted with diethyl ether (3×50 mL). The combined extracts were washed with brine (1×50 mL), dried (MgSO$_4$) and concentrated to give 2-cyano-2-methylpropionic acid (4.3 g, 37.5 mmol).

A mixture of 2-cyano-2-methylpropionic acid (4.1 g, 36.1 mmol), dry triethylamine (6.6 mL, 46.9 mmol) and THF (70 mL) was cooled to between −5° and 0° C. under argon and methyl chloroformate (3.4 mL, 43.3 mmol) was added. The mixture was stirred 1 hour, filtered at 0° C. (washing through with THF), and recooled to 0° C. under argon and then a mixture of sodium borohydride (4.1 g, 108 mmol) and cold water (25 mL) was added at a rate such that the reaction mixture remained below 10° C. The mixture was stirred 2.5 hours at 20° C., treated with 10% hydrochloric acid, washed with brine (1×40 mL) and extracted with ethyl acetate (4×40 mL). The combined extracts were washed with brine, dried (MgSO$_4$) and concentrated. The residue was purified by chromatography on silica gel eluting with hexanes/ethyl acetate (7:3) to give 3-hydroxy-2,2-dimethylpropanenitrile (2.7 g, 27.1 mmol).

A solution of 60% sodium hydride (367.1 mg, 15.3 mmol) was washed with hexane (3×2 mL) and suspended in DMF (2 mL). The suspension was cooled to −10° C. and then a mixture of 3-hydroxy-2,2-dimethylpropanenitrile (1.4 g, 13.9 mmol) and DMF (8 mL) was added. The mixture was cooled 2.5 hour with stirring stirred at −10° to −5° C. and then benzyl bromide (1.7 mL, 13.9 mmol) was added. The mixture was cooled 2 hours with stirring at −5° C., diluted with water (10 mL) and extracted with diethyl ether (3×10 mL). The combined extracts were washed with water (1×10 mL) and brine (1×10 mL), dried (MgSO$_4$) and concentrated to give 3-benzyloxy-2,2-dimethylpropanenitrile (2.5 g, 13.2 mmol).

A mixture of 3-benzyloxy-2,2-dimethylpropanenitrile (2.5 g, 13.2 mmol), 10% aqueous sodium hydroxide (10 mL) and methanol (150 mL) was heated 8 hours at reflux and then concentrated. The residue was dissolved in water (30 mL) and the solution was washed with dichloromethane (2×10 mL), treated with 10% hydrochloric acid and extracted with ethyl acetate (4×20 mL). The combined extracts were washed with water and brine, dried (MgSO$_4$) and concentrated to give 3-benzyloxy-2,2-dimethylpropionic acid (1.6 g, 7.5 mmol).

A mixture of 3-benzyloxy-2,2-dimethylpropionic acid (1.6 g, 7.5 mmol), benzene (10 mL) and DMF (2 drops) was cooled to between 0° and 5° C. and then oxalyl chloride (0.98 mL, 11.2 mmol) was added slowly. The mixture was stirred 1.5 hours at between 20° and 25° C. and concentrated. The residue was dissolved in benzene (10 mL) and the solution reconcentrated (repeated once). The residue then was dissolved in benzene (6 mL) and the solution was cooled to 0° C. and added to a cold (0° C.) mixture of 1-[2-(2,2,2-trifluoroethoxy)phenyl]piperazine (2.1 g, 8.24 mmol) and benzene (6 mL). The mixture was cooled 15 hours at 0° C. and then triethylamine (3 mL, 21.3 mmol) was added. The mixture was stirred an additional 20 minutes, diluted with 10 mL of saturated sodium carbonate and extracted with methylene chloride (3×15 mL). The combined extracts were washed with water (1×10 mL), dried (MgSO$_4$) and concentrated. The residue was purified by chromatography on silica gel eluting with hexanes/ethyl acetate (8:2) to give 3-benzyloxy-2,2-dimethyl-1-{4-[2-(2,2,2-trif-luoroethoxy)phenyl]piperazin-1-yl}-1-propanone (2.8 g, 6.4 mol).

A suspension of lithium aluminum hydride (0.49 g, 12.8 mmol) and THF (5 mL) was cooled to 0° C. and added to a solution of 3-benzyloxy- 2,2-dimethyl-1-{4-[2-(2,2,2-trifluoroethoxy)phenyl]piperazin-1-yl}-1-propanone (2.8 g, 6.4 mol) in 12 mL of THF. The mixture was heated 2 hours at reflux, slowly diluted with water, filtered and concentrated. The residue was dissolved in water and the solution was extracted with methylene chloride (4×30 mL). The combined extracts were washed with water (1×25 mL), dried (MgSO$_4$) and concentrated. The residue was purified by chromatography on silica gel eluting with hexanes/ethyl acetate (8:2) to give 3-benzyloxy-2,2-dimethyl-1-{4-[2-(2,2-trifluoroethoxy)phenyl]piperazin-1-yl}propane (2.6 g, 6.2 mol).

A mixture of 3-benzyloxy-2,2-dimethyl-1-(4-[2-(2,2,2-trifluoroethoxy)phenyl]piperazin-1-yl)propane (2.5 g, 6 mol), 10% palladium on carbon (2.8 g), ammonium formate (3.8 g, 59.6 mmol) and methanol (130 mL) was heated 1 hour at reflux. The reaction mixture was allowed to cool to approximately 25° C., then filtered over celite (washing through with methanol and saturated sodium carbonate (20 mL)) and concentrated. The residue was dissolved in water and the solution was extracted with methylene chloride (3×20 mL). The combined extracts were dried (MgSO$_4$) and concentrated. The residue was purified by chromatography on silica gel eluting with hexanes/ethyl acetate (8:2) to give 2,2-dimethyl-3-{4-[2-(2,2,2-trifluoroethoxy)phenyl] piperazin-1-yl}-1-propanol (1.6 g, 5.1 mol).

A mixture of 2,2-dimethyl-3-{4-[2-(2,2,2-trifluoroethoxy)phenyl]piperazin-1-yl}-1-propanol (991 mg, 2.9 mol), triethylamine (0.4 mL, 2.9 mmol), p-toluenesulfonyl chloride (678 mg, 3.4 mmol), 4-dimethylaminopyridine (35 mg, 0.29 mmol) and methylene chloride (15 mL) was stirred 8 hours at 20° to 25° C. The reaction mixture then was filtered and concentrated and the residue was purified by chromatography on silica gel eluting with hexanes/ethyl acetate (95:5) to give 1-chloro-2,2-dimethyl-3-{4-[2-(2,2,2-trifluoroethoxy)phenyl]piperazin-1-yl}propane (238 mg, 0.67 mol).

Example 30

3-(3-{4-[2-(2,2,2-Trifluoroethoxy)phenyl]piperazin-1-yl}propyl]-5,6,7,8-tetrahydro-2,4(1H,3H)-quinazolinedione The following is the preparation of a compound of Formula I in which $R^1$ is methoxy, $R^2$, $R^3$ and $R^4$ are each hydro and $R^5$ is a group of Formula (a) wherein Z is $C(R^9)$, $R^6$ is benzyl and $R^7$ and $R^9$ together are tetramethylene.

A mixture of 5,6,7,8-tetrahydro-2,4(1H,3H)-quinazolinedione (665 mg, 4 mmol), 1-chloro- and 1-bromo-3-{4-[2-(2,2,2-trifluoroethoxy)phenyl]piperazin-1-yl}propane (1.4 g), prepared as in Example 28, potassium carbonate (552 mg, 4 mmol) and dry DMF (20 mL) was heated 16 hours at 65° C. under argon. The reaction mixture then was cooled to 25° C., filtered, washed with methylene chloride and concentrated at 70° C. in vacuo. The residue was purified by preparative thin layer chromatography on silica gel eluting with methylene chloride/methanol (95:5) to give 3-(3-{4-[2-(2,2,2-trifluoroethoxy)phenyl]piperazin-1-yl}propyl)-5,6,7,8-tetrahydro-2,4(1H,3H)quinazolinedione (838 mg, 1.8 mmol), m.p. 148°–150° C. Anal.: Calcd. for $C_{23}H_{30}F_3N_4O_3 \cdot HCl \cdot (H_2O)_{2.5}$: C, 49.56; H, 5.97; N, 10.05%; Found: C, 47.26; H, 5.90; N, 9.55.

Proceeding as in Example 30, but substituting a different starting material for 1-chloro- and 1-bromo-3-{4-[2-(2,2,2-trifluoroethoxy)phenyl]piperazin-1-yl}propane gave the following compounds of Formula I:

substituting 1-chloro- and 1-bromo-3-[4-(4-fluoro-2-methoxyphenyl)piperazin-1-yl]propane gave 3-{3-[4-(4-fluoro-2-methoxyphenyl)piperazin-1-yl]-propyl}-5,6,7,8-tetrahydro-2,4(1H,3H)quinazolinedione, m.p. 230°–232° C.; Anal.: Calcd. for $C_{20}H_{29}FN_4O_3 \cdot (HCl)_2 \cdot (H_2O)_{0.5}$: C, 53.99; H, 6.38; N, 11.45% Found: C, 52.75; H, 6.28; N, 11.03; and substituting 1-chloro- and 1-bromo-3-[4-(2-methoxyphenyl)piperazin-1-yl]propane gave 3-{3-[4-(2-methoxyphenyl)piperazin-1-yl]propyl}-5,6,7,8-tetrahydro-2,4(1H,3H)quinazolinedione, m.p. 212°–214° C.; Anal.: Calcd. for $C_{22}H_{30}N_4O_3 \cdot (HCl)_2 \cdot (H_2O)_{0.3}$: C, 55.41; H, 6.89; N, 11.75%; Found C, 55.19; H, 6.95; N, 11.55.

Example 31

1-Benzyl-3-{3-[4-(2-methoxyphenyl)piperazin-1-yl]propyl}-5-hydroxyiminomethyl-2,4(1H,3H)-pyrimidinedione The following is the preparation of a compound of Formula I in which $R^1$ is methoxy, $R^2$, $R^3$ and $R^4$ are each hydro and $R^5$ is a group of Formula (a) wherein Z is CH, $R^6$ is benzyl and $R^7$ is hydroxyiminomethyl.

A mixture of 1-bromo-3-[4-(2-methoxyphenyl)piperazin-1-yl]propane (1.09 g, 3.5 mmol), prepared as in Example 25, 1-benzyl-5-hydroxyiminomethyl-2,4(1H,3H)-pyrimidinedione (0.86 g, 3.5 mmol), tetrabutylammonium fluoride (4.5 g, 17.5 mmol) and acetonitrile (50 mL) was stirred 24 hours at 25° C. The reaction mixture then was concentrated in vacuo and the residue was dissolved in ethyl acetate (50 mL). The solution was washed with water (3×50 mL) and brine (1×50 mL) and purified by preparative thin, layer chromatography on silica gel eluting with methylene chloride/methanol (95:5) and 1% ammonium hydroxide to give 1-benzyl-3-{3-[4-(2-methoxyphenyl)piperazin-1-yl]propyl}-5-hydroxyiminomethyl-2,4(1H,3H)-pyrimidinedione (250 mg, 0.6mmol). The free base was recrystallized from a solution of fumaric acid in alcohol to give 1-benzyl-3-{3-[4-(2-methoxyphenyl)piperazin-1-yl]propyl}-5-hydroxyiminomethyl-2,4(1H,3H)-pyrimidinedione fumarate, m.p. 198°–200° C.; Anal.: Calcd. for $C_{26}H_{31}N_5O_4 \cdot C_4H_4O_4$: C, 59.78; H, 6.02; N, 11.62%; Found: C, 59.74; H, 6.03; N, 11.83%.

Proceeding as in Example 31, but substituting a different starting material for 1-bromo-3-[4-(2-methoxyphenyl)piperazin-1-yl]propane and/or 1-benzyl-5-hydroxyiminomethyl-2,4(1H,3H)-pyrimidinedione gave the following compounds of Formula I:

substituting 1-chloro-3-{4-[4-fluoro-2-(2,2,2-trifluoroethoxy)phenyl]piperazin-1-yl}propane and 5,6-dihydro-2,4(1H,3H)-pyrimidinedione and recrystallizing from a solution of hydrochloric acid in alcohol gave 3-(3-{4-[4-fluoro-2-(2,2,2-trifluoroethoxy)phenyl]piperazin-1-yl}propyl)-5,6-dihydro-2,4(1H,3H)-pyrimidinedione hydrochloride, m.p. 186°–189° C.; Anal.: Calcd. for $C_{19}H_{24}F_4N_5O_3 \cdot (HCl)_2$: C, 44.10; H, 5.06; N, 10.83%; Found: C, 43.99; H, 5.16; N, 10.78%; and substituting 1-chloro-2,2-dimethyl-3-{4-[2-(2,2,2-trifluoroethoxy)phenyl]piperazin-1-yl}propane and 1-benzyl-5-methyl-2,4(1H,3H)-pyrimidinedione gave 1-benzyl-3-(3-{4-[2-(2,2,2-trifluoroethoxy)phenyl]piperazin-1-yl}-2,2-dimethylpropyl)-5-methyl-2,4(1H,3H)-pyrimidinedione.

Example 32

3-{3-[4-(2-methoxyphenyl)piperazin-1-yl]propyl}-5-methyl-2,4(1H,3H)-pyrimidinedione The following is the preparation of a compound of Formula I in which $R^1$ is methoxy, $R^2$, $R^3$ and $R^4$ are each hydro and $R^5$ is a group of Formula (a) wherein Z is CH, $R^6$ hydro and $R^7$ is methyl.

A mixture of 1-benzyl-3-{3-[4-(2-methoxyphenyl)piperazin-1-yl]propyl}-5-methyl-2,4(1H,3H)-pyrimidinedione (809 mg, 1.8 mmol), prepared as in Example 25, 10% palladium on carbon (800 mg) and of 0.1N ammonium formate (180 mL, 18 mmol in methanol) was heated 10 hours at reflux. The reaction mixture then was filtered and concentrated in vacuo. The residue was purified by column chromatography on silica gel (30 g) eluting with ethyl acetate to give 3-{3-[4-(2-methoxyphenyl)piperazin-1-yl]propyl}-5-methyl-2,4(1H,3H)-pyrimidinedione (459 mg, 1.28 mmol), m.p. 168°–170° C. The free base was recrystallized from a solution of hydrochloric acid in methanol to give 3-{3-[4-(2-methoxyphenyl)piperazin-1-yl]propyl}-5-methyl-2,4(1H,3H)-pyrimidinedione hydrochloride, m.p. 245°–248° C. Anal.: Calcd. for $C_{19}H_{26}N_4O_3 \cdot (HCl)_2$: C, 50.99; H, 6.71; N, 12.52%; Found: C, 51.06; H, 6.47; N, 12.58%.

Proceeding as in Example 32, but substituting other starting materials for 1-benzyl-3-{3-[4-(2-methoxyphenyl)piperazin-1-yl]propyl}-5-methyl-2,4(1H,3H)-pyrimidinedione, the following compounds of Formula I were prepared:

substituting 1-benzyl-3-(3-{4-[2-(2,2,2-trifluoroethoxy)phenyl]piperazin-1-yl}-propyl)-5-propyl-2,4(1H,3H)-pyrimidinedione gave 3-(3-{4-[2-(2,2,2-trifluoroethoxy)phenyl]piperazin-1-yl}propyl)-5-propyl-2,4(1H,3H)-pyrimidinedione hydrochloride, m.p. 135°–137° C.;

Anal.: Calcd. for $C_{22}H_{29}F_3N_4O_3.(HCl)_2$: C, 48.85; H 6.06; N, 10.36%; Found: C, 48.84; H, 5.95; N, 10.21%;

substituting 3-benzyl-1-{3-[4-(2-methoxyphenyl)piperazin-1-yl]propyl}-5-methyl-2,4(1H,3H)-pyrimidinedione gave 1-{3-[4-(2-methoxyphenyl)piperazin-1-yl]-propyl}-5-methyl-2,4(1H,3H)-pyrimidinedione hydrochloride, m.p. 239°–242° C.; Anal.: Calcd. for $C_{19}H_{26}N_4O_3.(HCl)_2$: C, 52.90; H, 6.54; N, 12.98%; Found: C, 53.32; H, 6.53; N, 13.13%;

substituting 1-benzyl-3-{3-[4-(4-fluoro-2-methoxyphenyl)piperazin-1-yl]propyl}-5-methyl-2,4(1H,3H)-pyrimidinedione gave 3-{3-[4-(4-fluoro-2-methoxyphenyl)piperazin-1-yl]propyl}-5-methyl-2,4(1H,3H)-pyrimidinedione hydrochloride, m.p. 240°–242° C.; Anal.: Calcd. for $C_{19}H_{25}FN_4O_3.(HCl)_2$: C, 50.78; H, 6.05; N, 12.46%; Found: C, 50.60; H, 6.03; N, 12.22%;

substituting 1-benzyl-3-{3-[4-(2-(2,2,2-trifluoroethoxy)phenyl)piperazin-1-yl]-propyl}-5-methyl-2,4(1H,3H)-pyrimidinedione gave 3-{3-[4-(2-(2,2,2-trifluoroethoxy)phenyl)piperazin-1-yl]propyl}-5-methy-2,4(1H,3H)-pyrimidinedione hydrochloride, m.p. 169°–171° C.; Anal.: Calcd. for $C_{20}H_{25}F_3N_4O_3.(HCl)_2$: C, 47.93; H, 5.47; N, 11.18%; Found: C, 48.06; H, 5.52, N, 10.88%;

substituting 1-benzyl-3-{3-[4-(2-methoxyphenyl)piperazin-1-yl]propyl}-5,6-dimethyl-2,4(1H,3H)-pyrimidinedione gave 3-{3-[4-(2-methoxyphenyl)piperazin-1-yl]propyl}-5,6-dimethyl-2,4(1H,3H)-pyrimidinedione hydrochloride, m.p. 237°–239° C.; Anal.: Calcd. for $C_{20}H_{28}N_4O_3.(HCl)_2$: C, 53.93; H, 6.78; N, 12.58%, Found: C, 53.73; H, 6.77; N, 12.36%;

substituting 1-benzyl-3-{3-[4-(2-methoxyphenyl)piperazin-1-yl]propyl}-5-methoxymethyl-2,4(1H,3H)-pyrimidinedione and recrystallizing from a solution of fumaric acid in alcohol gave 3-{3-[4-(2-methoxyphenyl)piperazin-1-yl]-propyl}-5-methoxymethyl-2,4(1H,3H)-pyrimidinedione fumarate as a foam; Anal.: Calcd. for $C_{20}H_{28}N_4O_4.C_4H_4O_4$: C, 56.13; H, 6.47; N, 10.91%; Found: C, 56.22; H, 6.47; N, 11.02%;

substituting 1-benzyl-3-{3-[4-(5-fluoro-2-methoxyphenyl)piperazin-1-yl]propyl}-5-methyl-2,4(1H,3H)-pyrimidinedione gave 3-{3-[4-(5-fluoro-2-methoxyphenyl)piperazin-1-yl]propyl}-5-methyl-2,4(1H,3H)-pyrimidinedione hydrochloride, m.p. 270° C. (dec); Anal.: Calcd. for $C_{19}H_{25}FN_4O_3.(HCl)_2$: C, 55.27; H, 6.35; N, 13.57%; Found: C, 55.03; H, 6.30; N, 13.56%;

substituting 1-benzyl-3-{3-[4-(2-methoxyphenyl)piperazin-1-yl]propyl}-5-trifluoromethyl-2,4(1H,3H)-pyrimidinedione gave 3-{3-[4-(2-methoxyphenyl)piperazin-1-yl]propyl}-5-trifluoromethyl-2,4(1H,3H)-pyrimidinedione hydrochloride, m.p. 257° C. (dec); Anal.: Calcd. for $C_{19}H_{23}F_3N_4O_3.(HCl)_{1.1}$: C, 50.42; H, 5.36; N, 12.38%; Found: C, 50.36; H, 5.62; N, 12.21%;

substituting 1-benzyl-3-{3-[4-(4-fluoro-2-(2,2,2-trifluoroethoxy)phenyl)piperazin-1-yl]propyl}-5-methyl-2,4(1H,3H)-pyrimidinedione and recrystallizing from a solution of fumaric acid in alcohol gave 3-{3-[4-(4-fluoro-2-(2,2,2-trifluoroethoxy)phenyl)piperazin-1-yl]propyl}-5-methyl-2,4(1H,3H)-pyrimidinedione fumarate, m.p. 190°–192° C.; Anal.: Calcd. for $C_{20}H_{24}N_4O_3.C_4H_4O_4$: C, 51.40; H, 5.03; N, 9.99%; Found: C, 51.45; H, 5.07; N, 9.92%;

substituting 1-benzyl-3-{3-[4-(2-methoxyphenyl)piperazin-1-yl]propyl}-5-ethyl-2,4(1H,3H)-pyrimidinedione gave 3-{3-[4-(2-methoxyphenyl)piperazin-1-yl]-propyl}-5-ethyl-2,4(1H,3H)-pyrimidinedione hydrochloride, m.p. 244°–246° C.; Anal.: Calcd. for $C_{20}H_{28}N_4O_3.(HCl)_2$: C, 52.87; H, 6.88; N, 12.33%; Found: C, 53.06; H, 6.71; N, 12.27%;

substituting 1-benzyl-3-{3-[4-(2-(2,2,2-trifluoroethoxy)phenyl)piperazin-1-yl]-propyl}-5-ethyl-2,4(1H,3H)-pyrimidinedione gave 3-{3-[4-(2-(2,2,2-trifluoroethoxy)phenyl)piperazin-1-yl]propyl}-5-ethyl-2,4(1H,3H)-pyrimidinedione hydrochloride, m.p. 169°–171° C.; Anal.: Calcd. for $C_{21}H_{27}N_4O_3.(HCl)_2$: C, 49.13; H, 5.69; N, 10.91%; Found: C, 49.01; H, 5.82; N, 11.20%;

substituting 3-benzyl-1-{3-[4-(2-(2,2,2-trifluoroethoxy)phenyl)piperazin-1-yl]-propyl}-5-methyl-2,4(1H,3H)-pyrimidinedione gave 1-{3-[4-(2-(2,2,2-trifluoroethoxy)phenyl)piperazin-1-yl]propyl}-5-methyl-2,4(1H,3H)-pyrimidinedione hydrochloride, m.p. 202°–203° C.; Anal.: Calcd. for $C_{20}H_{25}F_3N_4O_3.(HCl)_2$: C, 47.25; H, 5.54; N, 11.02%; Found: C, 46.98; H, 5.73; N, 10.82%;

substituting 1-benzyl-3-{3-[4-(2-methoxyphenyl)piperazin-1-yl]propyl}-5-propyl-2,4(1H,3H)-pyrimidinedione gave 3-{3-[4-(2-methoxyphenyl)piperazin-1-yl]-propyl}-5-propyl-2,4(1H,3H)-pyrimidinedione hydrochloride, m.p. 237°–238° C.; Anal.: Calcd. for $C_{21}H_{30}N_4O_3.(HCl)_{1.9}$: C, 59.63; H, 7.38; N, 13.24%; Found: C, 53.24; H, 6.70; N, 11.54%;

substituting 1-benzyl-3-{3-[4-(2-(2,2,2-trifluoroethoxy)phenyl)piperazin-1-yl]-propyl}-5,6-dimethyl-2,4(1H,3H)-pyrimidinedione gave 3-{3-[4-(2-(2,2,2-trifluoroethoxy)phenyl)piperazin-1-yl]propyl}-5,6-dimethyl-2,4(1H,3H)-pyrimidinedione hydrochloride, m.p. 198°–199° C.; Anal.: Calcd. for $C_{21}H_{27}F_3N_4O_3.(HCl)_2$: C, 48.28; H, 5.78; N, 10.72%; Found: C, 48.26; H, 5.81; N, 10.77%;

substituting 1-benzyl-3-(3-{4-[2-(2,2,2-trifluoroethoxy)phenyl]piperazin-1-yl}-propyl)-5,5-dimethyl-2,4,6(1H,3H,5H)-pyrimidinetrione and recrystallizing from a solution of fumaric acid in alcohol gave 3-(3-{4-[2-(2,2,2-trifluoroethoxy)phenyl]piperazin-1-yl}propyl)-5,5-dimethyl-2,4,6(1H,3H,5H)-pyrimidinetrione fumarate, m.p. 200° C.; Anal.: Calcd. for $C_{21}H_{27}F_3N_4O_4.(C_4H_4O_4)_{0.5}.(CH_4O)_{1.5}$: C, 52.31; H, 6.27; N, 9.96%; Found: C, 51.95; H, 5.91; N, 10.35%;

substituting 1-benzyl-3-{3-[4-(2-methoxyphenyl)piperazin-1-yl]propyl}-5,5-dimethyl-2,4,6(1H,3H,5H)-pyrimidinedione and recrystallizing from a solution of fumaric acid in alcohol gave 3-{3-[4-(2-methoxyphenyl)piperazin-1-yl]propyl}-5,5-dimethyl-2,4,6(1H,3H,5H)-pyrimidinetrione fumarate, m.p. 196° C.; Anal.: Calcd. for $C_{20}H_{28}N_4O_4.C_4H_4O_4.(H_2O)_{0.5}$: C, 56.13; H, 6.48; N, 10.91%; Found: C, 56.02; H, 6.43; N, 10.85%;

substituting 1-benzyl-3-(3-{4-[2-(2,2,2-trifluoroethoxy)phenyl]piperazin-1-yl}-2,2-dimethylpropyl)-5-methyl-2,4(1H,3H)-pyrinidinedione and recrystallizing from a solution of fumaric acid in alcohol gave 3-(3-{4-[2-(2,2,2-trifluoroethoxy)phenyl]piperazin-1-yl}-2,2-dimethylpropyl)-5-methyl-2,4(1H,3H)-pyrimidinedione fumarate, m.p. 143°–144° C.; Anal.: Calcd. for $C_{22}H_{29}F_3N_4O_3.C_4H_4O_4$: C, 54.73; H, 5.83; N, 9.82%; Found: C, 54.77; H, 5.81; N, 9.78%;

substituting 1-benzyl-3-{3-[4-(4-fluoro-2-methoxyphenyl)piperazin-1-yl]propyl}-5,5-dimethyl-2,4,6(1H,3H,5H)-pyrimidinetrione and recrystallizing from a solution of fumaric acid in alcohol gave 3-{3-[4-(4-fluoro-2-methoxyphenyl)piperazin-1-yl]propyl}-5,5-dimethyl-2,4,6(1H,3H,5H)-pyrimidinetrione fumarate, m.p. 171° C.; Anal.: Calcd. for $C_{20}H_{27}FN_4O_4.(C_4H_4O_4)_{0.5}.(H_2O)_{1.25}$: C, 54.26; H, 6.52; N, 11.50%; Found: C, 54.07; H, 6.35; N, 11.39%;

substituting 1-benzyl-3-(1-{4-[2-(2,2,2-trifluoroethoxy)phenyl]piperazin-1-ylmethyl}cycloprop-1-yl-methyl)-5-methyl-2,4(1H,3H)-pyrimidinedione and recrystallizing from a solution of fumaric acid in alcohol gave 3-(1-{4-

[2-(2,2,2-trifluoroethoxy)phenyl]piperazin-1-ylmethyl}cycloprop-1-yl-methyl)-5-methyl-2,4(1H,3H)-pyrimidinedione fumarate as a foam; Anal.: Calcd. for $C_{22}H_{27}F_3N_4O_3 \cdot (C_4H_4O_4)_{1.5}$: C, 53.67; H, 5.31; N, 8.94%; Found: C, 53.61; H, 5.50; N, 8.90%;

substituting 1-benzyl-3-{1-[4-(2-methoxyphenyl)piperazin-1-ylmethyl]cycloprop-1-yl-methyl}-5-methyl-2,4(1H,3H)-pyrimidinedione and recrystallizing from a solution of fumaric acid in alcohol gave 3-{1-[4-(2-methoxyphenyl)piperazin- 1-ylmethyl]cycloprop-1-yl-methyl}-5-methyl-2,4(1H,3H)-pyrimidinedione fumarate as a foam; Anal.: Calcd. for $C_{21}H_{28}N_4O_3 \cdot C_4H_4O_4$: C, 58.11; H, 6.59; N, 10.84%; Found: C, 58.38; H, 6.50; and N, 10.52%;

substituting 1-benzyl-3-(3-{4-[4-fluoro-2-(2,2,2-trifluoroethoxy)phenyl]piperazin-1-yl}propyl)-5,5-dimethyl-2,4,6(1H,3H,5H)-pyrimidinetrione and recrystallizing from a solution of fumaric acid in alcohol gave 3-(3-{4-[4-fluoro-2-(2,2,2-trifluoroethoxy)phenyl]piperazin-1-yl}propyl)-5,5-dimethyl-2,4,6(1H,3H,5H)-pyrimidinetrione fumarate, m.p. 132° C.; Anal.: Calcd. for $C_{21}H_{26}F_4N_4O_4 \cdot (C_4H_4O_4)_{0.5} \cdot (H_2O)_{1.25}$: C, 49.77; H, 5.54; N, 10.09%; Found: C, 49.69; H, 5.44; N, 9.96.

Example 33

3-{3-[4-(2-methoxyphenyl)piperazin-1-yl]propyl}-1,5-dimethyl-2,4(1H,3H)-pyrimidinedione The following is the preparation of a compound of Formula I in which $R^1$ is methoxy, $R^2$ is hydro, $R^3$ and $R^4$ are hydro and $R^5$ is a group of Formula (a), wherein Z is CH and $R^6$ and $R^7$ are each methyl.

A mixture of 3-{3-[4-(2-methoxyphenyl)piperazin-1-yl]propyl}-5-methyl-2,4(1H,3H)-pyrimidinedione (550 mg, 1.53 mmol), prepared as in Example 32, dimethyl sulfate (193 mg, 1.53 mmol) and 0.1N tetrabutylammonium fluoride (100 mL, 10 mmol in THF) was stirred 4 hours at 25° C. The reaction mixture then was concentrated in vacuo and the residue was purified by column chromatography on silica gel eluting with ethyl acetate to give 3-{3-[4-(2-methoxyphenyl)piperazin-1-yl]propyl}-1,5-dimethyl-2,4(1H,3H)-pyrimidinedione, as an oil. The free base was recrystallized from a solution of hydrochloric acid in alcohol to give 3-{3-[4-(2-methoxyphenyl)piperazin-1-yl]propyl}-1,5-dimethyl-2,4(1H,3H)-pyrimidinedione hydrochloride, m.p. 256°–258° C. Anal.: Calcd. for $C_{20}H_{28}N_4O_3 \cdot (HCl)_2$: C, 53.93; H, 6.79; N, 12.58%; Found: C, 54.05; H, 6.87; N, 12.58%.

Proceeding as in Example 33, but substituting other starting materials for 3-{3-[4-(2-methoxyphenyl)piperazin-1-yl]propyl}-5-methyl-2,4(1H,3H)-pyrimidinedione and/or dimethyl sulfate, the following compounds of Formula I were prepared:

substituting 1-{3-[4-(2-methoxyphenyl)piperazin-1-yl]propyl}-5-methyl-2,4(1H,3H)-pyrimidinedione gave 1-{3-[4-(2-methoxyphenyl)piperazin-1-yl]-propyl}-3,5-dimethyl-2,4(1H,3H)-pyrimidinedione hydrochloride, m.p. 242°–244° C.; Anal.: Calcd. for $C_{20}H_{28}N_4O_3 \cdot (HCl)_2$: C, 53.93; H, 6.78; N, 12.58%; Found: C, 53.70; H, 6.92; N, 12.58%;

substituting 3-{3-[4-(2-(2,2,2-trifluoroethoxy)phenyl)piperazin-1-yl]propyl}-5-methyl-2,4(1H,3H)-pyrimidinedione and 4-chlorobenzyl chloride gave 1-(4-chlorobenzyl)-3-{3-[4-(2-(2,2,2-trifluoroethoxy)phenyl)piperazin-1-yl]-propyl}-5-methyl-2,4(1H,3H)-pyrimidinedione hydrochloride, m.p. 170°–172° C.; Anal.: Calcd. for $C_{27}H_{30}ClF_3N_4O_3 \cdot HCl$: C, 55.20; H, 5.31; N, 9.53%; Found: C, 55.01; H, 5.24; N, 9.56%;

substituting 3-{3-[4-(2-(2,2,2-trifluoroethoxy)phenyl)piperazin-1-yl]propyl}-5-methyl-2,4(1H,3H)-pyrimidinedione and 3-chlorobenzyl chloride gave 1-(3-chlorobenzyl)-3-{3-[4-(2-(2,2,2-trifluoroethoxy)phenyl)piperazin-1-yl]-propyl}-5-methyl-2,4(1H,3H)-pyrimidinedione hydrochloride, m.p. 142°–144° C.; Anal.: Calcd. for $C_{27}H_{30}ClF_3N_4O_3 \cdot HCl$: C, 55.03; H, 5.33; N, 9.50%; Found: C, 54.80; H, 5.27; N, 9.46%;

substituting 3-{3-[4-(2-(2,2,2-trifluoroethocy)phenyl)piperazin-1-yl]propyl}-5-methyl-2,4(1H,3H)-pyrimidinedione and 2-picolyl chloride hydrochloride and recrystallizing from a solution of fumaric acid in alcohol gave 3-{3-[4-(2-(2,2,2-trifluoroethoxy)phenyl)pipearazin-1-yl]propyl}-5-methyl-1-pyrid-2-ylmethyl-2,4(1H,3H)-pyrimidinedione fumarate, m.p. 134°–135° C.; Anal.: Calcd. for $C_{26}H_{30}F_3N_5O_3 \cdot C_4H_4O_4$: C, 56.07; H, 5.49; N, 10.90%; Found: C, 55.82; H, 5.64; N, 11.05%;

substituting 3-{3-[4-(2-(2,2,2-trifluoroethcxy)phenyl)piperazin-1-yl]propyl}-5-methyl-2,4(1H,3H)-pyrimidinedione and 2-chlorobenzyl chloride gave 1-(2-chlorobenzyl)-3-{3-[4-(2-(2,2,2-trifluoroethoxy)phenyl)piperazin-1-yl]-propyl}-5-methyl-2,4(1H,3H)-pyrimidinedione hydrochloride, m.p. 152°–153° C.; Anal.: Calcd. for $C_{27}H_{30}ClF_3N_4O_3 \cdot HCl$: C, 55.20; H, 5.31; N, 9.53%; Found: C, 54.99; H, 5.38; N, 9.56%;

substituting 3-{3-[4-(2-(2,2,2-trifluoroethoxy)phenyl)piperazin-1-yl]propyl}-5-methyl-2,4(1H,3H)-pyrimidinedione and 2,6-dimethylbenzyl chloride and recrystallizing from a solution of fumaric acid in alcohol gave 3-{3-[4-(2-(2,2,2-trifluoroethoxy)phenyl)piperazin-1-yl]propyl}-5-methyl-1-(2,6-dimethylbenzyl)-2,4(1H,3H)-pyrimidinedione fumarate, m.p. 121°–124° C.; Anal.: Calcd. for $C_{29}H_{35}F_3N_4O_3 \cdot C_4H_4O_4$: C, 58.40; H, 6.09; N, 8.26%; Found: C, 58.63; H, 6.14; N, 8.36%; and substituting 3-(3-{4-[2-(2,2,2-trifluoroethoxy)phenyl]piperazin-1-yl}propyl)-5-methyl-2,4(1H,3H)-pyrimidinedione and 4-methylbenzyl chloride gave 3-(3-{4-[2-(2,2,2-trifluoroethoxy)phenyl]piperazin-1-yl}propyl)- 1-(4-methylbenzyl)-5-methyl-2,4(1H,3H)-pyrimidinedione hydrochloride, m.p. 141°–143° C.; Anal.: Calcd. for $C_{28}H_{33}F_3N_4O_3 \cdot (HCl)_2$: C, 55.89; H, 5.99; N, 9.12%; Found: C, 56.18; H, 5.99; N, 9.31%.

Example 34

1-(4-Methoxybenzyl)-3-{3-[4-(2-methoxyphenyl)piperazin-1-yl]propyl}-2,4-dioxo-5(1H,3H)-pyrimidinecarboxamide The following is the preparation of a compound of Formula I in which $R^1$ is methoxy, $R^2$, $R^3$ and $R^4$ is hydro and $R^5$ is a group of Formula (a) wherein Z is CH, $R^6$ is 4-methoxyphenyl and $R^7$ is carbamoyl.

A mixture of 5-cyano-1-(4-methoxybenzyl)-3-{3-[4-(2-methoxyphenyl)piperazin-1-yl]propyl}-2,4(1H,1H)-pyrimidined-one (450 mg, 0.92 mmol), prepared as in Example 25, and trifluoroacetic acid (4 mL) was heated 4 days at reflux. The reaction mixture then was concentrated in vacuo and the residue was dissolved in methylene chloride. The solution was washed with 10% aqueous sodium hydroxide and then water, dried ($Na_2SO_4$), filtered and concentrated in vacuo. The residue was purified by preparative thin layer chromatography on silica gel eluting with methylene chloride/methanol (97:3) to give 1-(4-methoxybenzyl)-3-{3-[4-(2-methoxyphenyl)piperazin-1-yl]propyl}-2,4-dioxo-5(1H,3H)-pyrimidinecarboxamide as a foam. The free base was recrystallized for a solution of hydrochloric acid in alcohol to give 1-(4-methoxybenzyl)-3-{3-[4-(2-methoxyphenyl)piperazin-1-yl]propyl}-2,4-dioxo-5(1H,3H)-pyrimidinecarboxamide hydrochloride, m.p. 157°–158° C. Anal.: Calcd. for $C_{27}H_{33}N_5O_5 \cdot (HCl)_2$: C, 53.06; H, 6.30; N, 11.46%; Found: C, 53.35; H, 5.90; N, 11.12%.

Example 35 cis-3-(3-{4-[4-Fluoro-2-(2,2,2-trifluoroethoxy)phenyl]piperazin-1-yl}propyl)-5,6-dihydroxy-5-methyl-5,6-dihydro-2,4(1H,3H)-pyrimidinedione The following is the preparation of the cis-isomers of a compound of Formula I in which $R^1$ is 2,2,2-trifluoroethoxy, $R^2$ is fluoro in the 4-position, $R^3$ and $R^4$ are each hydro and $R^5$ is a group of Formula (c) wherein X is CH(OH), $R^6$ is hydro and one of the $R^8$ radicals is hydroxy and the other is methyl.

A mixture of 3-(3-{4-[4-fluoro-2-(2,2,2-trifluoroethoxy)phenyl]piperazin-1-yl}propyl)-5-methyl-2,4(1H,3H)-pyrimidinedione (1.12 g, 2.52 mmol), prepared as in Example 32, trifluoroacetic acid (0.86 g, 7.56 mmol), water (0.82 mL) and DMSO (22 mL) was cooled to between 0° and 5° C. and N-bromosuccinimide (3.02 g/mL, 0.58 mL, 10.08 mmol) was added. The mixture was stirred in the dark at 25° C., treated with 5% sodium bicarbonate, stirred 1 hour, diluted water (10 mL) and then extracted with ethyl acetate (4×20 mL). The combined extracts were washed with water/brine (1:1, 1×30 mL), dried (MgSO$_4$) and concentrated. The residue was purified by flash chromatography on silica gel eluting with methylene chloride/methanol (93:7) to give cis-3-(3-{4-[4-fluoro-2-(2,2,2-trifluoroethoxy)phenyl]piperazin-1-yl}propyl)-5,6-dihydroxy-5-methyl-5,6-dihydro-2,4(1H,3H)-pyrimidinedione (0.49 g, 1.03 mmol), m.p. 110° C. Free base (0.49 mg, 1.01) was recrystallized from a solution of fumaric acid in methanol to give cis-3-(3-{4-[4-fluoro-2-(2,2,2-trifluoroethoxy)phenyl]piperazin-1-yl}propyl)-5,6-dihydroxy-5-methyl-5,6-dihydro-2,4(1H,3H)-pyrimidinedione fumarate (493 mg, 0.83 mmol), m.p. 155° C.; Anal.: Calcd. for $C_{20}H_{26}F_4N_4O_5 \cdot C_4H_4O_4$: C, 48.49; H, 5.09; N, 9.42%; Found: C, 48.33; H, 5.08; N, 9.61%;

Proceeding as in Example 35, but substituting 3-(3-{4-[2-(2,2,2-trifluoroethoxy)phenyl]piperazin-1-yl}propyl)-5-methyl-2,4(1H,3H)-pyrimidinedione for 3-(3-{4-[4-fluoro-2-(2,2,2-trifluoroethoxy)phenyl]piperazin-1-yl}propyl)-5-methyl-2,4(1H,3H)-pyrimidinedione gave cis-3-(3-{4-[2-(2,2,2-trifluoroethoxy)phenyl]piperazin-1-yl}propyl)-5,6-dihydroxy-5-methyl-5,6-dihydro-2,4(1H,3H)-pyrimidinedione fumarate, m.p. 125°–126° C. Anal.: Calcd. for $C_{20}H_{27}F_3N_4O_5 \cdot (C_4H_4O_4)_{0.5} \cdot (H_2O)_{0.75}$: C, 49.67; H, 5.78; N, 10.53%; Found: C, 49.73; H, 5.55; N, 10.48%.

The following shows the use of bromine in aqueous tert-butanol as the hydroxylating agent.

3-(3-{4-[4-Fluoro-2-(2,2,2-trifluoroethoxy)phenyl]piperazin-1-yl}propyl-5-methyl-2,4(1H,3H)-pyrimidinedione (1.2 Kg, 2.7 mol) was dissolved in a mixture of water (4.8 L), methanesulfonic acid (360 mL, 5.55 mol), and tert-butanol (3.0 L); and the solution cooled to about 5° C. The brominating reagent was prepared by the slow addition of tert-butanol (1.9 L) to a cooled biphasic mixture of bromine (160 mL, 3.105 mol) and water (1.1 L), then stirring the homogeneous reagent mixture for about 2 hours, maintaining the temperature at about 5° C. throughout. The cold brominating reagent was added slowly to the cold solution of the 3-(3-{4-[4-fluoro-2-(2,2,2-trifluoroethoxy)phenyl]piperazin-1-yl}propyl-5-methyl-2,4(1H,3H)-pyrimidinedione, maintaining the temperature at about 5° C., until the mixture showed a persistent yellow color (about 91% of the brominating reagent was used). An aqueous solution of dipotassium hydrogen phosphate (2 Kg, 11.48 mol, in 2.5 L water) was then added, and the resulting mixture stirred overnight, with the temperature being allowed to rise to room temperature. Ethyl acetate (2 L) was then added, forming a biphasic mixture. The pH of the aqueous phase, initially about 6.5, was increased to 8–8.5 by the addition of saturated aqueous potassium carbonate solution, and the reaction mixture was stirred for 15 minutes. The phases were then separated; and the aqueous phase extracted with ethyl acetate (2×2 L). The combined ethyl acetate phase was washed with saturated brine (2×2 L), and the brine backwashed with ethyl acetate (2×1 L). The combined ethyl acetate phase was then dried with anhydrous sodium sulfate and filtered through a bed of filter aid (Solka Floc). The ethyl acetate phase was concentrated under vacuum, and subsequently replaced with isopropyl acetate, adjusting the final volume to about 15 L. The resulting slurry was heated briefly to about 70° C. to ensure complete dissolution of the product, filtered through Solka Floc to remove any insoluble contaminants, and allowed to cool slowly to room temperature. A first crop of the precipitated product, cis-3-(3-{4-[4-fluoro-2-(2,2,2-trifluoroethoxy)phenyl]piperazin-1-yl}propyl-5,6-dihydroxy-5-methyl-5,6-dihydro-2,4(1H,3H)-pyrimidinedione, was isolated by filtration, washed with isopropyl acetate, and air-dried. The mother liquor and washings were combined, concentrated under vacuum to about 4 L, and allowed to cool slowly to room temperature, yielding a second crop of product. The combined product was mixed with maleic acid (300 g, 2.585 mol) and acetone (5 L). The resulting solution was heated to 40°–50° C., and isopropyl acetate (8 L) added slowly. The resulting slurry was heated again to 40°–50° C., and allowed to cool slowly to about 15° C. The precipitated product, cis-3-(3-{4-[4-fluoro-2-(2,2,2-trifluoroethoxy)phenyl]piperazin-1-yl}propyl-5,6-dihydroxy-5-methyl-5,6-dihydro-2,4(1H,3H)-pyrimidinedione maleate, was isolated by filtration, washed with isopropyl acetate, and dried at 45° C. under vacuum.

The following is the resolution of cis-3-(3-{4-[4-fluoro-2-(2,2,2-trifluoroethoxy)phenyl]piperazin-1-yl}propyl)-5,6-dihydroxy-5-methyl-5,6-dihydro-2,4(1H,3H)-pyrimidinedione by chiral chromatography.

cis-3-(3-{4-[4-Fluoro-2-(2,2,2-trifluoroethoxy)phenyl]piperazin-1-yl}-propyl)-5,6-dihydroxy-5-methyl-5,6-dihydro-2,4(1H,3H)-pyrimidinedione fumarate, prepared as above, was dissolved in ethanol to a concentration of 20 mg/mL. A 2.0 mL fraction was injected onto a Chiralpak AS (2×250 cm) column, and was eluted with hexane/ethanol/diethylamine (90:9.9:0.1) at 8.0 mL/min, monitoring the eluate by UV absorption at 238 nm. The (+)-enantiomer eluted first, and the (−)-enantiomer second.

After repeated injections and elutions, the fractions highly enriched in the (+)-enantiomer were pooled and concentrated to give 610 mg (1.28 mmol) of the free base. This material was dissolved in warm methanol (10 mL), and fumaric acid (148 mg, 1.28 mmol) added and dissolved. A suspension of a fine powder was obtained on the addition of ethyl acetate (15 mL). The suspension was aged at room temperature, filtered and dried in vacuo, and the solids recrystallized to give 400 mg of the (+)-enantiomer of cis-3-(3-{4-[4-fluoro-2-(2,2,2-trifluoroethoxy)phenyl]piperazin-1-yl}propyl)-5,6-dihydroxy-5-methyl-5,6-dihydro-2,4(1H,3H)-pyrimidinedione fumarate: m.p. 183.5°–192.1° C., $[\alpha]_D$+13.2° (c=0.34, MeOH). The product was analyzed using an analytical Chiralpak AS column, and found to consist of 94.9% (+)-enantiomer and 5.1% (−)-enantiomer.

Similarly, the fractions highly enriched in the (−)-enantiomer were pooled and concentrated to give 540 mg of the free base. This material was dissolved in warm methanol (10 mL), and fumaric acid (130 mg) added and dissolved. A suspension of a fine powder was obtained on the addition of ethyl acetate (15 mL). The suspension was aged at room temperature, filtered and dried in vacuo to give 356 mg of the (−)-enantiomer of cis-3-(3-{4-[4-fluoro-2-(2,2,2-trifluoroethoxy)phenyl]piperazin-1-yl}propyl)-5,6-dihydroxy-5-methyl-5,6-dihydro-2,4(1H,3H)-pyrimidinedione fumarate: m.p. 169.5°–178.0° C., $[\alpha]_D$–15.6° (c=0.48, MeOH). The product was analyzed using an analytical Chiralpak AS column, and found to consist of 91.9% (−)-enantiomer and 8.1% (+)-enantiomer.

Example 36
trans-3-(3-{4-[4-Fluoro-2-(2,2,2-trifluoroethoxy)phenyl] piperazin-1-yl}propyl)-5,6-dihydroxy-5-methyl-5,6-dihydro-2,4(1H,3H)-pyrimidinedione The following is the preparation of the trans-isomers of a compound of Formula I in which $R^1$ is 2,2,2-trifluoroethoxy, $R^2$ is fluoro in the 4-position, $R^3$ and $R^4$ are each hydro and $R^5$ is a group of Formula (c) wherein X is CH(OH), $R^6$ is hydro and one of the $R^8$ radicals is hydroxy and the other is methyl.

A mixture of cis-3-(3-{4-[4-fluoro-2-(2,2,2-trifluoroethoxy)phenyl]piperazin-1-yl}propyl)-5,6-dihydroxy-5-methyl-5,6-dihydro-2,4(1H,3H)-pyrimidinedione (600 mg, 1.42 mmol), prepared as in Example 35, para-toluenesulfonic acid monohydrate (1.2 g, 6.3 mmol) and DMSO (46 mL) was heated 14 hours at 50° C. The mixture was allowed to cool to approximately 25° C., neutralized by treatment with saturated sodium bicarbonate, and extracted with ethyl acetate (4×30 mL). The combined organic extracts were washed with water (1×20 mL) and brine, dried ($MgSO_4$) and concentrated. The residue was purified by loading onto preparative silica plates and developing twice with methylene chloride/methanol (93:7) to give trans-3-(3-{4-[4-fluoro-2-(2,2,2-trifluoroethoxy)phenyl]piperazin-1-yl}-propyl)-5,6-dihydroxy-5-methyl-5,6-dihydro-2,4(1H,3H)-pyrimidinedione (102 mg, 0.21 mmol) as a foam.

Example 37

The following are representative pharmaceutical formulations containing a compound of Formula I.

ORAL FORMULATION

A representative solution for oral administration contains:

Compound of Formula I 100–1000 mg

Citric Acid Monohydrate 105 mg

Sodium Hydroxide 18 mg

Flavoring

Water q.s. to 100 mL

INTRAVENOUS FORMULATION

A representative solution for intravenous administration contains:

Compound of Formula I 10–100 mg

Dextrose Monohydrate q.s. to make isotonic

Citric Acid Monohydrate 1.05 mg

Sodium Hydroxide 0.18 mg

Water for Injection q.s. to 1.0 mL

TABLET FORMULATION

A representative tablet form of a compound of Formula I may contain:

Compound of Formula I 1%

Microcrystalline Cellulose 73%

Stearic Acid 25%

Colloidal Silica 1%

Example 38
$\alpha_1$-Adrenoceptor In Vitro, Functional Assay in Tissue Isolated from Rabbit and Rat The following describes in vitro assays; for measuring the relative effect of test compounds on $\alpha_1$-adrenoceptor mediated, contraction of rat, isolated aortic smooth muscle and rabbit, isolated urinary bladder smooth muscle.

Thoracic aorta were isolated from rats and immediately immersed in Krebs' solution (comprising in mM concentrations: NaCl, 118.5; $NaHCO_3$, 25; dextrose, 5; KCl, 4.8; $CaCl_2$, 2.5; $MgSO_4$, 1.2; $KH_2PO_4$, 1.2; cocaine, 0.03; corticosterone, 0.03; propranolol, 0.001; ascorbic acid, 0.1; and indomethacin, 0.01). The aortas were dissected free from extraneous tissue and then a cross sectional ring approximately 3 mm in length was cut from the most proximal segment. The aortic rings were suspended vertically in 10 mL tissue baths and bathed in Krebs' solution maintained at 37° C. and constantly aerated with a 95% $O_2$ and 5% $CO_2$ gas mixture. A resting tension of 1 g was applied to each aortic ring and thereafter periodically readjusted to maintain a 1 g resting tension throughout the duration of the assay.

Urinary bladders were emptied and isolated from rabbits. Bladders were dissected free from extraneous tissue and then a cross sectional ring of bladder neck tissue was cut above the urethra to approximately one third of the way up the bladder. The bladder neck was cut parallel to the longitudinal muscle fibers to give flat section of muscle tissue and then the flat section was cut parallel to the longitudinal muscle to give several flat strips. Strips of bladder tissue were suspended vertically in 10 mL tissue baths and bathed in Krebs' solution maintained at 33° C. and constantly aerated with a 95% $O_2$ and 5% $CO_2$ gas mixture. A resting tension of 5 g was applied to each urinary bladder strip. The strips were allowed to relax to a resting tension of 1 g and thereafter periodically readjusted to maintain the 1 g resting tension throughout the duration of the assay.

The aortic ring or urinary bladder strip preparations were allowed to equilibrate for 60 minutes during which period the bath solution was replaced every 15 minutes. The tissue was then exposed to bath solution containing norepinephrine (0.1 to 10 μM) and once a steady state contraction was produced the tissue was exposed to bath solution free of norepinephrine, replacing the solution twice every 5 minutes for 30 minutes The aortic rings were exposed to norepinephrine and the urinary bladder strips to phenylephrine in a cumulative concentration fashion. That is, the isolated tissue was exposed to bath solution containing a threshold concentration of either norepinephrine or phenylephrine until a steady state contractile response was attained and then the concentration of agonist was cumulatively increased by 0.5 log increments until a maximal or near maximal response was attained. Norepinephrine produced a concentration-dependent, $\alpha_1$-adrenoceptor mediated contraction of the aortic rings. Phenylephrine produced a concentration-dependent, $\alpha_1$-adrenoceptor mediated contraction of the urinary bladder strips.

The tissue was then exposed to solution free of agonist, replacing the solution twice every 5 minutes for 30 minutes. After baseline tension was established and readjusted to 1 g, the tissue was exposed to bath solution containing the test compound, replacing the solution every 15 minutes for 60 minutes. In the presence of the test compound, the tissue again was exposed to either norepinephrine or phenylephrine in a cumulative concentration fashion, increasing the agonist concentration until a maximal or near maximal response was achieved.

The concentration ratio (CR) of agonist necessary to produce equiactive responses in the absence and presence of the test compound was determined. Relying on the concentration ratio, the assay concentration (molar) of the test compound, and the relationship:

$$pA_2 = -\log \frac{[\text{test compound}]}{CR - 1}$$

the negative log of the dissociation constant ($pA_2$) for each test compound at $\alpha_1$-adrenoceptors were estimated for both aortic tissue and urinary bladder tissue.

Proceeding as in Example 38, compounds of Formula I were tested and found to selectively inhibit the $\alpha_1$-adrenoceptor mediated contractions of rabbit, isolated urinary bladder smooth muscle. In contrast, prazosin, an $\alpha_1$-adrenoceptor antagonist that has been proscribed for treating BPH, selectively inhibited the $\alpha_1$-adrenoceptor mediated contractions of rat, isolated aortic smooth muscle.

Example 39
$\alpha_1$-Adrenoceptor In Vitro, Functional Assay in Tissue Isolated from Human The following describes in vitro assays for measuring the relative effect of test compounds on $\alpha_1$-adrenoceptor mediated contractions of human, isolated arterial and urinary bladder smooth muscle.

Human arterial blood vessels were obtained post-mortem and immediately immersed in cold physiological saline solution. Within 24 hours of removal the isolated arterial tissue was placed in Krebs' solution (comprising in mM concentrations: NaCl, 118.5; NaHCO$_3$, 25; dextrose, 5; KCl, 4.8; CaCl$_2$, 2.5; MgSO$_4$, 1.2; KH$_2$PO$_4$, 1.2; cocaine, 0.03; corticosterone, 0.03; propranolol, 0.001; ascorbic acid, 0.1; and indomethacin, 0.01). The arteries were dissected free from extraneous tissue and then cut into cross sectional rings approximately 3 mm in length. The arterial rings were suspended vertically in 10 mL tissue baths and bathed in Krebs' solution maintained at 37° C. and constantly aerated with a 95% O$_2$ and 5% CO$_2$ gas mixture. A resting tension of 1 to 1.5 g was applied to each ring and thereafter periodically readjusted to maintain a 1 g resting tension throughout the duration of the assay.

Human prostatic and bladder neck smooth muscle tissue was obtained following radical cystoprostatectomies or radical prostatectomies and immediately immersed in Krebs' solution. The prostatic and bladder tissue was dissected free from extraneous tissue and then strips of tissue 0.8 to 1.2 cm in length and 3 to 5 mm in width were cut and suspended vertically in 10 mL tissue baths and bathed in Krebs' solution maintained at 37° C. and constantly aerated with a 95% O$_2$ and 5% CO$_2$ gas mixture. A resting tension of 0.75 to 1 g was applied to each muscle strip and thereafter periodically readjusted to maintain a 1 g resting tension throughout the duration of the assay.

The arterial ring and prostatic and bladder neck strip preparations were allowed to equilibrate for 60 minutes during which period the bath solution was replaced every 15 minutes. The tissue was then exposed to bath solution containing norepinephrine (1 to 10 $\mu$M) and once a steady state contraction was produced the tissue was exposed to bath solution free of norepinephrine, replacing the solution twice every 5 minutes for 30 minutes. The arterial ring and prostatic and bladder neck strip preparations were exposed to norepinephrine in a cumulative concentration fashion. That is, the isolated tissue was exposed to bath solution containing a threshold concentration of norepinephrine until a steady state contractile response was attained and then the concentration of norepinephrine was cumulatively increased by 0.5 log increments until a maximal or near maximal response was attained. Norepinephrine produced a concentration-dependent, $\alpha_1$-adrenoceptor mediated contraction of the arterial ring and of the prostatic and bladder neck strip preparations.

The tissue was then exposed to solution free of norepinephrine, replacing the solution twice every 5 minutes for 30 minutes. After baseline tension was established and readjusted to 1 g, the tissue was exposed to bath solution containing the test compound, replacing the solution every 15 minutes for 60 minutes. In the presence of the test compound, the tissue again was exposed to norepinephrine in a cumulative concentration fashion, increasing the norepinephrine concentration until a maximal or near maximal response was achieved.

The concentration ratio (CR) of norepinephrine necessary to produce equiactive responses in the absence and presence of the test compound was determined. Relying on the concentration ratio, the assay concentration (molar) of the test compound, and the relationship:

$$pA_2 = -\log \frac{[\text{test compound}]}{CR - 1}$$

the negative log of the dissociation constant ($pA_2$) for each test compound at $\alpha_1$-adrenoceptors were estimated for the arterial ring and prostatic and bladder neck strip preparations.

Proceeding as in Example 39, compounds of Formula I were tested and found to selectively inhibit the $\alpha_1$-adrenoceptor mediated contractions of human, isolated prostatic and bladder neck smooth muscle. In contrast, prazosin non-selectively inhibited the $\alpha_1$-adrenoceptor-mediated contractions of both human, isolated prostatic/bladder neck smooth muscle and isolated arterial smooth muscle.

Example 40
Rat In Vivo, Blood Pressure Assay

The following describes an in vivo assay for measuring the effect of test compounds on blood pressure in normotensive and spontaneously hypertensive rats.

Normotensive or spontaneously hypertensive rats (0.25 to 0.45 kg) were fasted for 18 hours and anesthetized with ether. The right femoral vein was isolated and cannulated with a fluid filled polyethylene cannulae for bolus administration of test substances. The right femoral artery was isolated and cannulated with a fluid filled polyethylene cannula connected to an external pressure transducer for monitoring mean arterial blood pressure (MAP).

The rats were placed in restrainers and allowed to recover from anesthesia. Following a 30 minute period for stabilization, test compounds or vehicle were administered, i.v., and blood pressure was monitored continuously for at least 4 hours post-administration.

Proceeding as in Example 40, compounds of Formula I were tested and found to be considerably less potent than prazosin at producing blood pressure lowering effects.

Example 41
Rat In Vivo, Tilt-Response Assay

The following describes an in vivo assay in normotensive rats for measuring the propensity of test compounds to inhibit the reflex maintenance of basal blood pressure levels in response to vertical tilt.

Normotensive rats (0.25 to 0.45 kg) were fasted for 18 hours and anesthetized with ether. The right femoral vein was isolated and cannulated with a fluid filled polyethylene cannulae for bolus administration of test substances. The right femoral artery was isolated and cannulated with a fluid filled polyethylene cannula connected to an external pressure transducer for monitoring mean arterial blood pressure (MAP).

The rats were restrained in a supine position and allowed to recover from anesthesia. Following a 30 minute period for stabilization, test compounds or vehicle were administered, i.v., and blood pressure was monitored continuously while the rats were tilted vertically at 30 to 60 degrees from supine at 15, 30 and 45 minutes post-administration.

Proceeding as in Example 41, compounds of Formula I were tested and found to be considerably less potent than prazosin at inhibiting the reflex maintenance of basal blood pressure levels in response to vertical tilt.

Example 42
Dog In Vivo, Blood and Intraurethral Pressure Assay

The following describes an in vivo assay for measuring the relative effect of test compounds on hypogastric nerve stimulation-induced increases in intraurethral pressure and phenylephrine-induced increases in diastolic blood pressure in anesthetized dog.

Mongrel dogs (10 to 20 kg) were fasted for 12 to 18 hours and anesthetized with phenobarbital sodium (35 mg/kg, i.v.). An endotracheal tube was inserted and thereafter the lungs were mechanically ventilated with room air. The right femoral vein was isolated and cannulated with two polyethylene cannulae, one for the administration of a continuous infusion of phenobarbital sodium (5 to 10 mg/kg/hr) and the other for bolus administration of test substances. The right femoral artery was isolated and cannulated to the abdominal aorta with a fluid filled polyethylene cannula connected to an external pressure transducer for monitoring diastolic aortic pressure (DAP). The bladder was exposed via a ventral midline abdominal incision and emptied of urine through a 22 gauge needle. The bladder was cannulated through a stab incision with a water filled balloon catheter connected to an external pressure transducer for monitoring prostatic intraurethral pressure (IUP). The right hypogastric nerve (HGN) was carefully isolated and attached to a Dastre's electrode for nerve stimulation.

The preparation was allowed to stabilize for a least 30 minutes and must have had a stable basal IUP for not less than 15 minutes prior to commencement of the assay protocol. The HGN was stimulated (20–50 V, 10 Hz, 10 msec pulse train for 10 sec) to induce a measurable increase in IUP and then phenylephrine (PE) was administered by bolus injection (0.5 to 0.6 μg/kg, i.v.) to induce a measurable increase in DUP. The HGN stimulation and PE bolus injection were repeated every 5 minutes until three consecutive reproducible increases in IUP and DAP were achieved. Vehicle (0.1 to 0.3 mL/kg) was administered and 20 minutes later the HGN stimulation and PE bolus injection were repeated. Test compound was then administered and 20 minutes later the HGN stimulation and PE bolus injection were repeated. Test compound was administered approximately every 20 minutes, increasing the dose until maximal or near maximal inhibition of the increases in IUP and DAP was attained.

Proceeding as in Example 42, compounds of Formula I were tested and found to selectively inhibit the HGN stimulation-induced increases in IUP. In contrast, prazosin inhibited increases in IUP and DAP in a similar fashion.

We claim:
1. A compound of the formula:

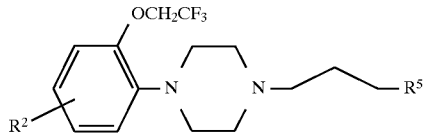

in which:
$R^2$ is chloro, fluoro, hydro, hydroxy, or methyl; and
$R^5$ is selected from Formula (a) or (b):

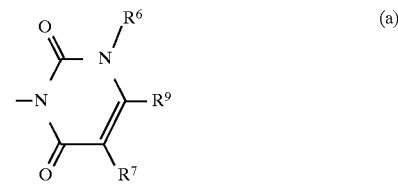

or

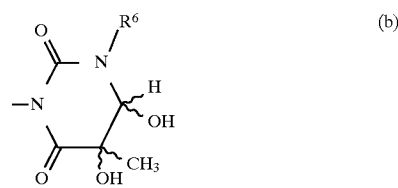

in which:
$R^6$ is hydro, methyl, cyclohexylmethyl, pyridylmethyl, pyrazinylmethyl, furylmethyl, thienylmethyl, biphenylmethyl, or a group selected from benzyl and phenyl (which group is optionally further substituted with one to three radicals selected from chloro, fluoro, methyl, or methoxy);
$R^7$ is hydro, hydroxymethyl, methyl, or ethyl; and
$R^9$ is hydro or methyl,
or a pharmaceutically acceptable salt or N-oxide thereof.

2. The compound of claim 1 in which $R^2$ is fluoro at the 4-position and $R^5$ is a group of Formula (a) in which $R^6$ is hydro, $R^7$ is methyl, and $R^9$ is hydro, namely 3-(3-{4-[4-fluoro-2-(2,2,2-trifluoroethoxy)phenyl]piperazin-1-yl}propyl)-5-methyl-2,4(1H,3H)-pyrimidinedione; or a pharmaceutically acceptable salt thereof.

3. The compound of claim 2 which is 3-(3-{4-[4-fluoro-2-(2,2,2-trifluoroethoxy)phenyl]piperazin-1-yl}propyl)-5-methyl-2,4(1H,3H)-pyrimidinedione fumarate.

4. The compound of claim 1 in which $R^2$ is fluoro at the 4-position and $R^5$ is a group of Formula (b) in which $R^6$ is hydro, namely 3-(3-{4-[4-fluoro-2-(2,2,2-trifluoroethoxy)phenyl]piperazin-1-yl}propyl)-5,6-dihydroxy-5-methyl-5,6-dihydro-2,4(1H,3H)-pyrimidinedione; or a pharmaceutically acceptable salt thereof.

5. The compound of claim 4 which is cis-3-(3-{4-[4-fluoro-2-(2,2,2-trifluoroethoxy)phenyl]piperazin-1-yl}propyl)-5,6-dihydroxy-5-methyl-5,6-dihydro-2,4(1H,3H)-pyrimidinedione; or a pharmaceutically acceptable salt thereof.

6. The compound of claim 5 which is cis-3-(3-{4-[4-fluoro-2-(2,2,2-trifluoroethoxy)phenyl]piperazin-1-yl}propyl)-5,6-dihydroxy-5-methyl-5,6-dihydro-2,4(1H,3H)-pyrimidinedione fumarate.

7. The compound of claim 1 in which $R^2$ is hydro and $R^5$ is a group of Formula (a) in which $R^6$ is hydro, $R^7$ is methyl, and $R^9$ is hydro, namely 3-(3-{4-[2-(2,2,2-trifluoroethoxy)phenyl]piperazin-1-yl}propyl)-5-methyl-2,4(1H,3H)-pyrimidinedione; or a pharmaceutically acceptable salt thereof.

8. The compound of claim 7 which is 3-(3-{4-[2-(2,2,2-trifluoroethoxy)phenyl]piperazin-1-yl}propyl)-5-methyl-2,4(1H,3H)-pyrimidinedione hydrochloride.

9. The compound of claim 1 in which $R^2$ is fluoro at the 4-position and $R^5$ is a group of Formula (a) in which $R^6$ is hydro, $R^7$ is ethyl, and Z is CH, namely 3-(3-{4-[4-fluoro-2-(2,2,2-trifluoroethoxy)phenyl]piperazin-1-yl}propyl)-5-ethyl-2,4(1H,3H)-pyrimidinedione; or a pharmaceutically acceptable salt thereof.

10. The compound of claim 9 which is 3-(3-{4-[4-fluoro-2-(2,2,2-trifluoroethoxy)phenyl]piperazin-1-yl}propyl)-5-ethyl-2,4(1H,3H)-pyrimidinedione hydrochloride.

11. The compound of claim 1 in which $R^2$ is fluoro at the 4-position and $R^5$ is a group of Formula (a) in which $R^6$ is hydro, $R^7$ is hydroxymethyl, and $R^9$ is hydro, namely 3-(3-{4-[4-fluoro-2-(2,2,2-trifluoroethoxy)phenyl]piperazin-1-yl}propyl)-5-hydroxymethyl-2,4(1H,3H)-pyrimidinedione; or a pharmaceutically acceptable salt thereof.

12. The compound of claim 11 which is 3-(3-{4-[4-fluoro-2-(2,2,2-trifluoroethoxy)phenyl]piperazin-1-yl}propyl)-5-hydroxymethyl-2,4(1H,3H)-pyrimidinedione fumarate.

13. A pharmaceutical composition comprising a therapeutically effective amount of a compound of claim 1, or a pharmaceutically acceptable salt or N-oxide thereof, in combination with a pharmaceutically acceptable excipient.

14. A pharmaceutical composition comprising a therapeutically effective amount of a compound of claim 2, or a pharmaceutically acceptable salt thereof, in combination with a pharmaceutically acceptable excipient.

15. A pharmaceutical composition comprising a therapeutically effective amount of a compound of claim 4, or a pharmaceutically acceptable salt or N-oxide thereof, in combination with a pharmaceutically acceptable excipient.

16. A method for treating a disease involving directly or indirectly an obstruction of the lower urinary tract in an animal in need of such treatment, which method comprises administering to such animal a therapeutically effective amount of a compound of claim 1, or a pharmaceutically acceptable salt or N-oxide thereof.

17. The method of claim 16 in which the disease state is benign prostatic hypertrophy.

18. A method for treating a disease involving directly or indirectly an obstruction of the lower urinary tract in an animal in need of such treatment, which method comprises administering to such animal a therapeutically effective amount of a compound of claim 2, or a pharmaceutically acceptable salt thereof.

19. The method of claim 18 in which the disease state is benign prostatic hypertrophy.

20. A method for treating a disease involving directly or indirectly an obstruction of the lower urinary tract in an animal in need of such treatment, which method comprises administering to such animal a therapeutically effective amount of a compound of claim 4, or a pharmaceutically acceptable salt or N-oxide thereof.

21. The method of claim 20 in which the disease state is benign prostatic hypertrophy.

* * * * *

UNITED STATES PATENT AND TRADEMARK OFFICE
CERTIFICATE OF CORRECTION

PATENT NO.  : 5,859,014
DATED       : Jan. 12, 1999
INVENTOR(S) : Bantle et al.

It is certified that error appears in the above-indentified patent and that said Letters Patent is hereby corrected as shown below:

Claim 9, column 69, line 3 "Z is CH" should read -- $R^9$ is hydro --.

Signed and Sealed this

First Day of June, 1999

Attest:

Attesting Officer

Q. TODD DICKINSON

Acting Commissioner of Patents and Trademarks